US011771697B2

(12) United States Patent
Fischer et al.

(10) Patent No.: US 11,771,697 B2
(45) Date of Patent: Oct. 3, 2023

(54) SMALL MOLECULE DEGRADERS OF POLYBROMO-1 (PBRM1)

(71) Applicant: DANA-FARBER CANCER INSTITUTE, INC., Boston, MA (US)

(72) Inventors: Eric Fischer, Chestnut Hill, MA (US); Nathanael Gray, Boston, MA (US); Radoslaw Nowak, Boston, MA (US); Katherine Donovan, Boston, MA (US); Tinghu Zhang, Brookline, MA (US); Yao Liu, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 152 days.

(21) Appl. No.: 17/042,634

(22) PCT Filed: Apr. 30, 2019

(86) PCT No.: PCT/US2019/029778
§ 371 (c)(1),
(2) Date: Sep. 28, 2020

(87) PCT Pub. No.: WO2019/213005
PCT Pub. Date: Nov. 7, 2019

(65) Prior Publication Data
US 2021/0038599 A1 Feb. 11, 2021

Related U.S. Application Data

(60) Provisional application No. 62/664,592, filed on Apr. 30, 2018.

(51) Int. Cl.
*A61K 31/501* (2006.01)
*A61K 45/06* (2006.01)

(52) U.S. Cl.
CPC ............ *A61K 31/501* (2013.01); *A61K 45/06* (2013.01)

(58) Field of Classification Search
CPC .... A61K 31/501; A61K 45/06; C07D 401/14; C07D 417/14; A61P 35/00
USPC ...................................... 544/238; 514/252.02
See application file for complete search history.

(56) References Cited

U.S. PATENT DOCUMENTS

| 2016/0176916 A1 | 6/2016 | Bradner et al. |
| 2018/0086720 A1 | 3/2018 | Albrecht et al. |

FOREIGN PATENT DOCUMENTS

| WO | 2017/030814 A1 | 2/2017 | |
| WO | WO-2017176957 A1 * | 10/2017 | ........... A61K 31/407 |
| WO | 2017/197051 A1 | 11/2017 | |
| WO | 2018/052949 A1 | 3/2018 | |
| WO | 2019/023149 A1 | 1/2019 | |
| WO | 20190195201 A1 | 10/2019 | |
| WO | 20190207538 A1 | 10/2019 | |
| WO | WO-2019207538 A1 * | 10/2019 | ........... C07D 401/14 |

OTHER PUBLICATIONS

Patrick Pfaff, Kusal T. G. Samarasinghe, Craig M. Crews, and Erick M. Carreira, Reversible Spatiotemporal Control of Induced Protein Degradation, by Bistable Photo PROTACs, ACS Cent. Sci. 2019, 5, 1682-1690; see, for example, the abstract and the whole document (Year: 2019).*
Kedra Cyrus, Marie Wehenkel, Eun-Young Choi, Hyeong-Jun Han, Hyosung Lee, Hollie Swanson and Kyung-Bo Kim, Impact of linker length on the activity of PROTACs, Mol. BioSyst., 2011, 7, 359-364 (Year: 2011).*
Bondeson, Daniel P., et al., "Lessons in PROTAC Design from Selective Degradation with a Promiscuous Warhead", Cell Chem Biol. 2018, vol. 25, No. 1, pp. 78-87.
Huang, Hai-Tsang, et al., "A Chemoproteomic Approach to Query the Degradable Kinome Using a Multi-Kinase Degrader", Cell Chem. Biol., 2018, vol. 25, No. 1, pp. 88-99.
Li, Xin., et al., "Proteolysis-Targeting Chimera (PROTAC) for Targeted Protein Degradation and Cancer Therapy", J. Hematol. Oncol., 2020, vol. 13, No. 50, pp. 1-14.
Su, S., et al., "Potent and Preferential Degradation of CDK6 via Proteolysis Targeting Chimera Degraders", J. Med. Chem. 2019, vol. 62, pp. 7575-7582.

* cited by examiner

*Primary Examiner* — Jeffrey H Murray
(74) *Attorney, Agent, or Firm* — BURNS & LEVINSON, LLP; Daniel W. Clarke; Shawn P. Foley

(57) ABSTRACT

The present invention relates to compounds, compositions and methods for treating diseases or conditions mediated by proteins of the SWI/SNF chromatin-remodeling complex, including PB1.

8 Claims, 15 Drawing Sheets

SMALL MOLECULE DEGRADERS OF POLYBROMO-1 (PBRM1)

RELATED APPLICATIONS

This application is a national stage application, filed under 35 U.S.C. § 371, of International Application No. PCT/US2019/029778, filed Apr. 30, 2019, which claims the benefit of priority under 35 U.S.C. § 119(e) to U.S. Provisional Application No. 62/664,592, filed Apr. 30, 2018, the entire contents of each of which isare incorporated herein by reference in their entirety.

BACKGROUND OF THE INVENTION

Chromatin is a complex combination of deoxyribonucleic acid (DNA) and protein that makes up chromosomes. It is found inside the nuclei of eukaryotic cells and is divided between heterochromatin (condensed) and euchromatin (extended) forms. The major components of chromatin are DNA and proteins. Chromatin packages DNA into a smaller volume to fit in the cell; it strengthens the DNA to allow mitosis and meiosis; and it serves as a mechanism to control expression and DNA replication.

Histones are the chief protein components of chromatin, acting as spools around which DNA winds. Chromatin structure is controlled by a series of post-translational modifications to histones, notably histones H3 and H4. Of all classes of proteins, histones are particularly susceptible to post-translational modification. Histone modifications are dynamic. They can be added or removed in response to specific stimuli. These modifications direct both structural changes to chromatin and alterations in gene transcription.

Bromodomains, which are approximately 110 amino acids long, are found in a large number of chromatin-associated proteins including histones. They have been identified in approximately 70 human proteins. Interactions between bromodomains and modified histones may be an important mechanism underlying chromatin structural changes and gene regulation. Bromodomain-containing proteins have been implicated in the etiology and progression of diseases including cancer, inflammation and viral replication.

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. An example of such a complex is the Switch/Sucrose Non-Fermentable (SWI/SNF) chromatin-remodeling complex. This complex is a nucleosome remodeling complex that includes a group of proteins that associate to remodel the way in which DNA is packaged inside the cell. The SWI/SNF chromatin-remodeling complex has been reported to be involved in gene regulation, cell linage specification and development and comprises a number of bromodomain containing subunits, including Brahma-related gene-1 (BRG1 (also known as SWI/SNF related, matrix associated, actin dependent regulator of chromatin, subfamily A, member 4 (SMARCA4)), brahma (BRM) (also known as SMARCA2) and protein polybromo-1 (PBRM1) (also known as PB1). PB1 has 6 distinct bromodomains. They have been linked to genome instability and aneuploidy. Inactivating mutations in SWISNF subunits have been reported to be found in nearly 20% of human cancers. For example, mutations in PB1's bromodomains have been found in clear cell renal carcinoma. BRM has been identified as a synthetic legal target in BRG1-deficient cancers (Hoffman et al., PNAS 111(8): 3128-3133 (2014); Oike et al., Cancer Research, 73(17): 5508-5518 (2013)). Yet other studies have shown that certain cancers lacking SWI/SNF mutations are sensitive to BRG1 inhibition.

Accordingly, there is a need for compounds that inhibit PB1 for treating diseases such as cancer.

SUMMARY OF THE INVENTION

A first aspect of the present invention is directed to a bivalent compound which is represented by Formula I:

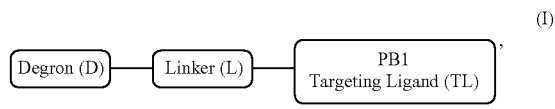

(I)

wherein the targeting ligand represents a moiety that binds an SWI/SNF bromodomain protein including PB1, the degron represents a moiety that binds an E3 ubiquitin ligase, and the linker represents a moiety that covalently connects the degron and the targeting ligand, or a pharmaceutically acceptable salt or stereoisomer thereof.

In another aspect, pharmaceutical composition including a therapeutically effective amount of the bivalent compounds of the present invention, or a pharmaceutically acceptable salt or stereoisomer thereof, and a pharmaceutically acceptable carrier are provided.

In another aspect, methods of making the bivalent compounds of the present invention are provided.

A further aspect of the present invention is directed to a method of treating a disease or disorder characterized or mediated by dysfunctional SWI/SNF activity (e.g, dysfunctional PB1 activity) that entails administering to a subject in need thereof a therapeutically effective amount of the bivalent compound, or a pharmaceutically acceptable salt or stereoisomer thereof.

DETAILED DESCRIPTION

Figure 1A:
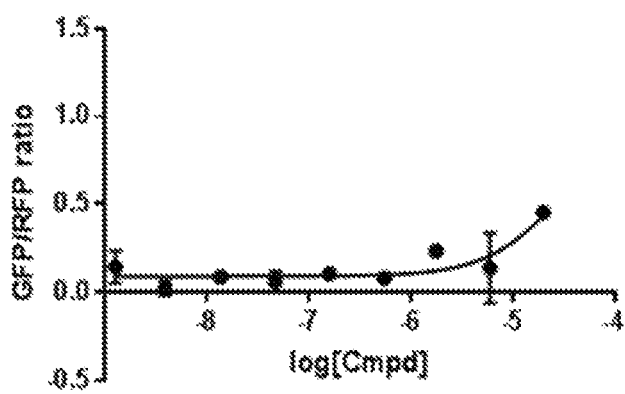
FIG. 1A-FIG. 1C are graphs that plots Green Fluorescence Protein/Red Fluorescence Protein (GFP/RFP) ratio as a function of concentration of inventive compounds 1-3, respectively, generated from a cellular cereblon (CRBN) binding assay.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to bivalent compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_5$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula-C(O)H. The terms "C(O)" and C=O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "oxo" refers to =O or (=O)$_2$.

As used herein, the term "carboxylic acid" is represented by the formula-C(O)OH, and a "carboxylate" is represented by the formula —C(O)O—.

As used herein, the term "ester" is represented by the formula —OC(O)Z$^1$ or —C(O)OZ$^1$, where Z$^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula Z$^1$C(O)Z$^2$, where A$^1$ and A$^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —S(O)$_2$Z$^1$, where Z$^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —S(O)$_2$NH$_2$.

As used herein, the term "thiol" is represented by the formula —SH.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_5$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl, alkenyl, substituted alkenyl, alkynyl, substituted alkynyl, cyclic, substituted cyclic, carbocyclic, substituted carbocyclic, heterocyclic, substituted heterocyclic, aryl (e.g., benzyl and phenyl), substituted aryl (e.g., substituted phenyl), heteroaryl, substituted heteroaryl, or $NR_6R_7$, wherein each of $R_6$ and $R_7$ independently represents H, optionally substituted aryl or optionally substituted aralkyl, halo, hydroxyl, alkoxy, substituted alkoxy, aryloxy, substituted aryloxy, alkylthio, substituted alkylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, amino acid, peptide, and polypeptide groups.

The term "binding" as it relates to interactions between the targeting ligand and the targeted protein or proteins, which in this invention is at least one SWI/SNF bromodomain protein including PB1, typically refers to an inter-molecular interaction that may be preferential or substantially specific in that binding of the targeting ligand with other non-SWISNF proteinaceous entities, including PB1, that may be present in the cell is functionally insignificant. The present bivalent compounds may preferentially bind and recruit at least one SWI/SNF protein including PB1. In some embodiments, the present bivalent compounds may also bind BRG1 and/or BRM for targeted degradation.

The term "binding" as it relates to interactions between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bivalent compounds of the present invention have a structure represented by formula I:

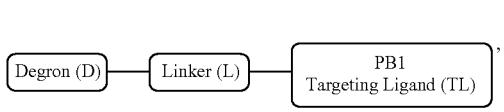

(I)

wherein the targeting ligand represents a moiety that binds an SWI/SNF bromodomain protein including PB1, the degron represents a moiety that binds an E3 ubiquitin ligase, and the linker represents a moiety that covalently connects the degron and the targeting ligand, or a pharmaceutically acceptable salt or stereoisomer thereof.

SWI/SNF (e.g., PB1) Targeting Ligands

The SWI/SNF targeting ligand (TL), which is a functional modality of the present bivalent compounds, binds PB1. In some embodiments, the TL may also bind BRG1 and/or BRM.

In some embodiments, the SWI/SNF targeting ligand (also referred to herein as a PB1 targeting ligand) is represented by the following structure:

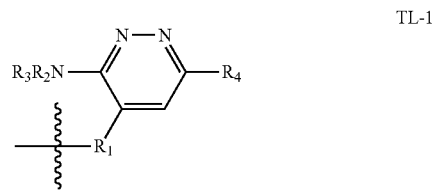

TL-1 or a pharmaceutically acceptable salt or stereoisomer thereof, wherein:

$R^1$ is selected from the group consisting of —$R^b$, —O—$R^b$, —S(O)$_2R^b$, and —C(O)—N($R^b$)$_2$; each $R^b$ is independently selected from the group consisting of hydrogen, $C_{1-6}$ alkyl, $C_{2-6}$ alkenyl, $C_{2-6}$ alkynyl, 3-15 membered carbocyclyl, and 3-15 membered heterocyclyl, wherein each $C_{1-6}$ alkyl, $C_{2-6}$ alkynyl, 3-15 membered carbocyclyl, and 3-15 membered heterocyclyl may be optionally substituted with one or more groups independently selected from R, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$—, wherein each $R^c$ is independently selected from hydrogen, $C_{1-6}$ alkyl, $C_{2-6}$ alkenyl, $C_{2-6}$ alkynyl, $C_{1-6}$ alkoxy, 3-15 membered carbocyclyl, and 3-15 membered heterocyclyl, wherein each $C_{1-6}$ alkyl, $C_{2-6}$ alkenyl, $C_{2-6}$ alkynyl, $C_{1-6}$ alkoxy, 3-15 membered carbocyclyl, and 3-15 membered heterocyclyl is optionally substituted with one or more groups independently selected from $R^d$; or two $R^c$ are taken together with the nitrogen to which they are attached to form a heterocyclyl that is optionally substituted with one or more groups independently selected from oxo, halo and $C_{1-3}$ alkyl that is optionally substituted with one or more groups independently selected from oxo and halo; and wherein each $R^d$ is independently selected from oxo, halo, —NO$_2$, —N($R^e$)$_2$, —CN, —C(O)—N($R^e$)$_2$, —S(O)—N($R^e$)$_2$, —S(O)$_2$—N ($R^e$)$_2$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, —N($R^e$)—S(O)$_2$—$R^e$, $C_{1-6}$ alkyl, $C_{2-6}$ alkenyl, $C_{2-6}$ alkynyl, 3-15 membered carbocyclyl, and 3-15 membered heterocyclyl, wherein any $C_{1-6}$ alkyl, $C_{2-6}$ alkenyl, $C_{2-6}$ alkynyl, 3-15 membered carbocyclyl, and 3-15 membered heterocyclyl is optionally substituted with one or more groups independently selected from $R^e$, oxo, halo, —NO$_2$, —N($R^e$)$_2$, —CN, —C(O)—N($R^e$)$_2$, —S(O)—N($R^e$)$_2$, —S(O)$_2$—N ($R^e$)$_2$, —O—$R^e$, —S—$R^e$, —O—C(O)$R^e$, —C(O)—(O)— O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, and —N($R^e$)—S(O)$_2$—$R^e$; and each $R^e$ is independently selected from the group consisting of hydrogen, $C_{1-6}$ alkyl, $C_{2-6}$ alkenyl, $C_{2-6}$ alkynyl, carbocyclyl, and carbocyclyl ($C_{1-3}$alkyl); $R_2$ is H, $C_{1-6}$ alkyl, or —C(=O)—$C_{1-6}$ alkyl; $R^3$ is H or $C_{1-6}$ alkyl; and $R^4$ is phenyl that is substituted with hydroxy (e.g., 2-hydroxy, 3-hydroxy, 4-hydroxy, 5-hydroxy and 6-hydroxy) and that is optionally further substituted with one or more groups independently selected from halo, cyano, trifluoromethyl, trifluoromethoxy, $C_{1-3}$ alkyl and $C_{1-3}$ alkoxy.

Referring to TL-1, in some embodiments, $R^2$ is H, methyl, or acetyl; $R^3$ is H; $R^4$ is as defined above, and $R^1$ is a group selected from
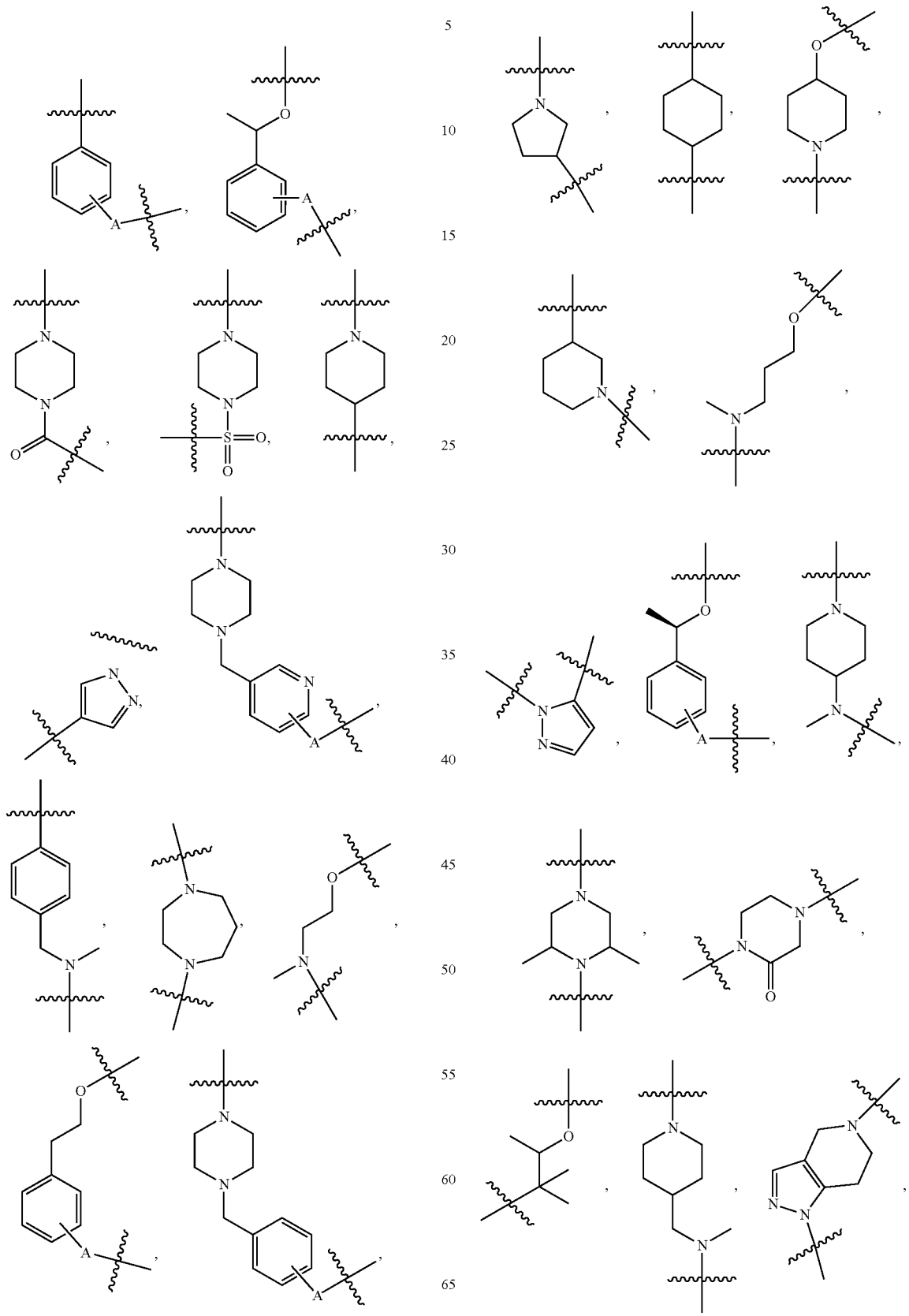

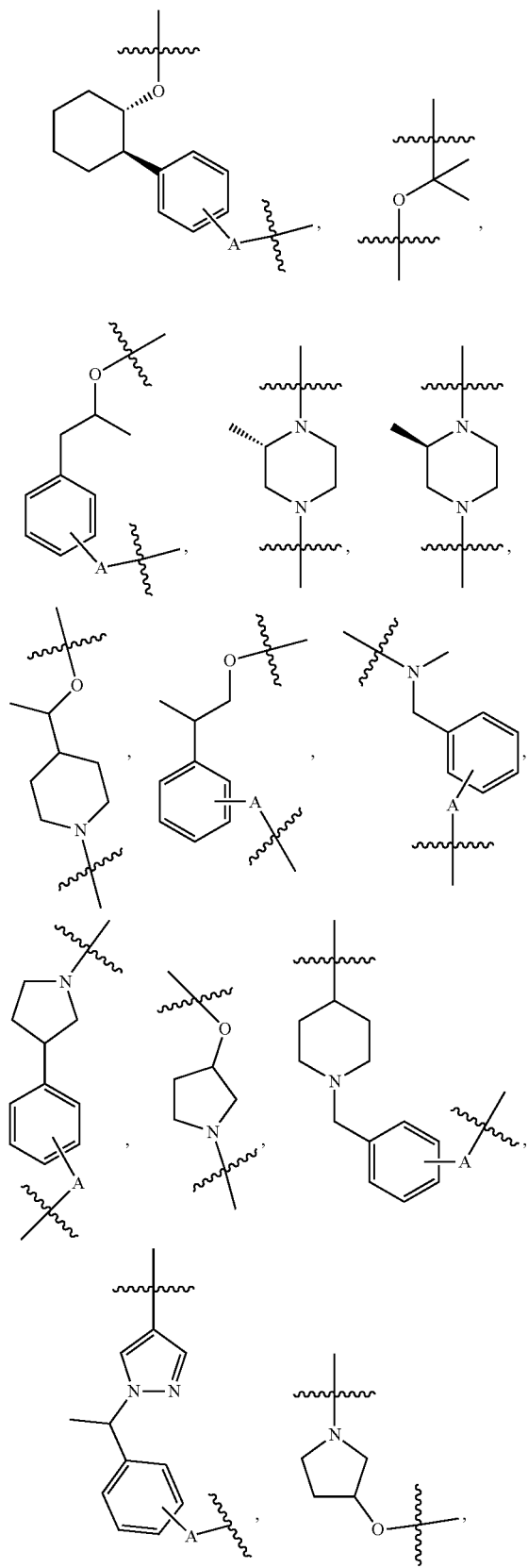
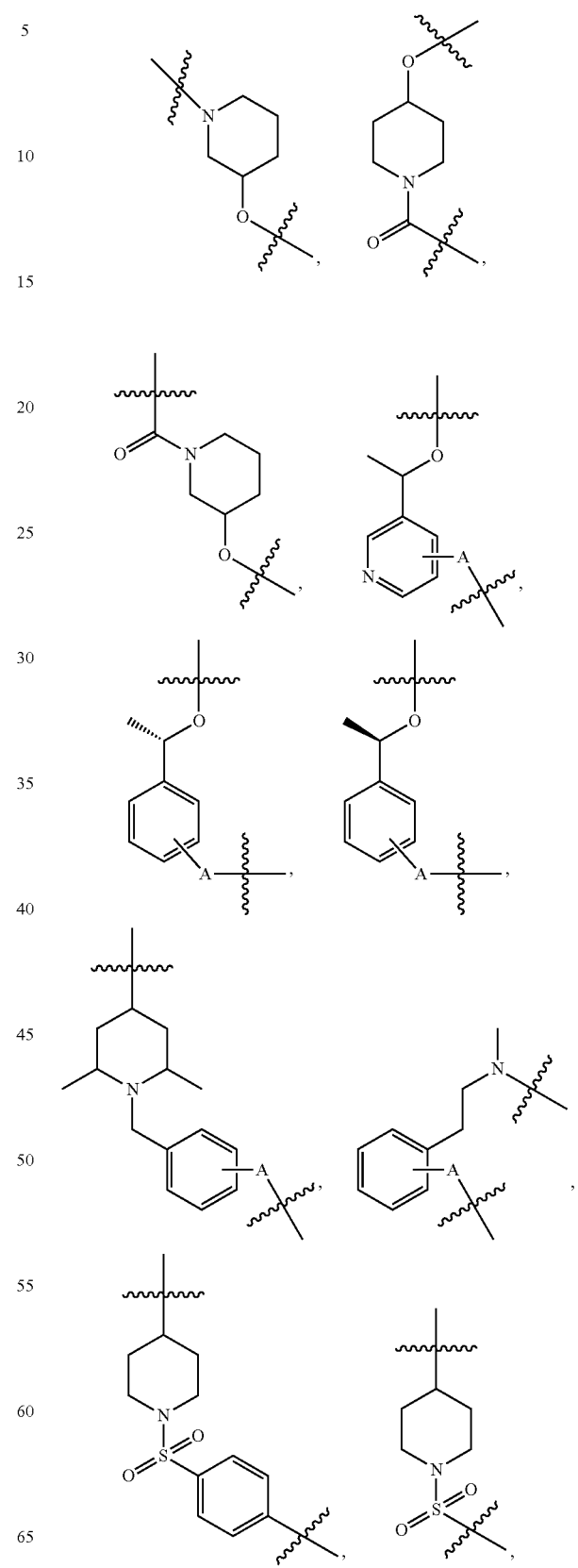

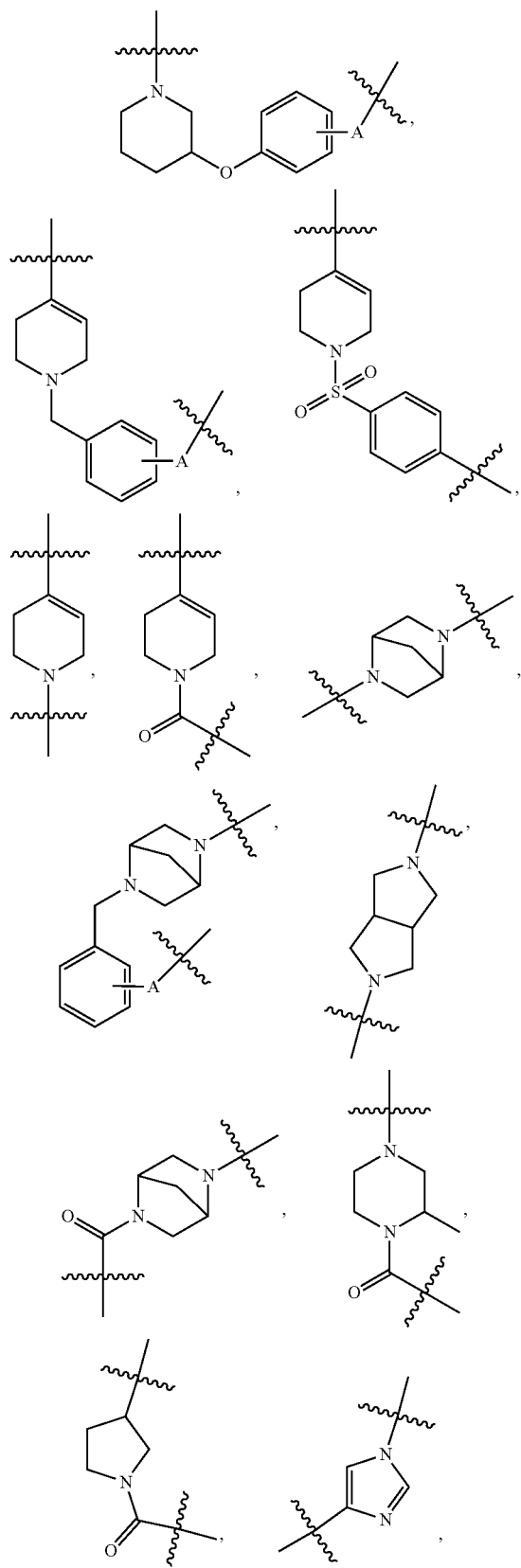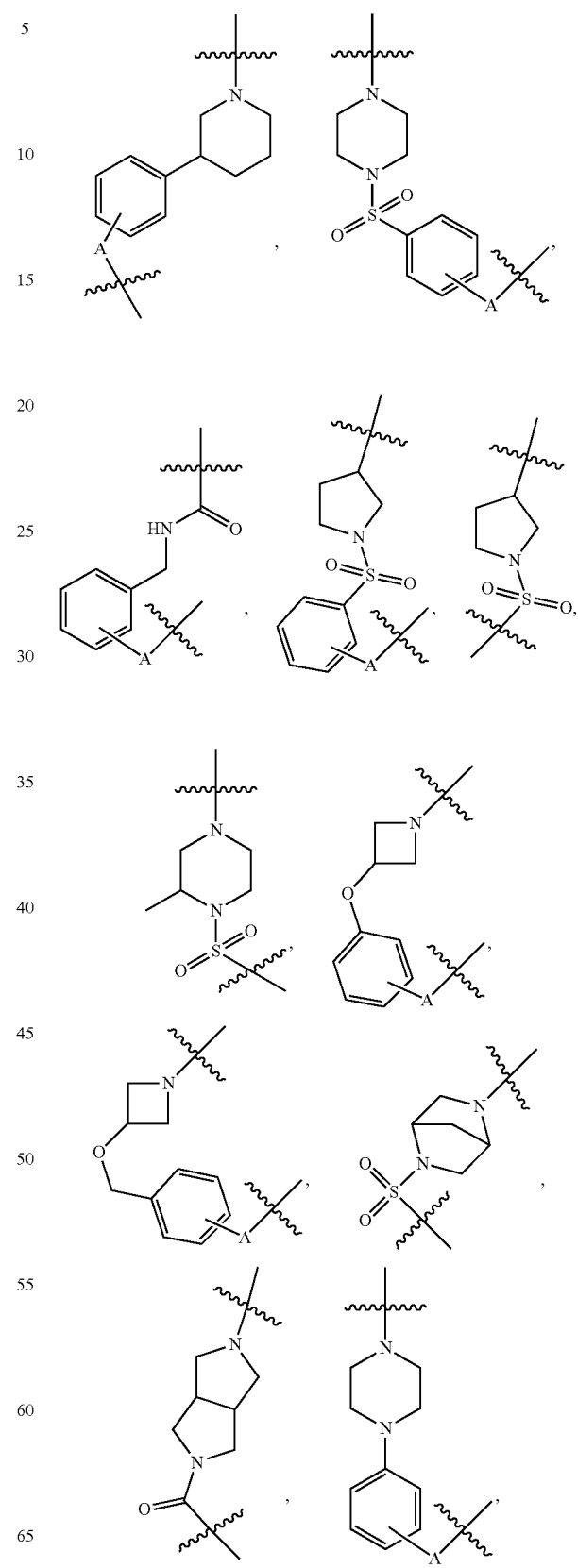

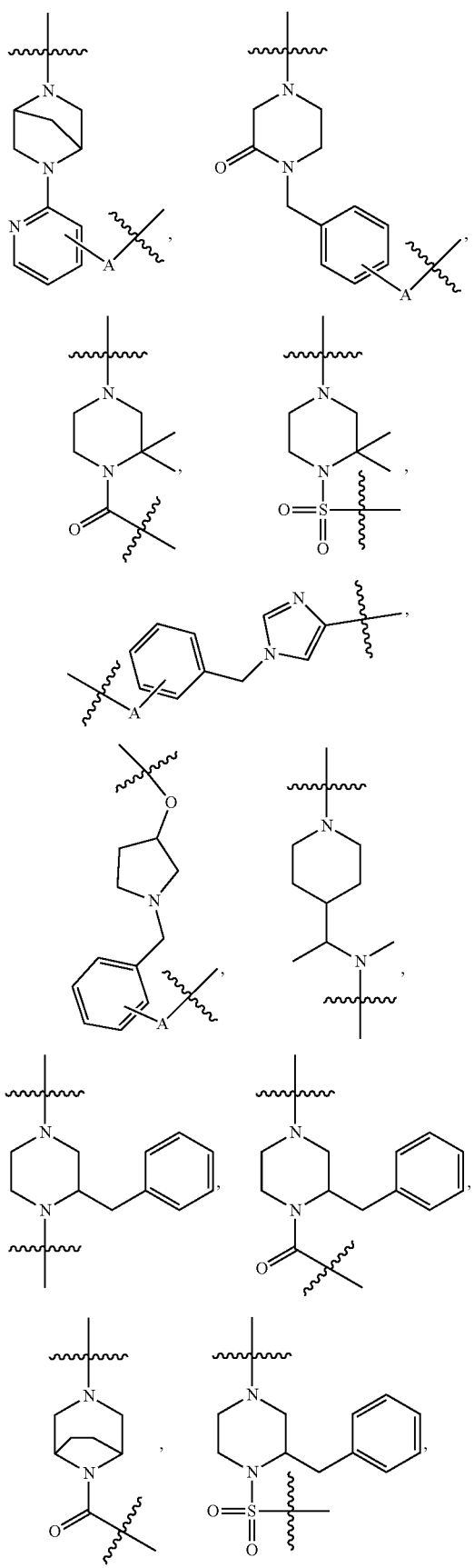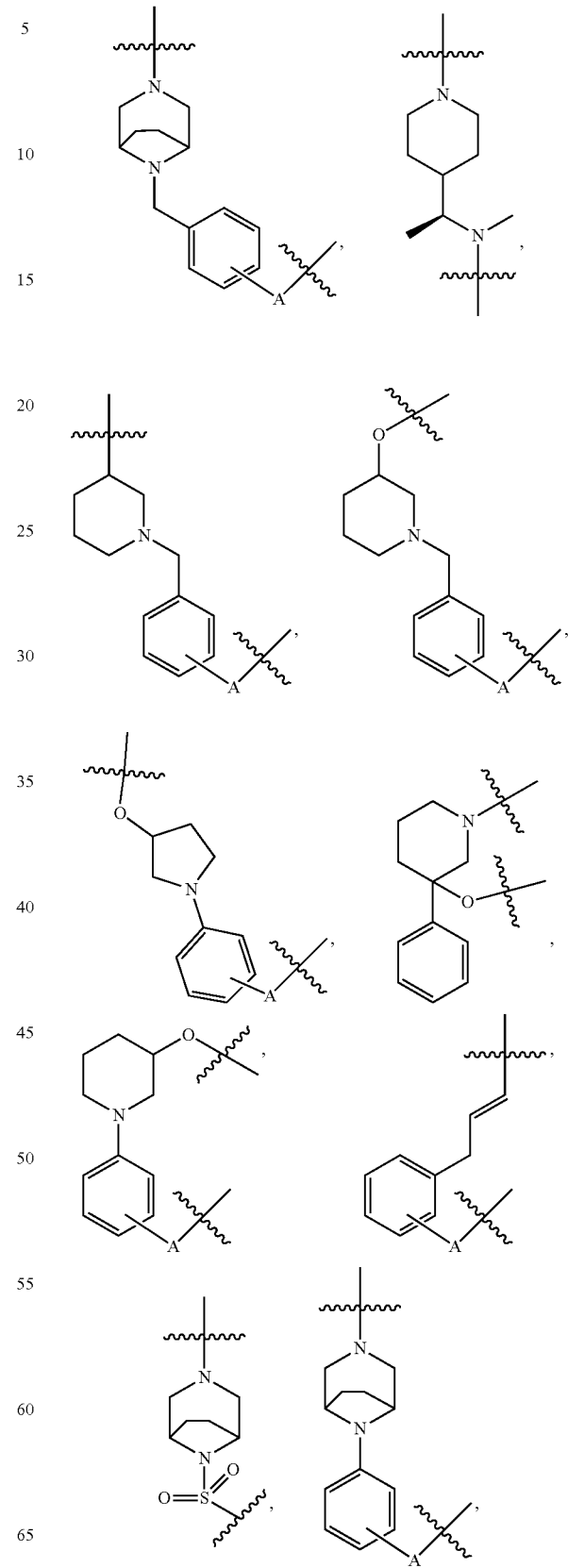

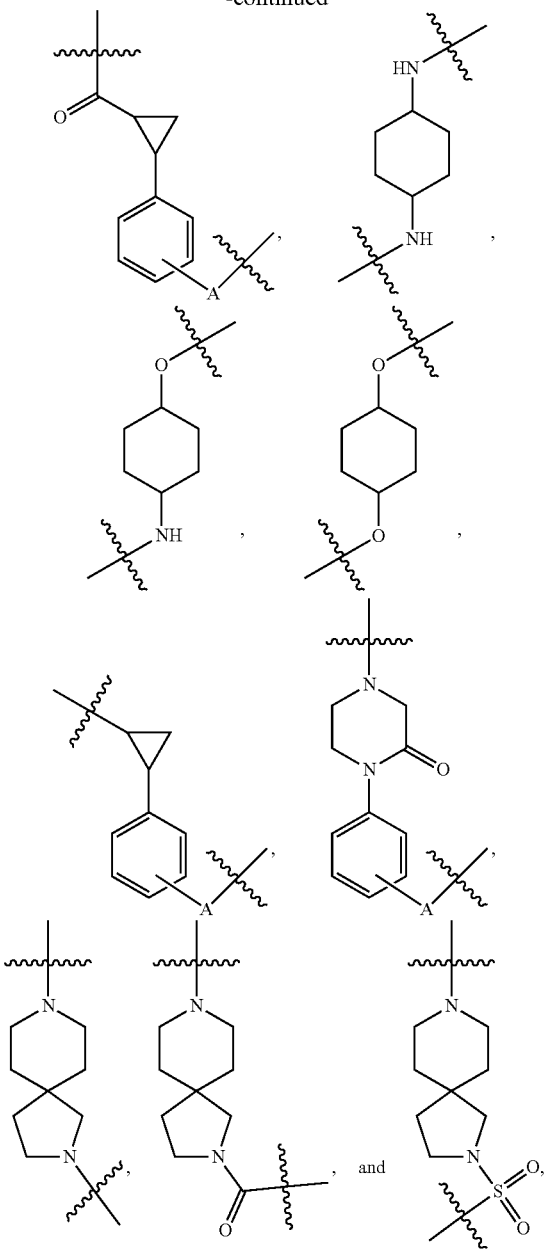

wherein A is any atom except H. For example, A is C, O, S, or N.

In some embodiments, $R^2$ is H, methyl, or acetyl; $R^3$ is H.

In some embodiments $R^2$ is H; and $R^3$ is H.

In some embodiments, $R^4$ is 2-hydroxy phenyl that is optionally substituted with one or more halo groups, which may be the same or different.

In some embodiments, $R^4$ is 2-hydroxy phenyl that is optionally substituted with one or more fluoro groups.

In some embodiments, $R^4$ is 2-hydroxyphenyl, 3-fluoro-2-hydroxyphenyl, 4-fluoro-2-hydroxyphenyl, 5-fluoro2-hydroxyphenyl, or 3,5-difluoro-2-hydroxyphenyl.

Accordingly, in some embodiments, the bivalent compounds of the present invention have a structure represented by formula I-1:

(I-1)

or a pharmaceutically acceptable salt or stereoisomer thereof.

In some embodiments, wherein the $R_1$ group is and the bivalent compounds of the present invention have a structure represented by formula I-1a:

(I-1a)

or a pharmaceutically acceptable salt or stereoisomer thereof.

Representative examples of yet other entities that may be suitable for use as PB1 targeting ligands in the bivalent compounds of the present invention are disclosed in U.S. Patent Application Publication 2018/0086720 A1, e.g., Paragraphs 71-83 therein.

Linkers

The linker ("L") provides covalent attachments for the targeting ligand and the degron. The structure of linker may not be critical, provided it does not substantially interfere with the activity of the targeting ligand or the degron. In some embodiments, the linker may be an alkylene chain that may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein $R^c$ is H or $C_1$-$C_6$ alkyl, wherein the interrupting and the one or both terminating groups may be the same or different.

In some embodiments, the linker may be a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N (R')—, —N(R')C(O)—, —N(R')C(O)N(R')—, —N(R')C(O) O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N (R')—, —N(R')S(O)—, —S(O)N(R')—, —N(R')S(O)$_2$N (R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chain:

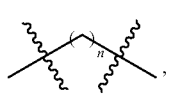

(L1)

wherein n is an integer of 1-10, inclusive, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10 examples of which include:

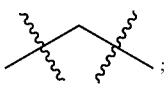

(L1-a)

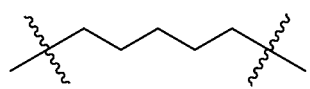

(L1-b)

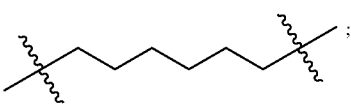

(L1-c)

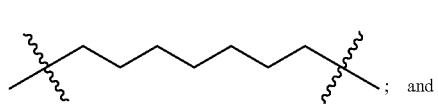

(L1-d)

; and

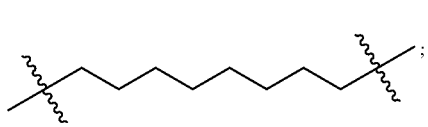

(L1-e)

alkylene chains terminating in various functional groups (as described above), examples of which are as follows:

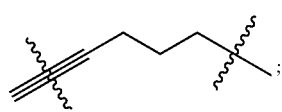

(L2-a)

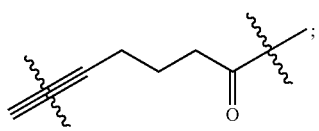

(L2-b)

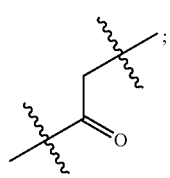

(L2-c)

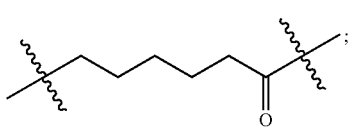

(L2-d)

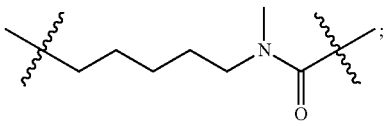

(L2-e)

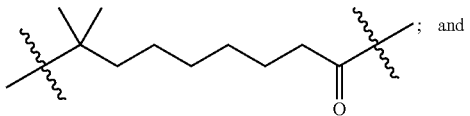

(L2-f)

; and

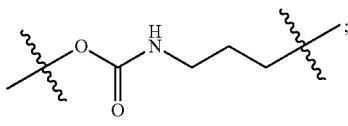

(L2-g)

alkylene chains interrupted with various functional groups (as described above), examples of which are as follows:

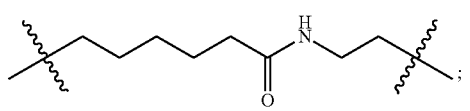

(L3-a)

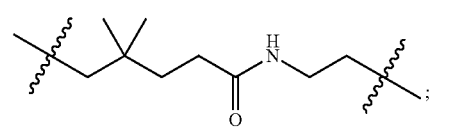

(L3-b)

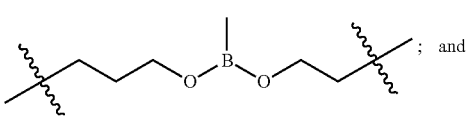

; and (L3-c)

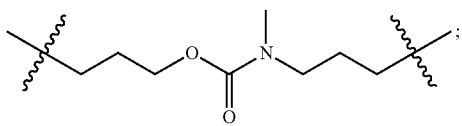(L3-d)

alkylene chains interrupted or terminating with heterocyclene groups, e.g.,

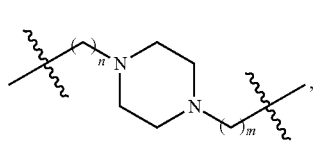(L4)

wherein m and n are independently integers of 0-10 examples of which include:

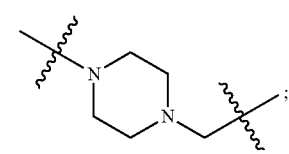(L4-a)

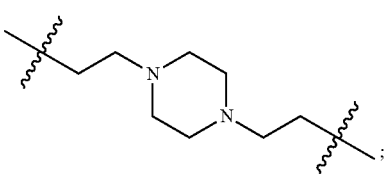(L4-b)

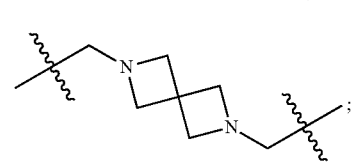(L4-c)

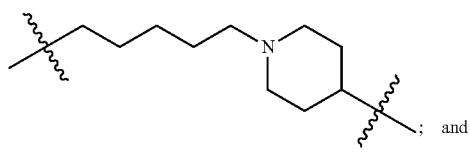(L4-d)

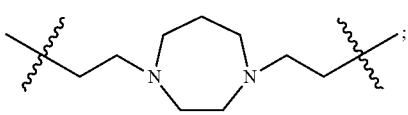(L4-e)

alkylene chains interrupted by amide, heterocyclene and/or aryl groups, examples of which include:

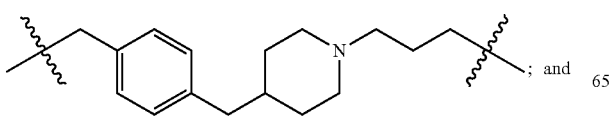(L5-a); and

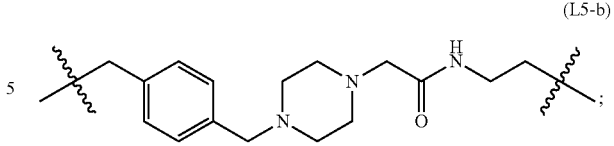(L5-b)

alkylene chains interrupted by heterocyclene and aryl groups, and a heteroatom, examples of which include:

(L6-a)

(L6-b); and

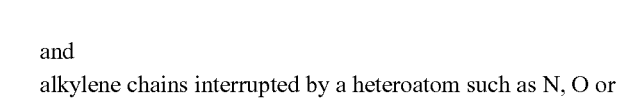(L6-c)

and alkylene chains interrupted by a heteroatom such as N, O or B, e.g.,

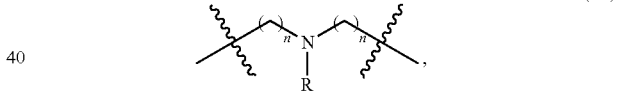(L7)

wherein n is an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7 8 9 and 10, and R is H, or C1 to C4 alkyl, an example of which is

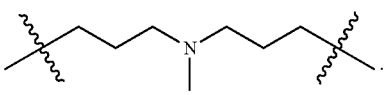(L7-a)

In some embodiments, the linker is a polyethylene glycol linker, examples of which include:

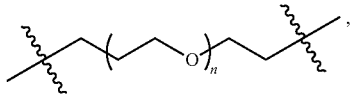(L8)

wherein n is an integer of 2-10, examples of which include:

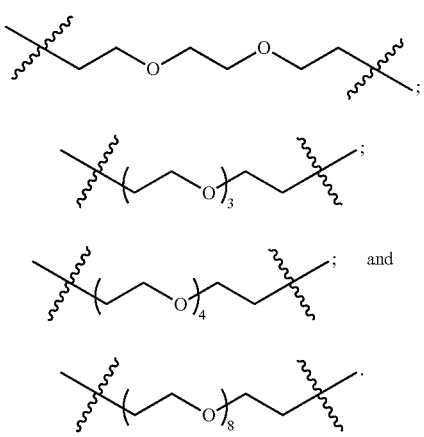

(L8-a); (L8-b); (L8-c); and (L8-d).

In some embodiments, the polyethylene glycol linker may terminate in a functional group, examples of which are as follows:

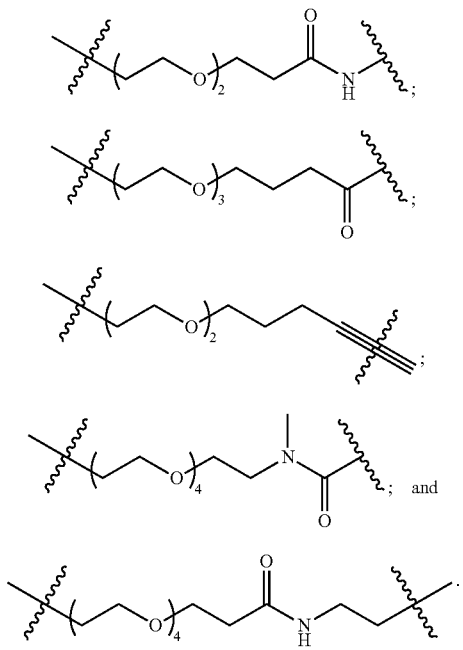

(L9-a); (L9-b); (L9-c); (L9-d); and (L9-e).

In some embodiments, bivalent compounds of the present invention may include TL-1 linked to a degron via anyone of L1-L9. Representative examples of bivalent compounds include:

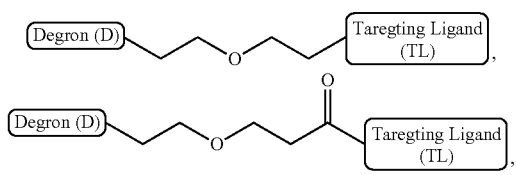

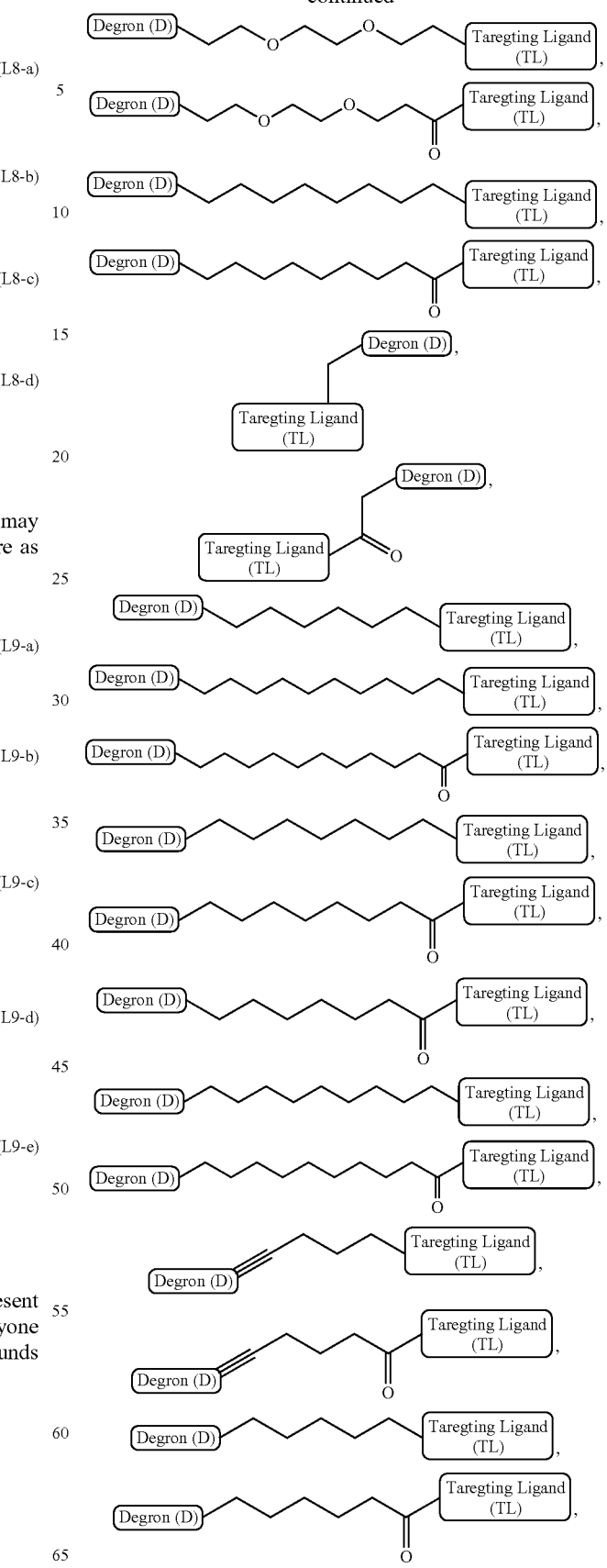

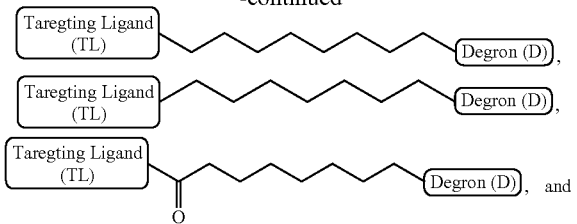
or a pharmaceutically acceptable salt or stereoisomer thereof.
In some embodiments, the bivalent compounds of the present invention have a structure represented by any of the following formulas (with the Degron shown generically):

-continued
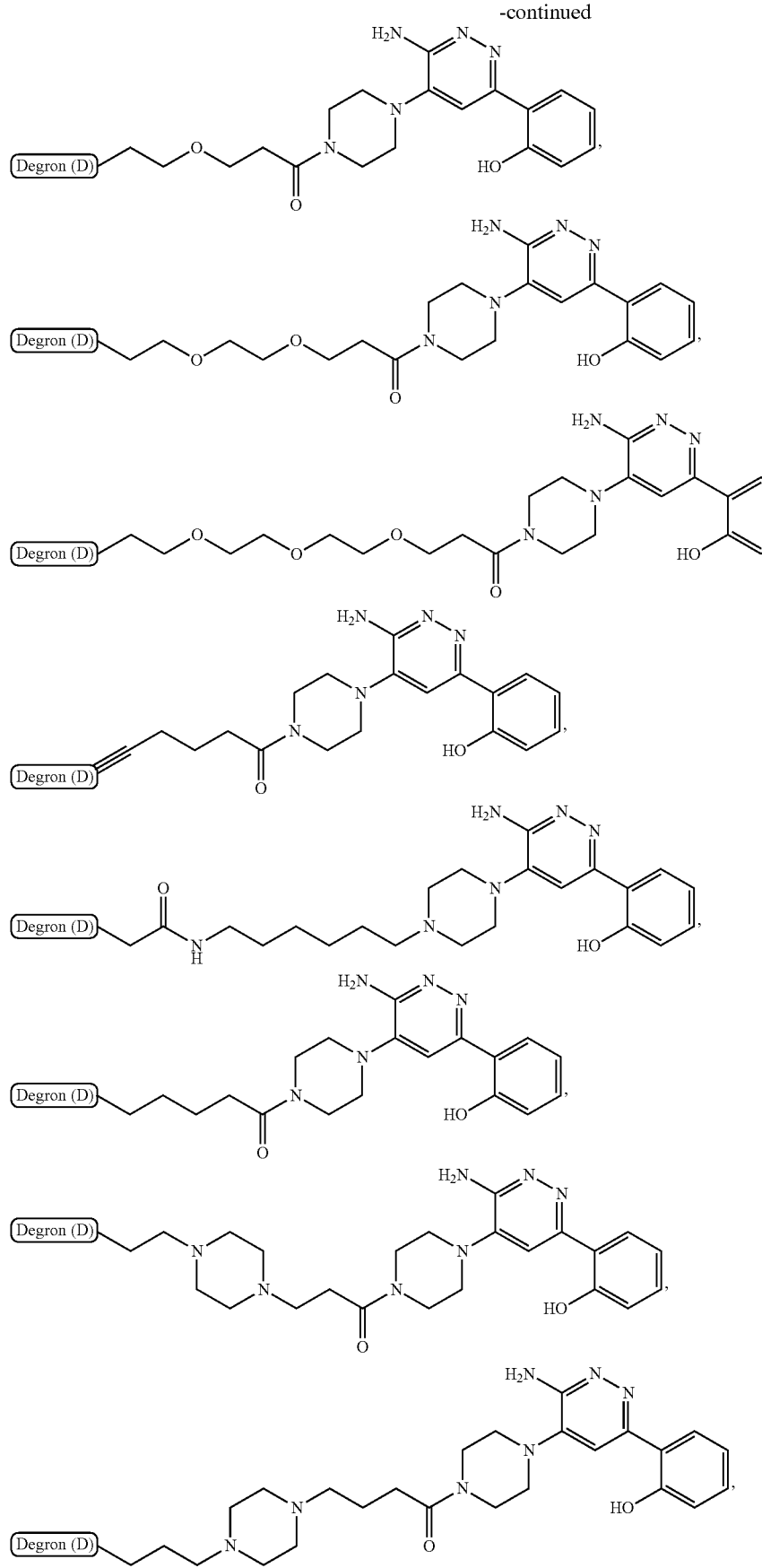

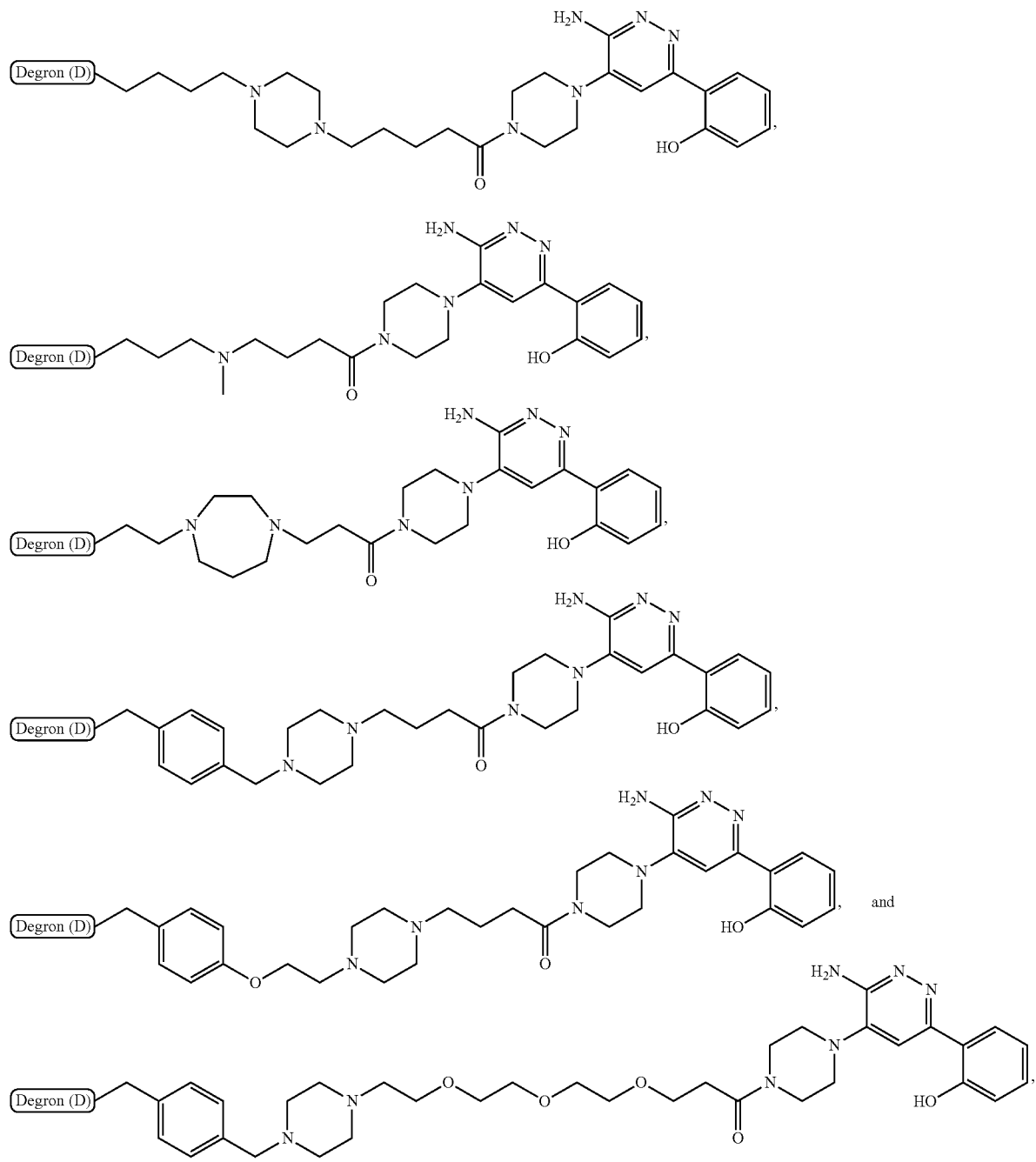

or a pharmaceutically acceptable salt or stereoisomer thereof.

Degrons

The Ubiquitin-Proteasome Pathway (UPP) is a critical cellular pathway that regulates key regulator proteins and degrades misfolded or abnormal proteins. UPP is central to multiple cellular processes. If defective or imbalanced, it leads to pathogenesis of a variety of diseases. The The degron, which constitutes one functional modality of the present bivalent compounds, binds an E3 ubiquitin ligase. The ligase catalyzes the covalent attachment of ubiquitin to the target protein, which in turn induces degradation of the target protein by native proteasomes. Thus, the bivalent compounds of the present invention are designed in a manner that exploits native cellular degradative processes but wherein the degradative action is homed to unwanted target proteins that are involved in disease etiology.

In some embodiments, the degron binds cereblon. Representative degrons that bind cereblon may be represented by Formula D1:

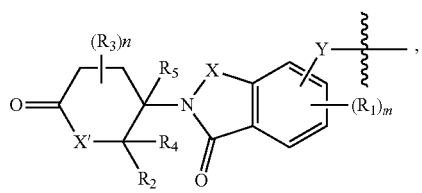
(D1)

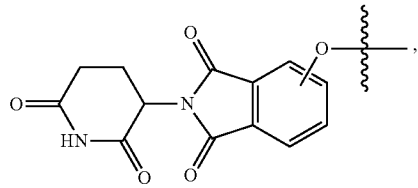
(D1c)

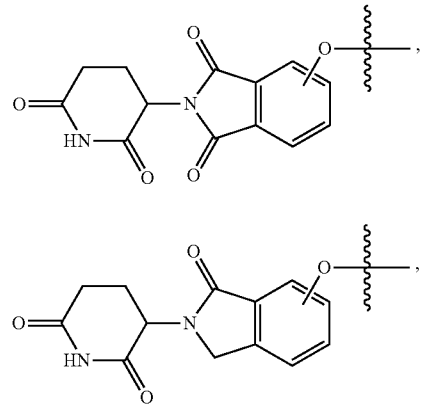
(D1d)

wherein
Y is a bond, C, N, O, S, $(CH_2)_{1-6}$, $(CH_2)_{0-6}$—O, $(CH_2)_{0-6}$—C(O)NR$_{2'}$, $(CH_2)_{0-6}$—NR$_2$C(O), $(CH_2)_{0-6}$—NH, or $(CH_2)_{0-6}$—NR$_2$;
X is C(O) or C(R$_6$)$_2$;
X' is NH, or CH$_2$;
each R$^1$ is independently halogen, OH, C1-C6 alkyl, or C1-C6 alkoxy;
each R$_3$ is independently H or C1-C3 alkyl;
each R$_2$ is independently H or C1-C3 alkyl;
each R$_4$ is independently H or C1-C3 alkyl;
or R$_2$ and R$_4$, together with the carbon atom to which they are attached, form C(O), a C3-C6 carbocycle, or a 4-, 5-, or 6-membered heterocycle including 1 or 2 heteroatoms selected from N and O;
R$_5$ is H, deuterium, C1-C3 alkyl, F, or Cl;
R$_6$ is H or C1-C3 alkyl;
m is 0, 1, 2 or 3; and
n is 0, 1 or 2.

Thus, in some embodiments, the bivalent compounds of the present invention have a structure represented by formula I-D1:

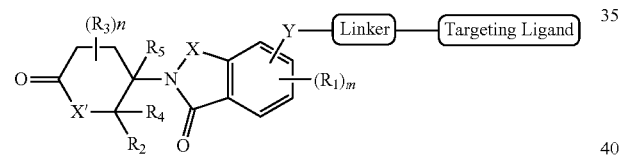

or a pharmaceutically acceptable salt, isotopic derivative or stereoisomer thereof, wherein X, X', Y, R$_1$, R$_2$, R$_3$, R$_4$, R$_5$, m and n are each as defined above, or a pharmaceutically acceptable salt or stereoisomer thereof.

Thus, in some embodiments, the bivalent compounds of this invention are represented by a formula selected from the group consisting of:

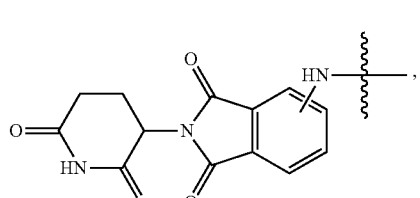
(D1a)

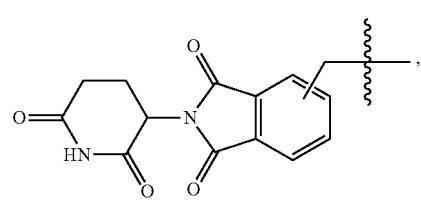
(D1e)

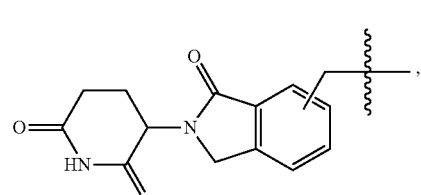
(D1f)

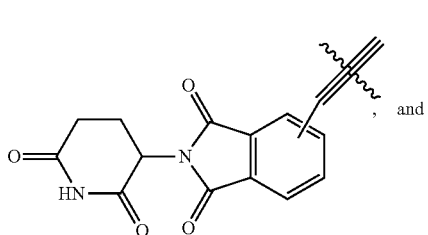
(D1g)
, and

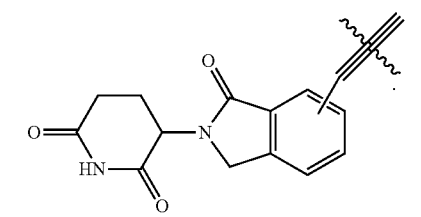
(D1h)
.

Thus, in some embodiments, the bivalent compounds of the present invention are represented by a formula selected from the group consisting of:

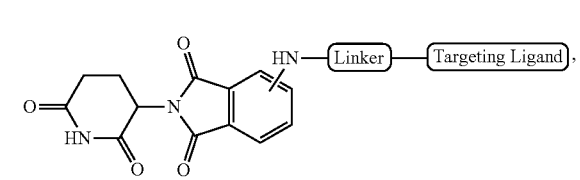

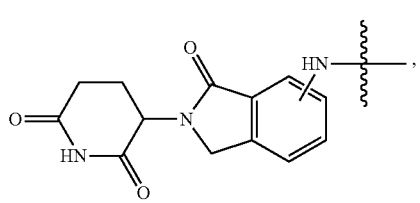
(D1b)

-continued

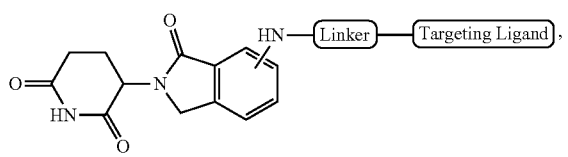

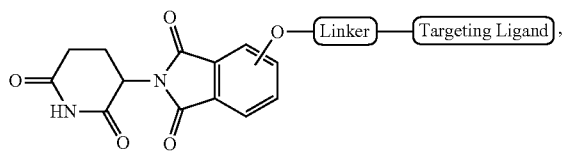

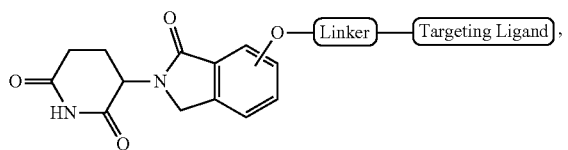

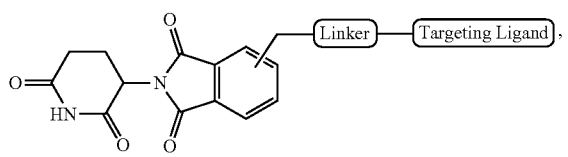

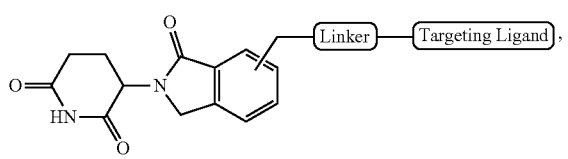

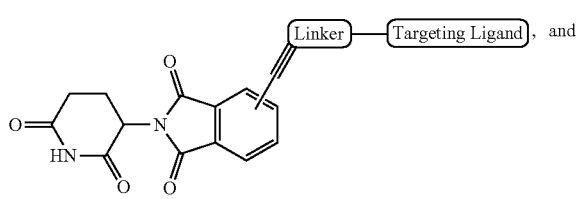, and

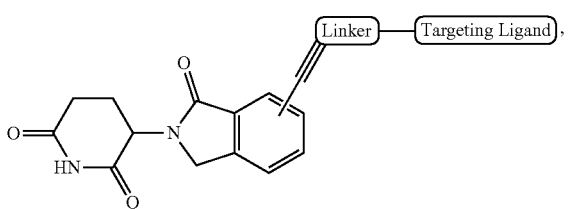, or a pharmaceutically acceptable salt, isotopic derivative or stereoisomer thereof.

Yet other degrons that bind cereblon and which may be suitable for use in the present invention are disclosed in U.S. Pat. No. 9,770,512, and U.S. Patent Application Publication Nos. 2018/0015087, 2018/0009779, 2016/0243247, 2016/0235731, 2016/0235730, and 2016/0176916, and International Patent Publications WO 2017/197055, WO 2017/197051, WO 2017/197036, WO 2017/197056 and WO 2017/197046.

In some embodiments, the E3 ubiquitin ligase that is bound by the degron is the von Hippel-Lindau (VHL) tumor suppressor. See, Iwai, et al., Proc. Nat'l. Acad. Sci. USA 96:12436-41(1999).

In some embodiments, the degrons that bind VHL are represented by the following formulas:

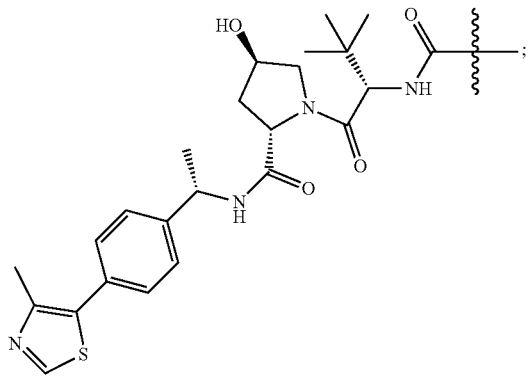

(D2)

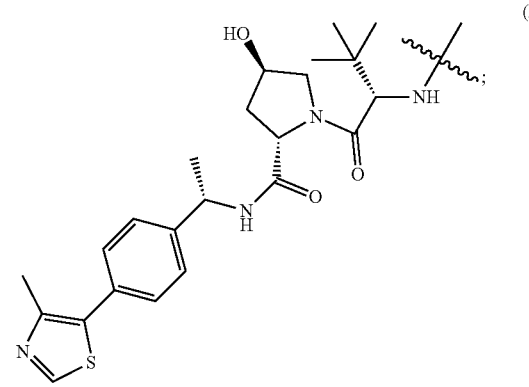

(D3)

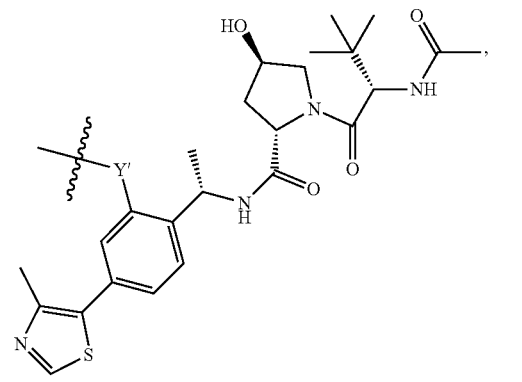

(D4)

wherein Y' is a bond, N, O or C;

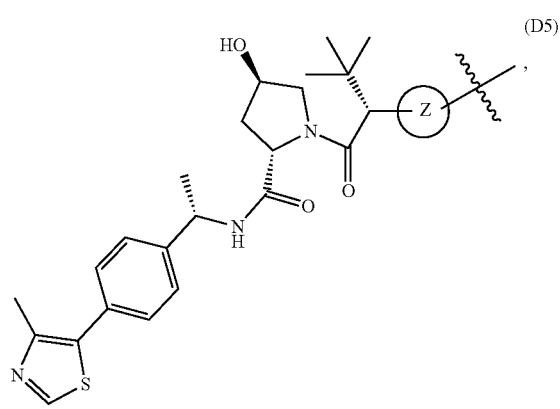

(D5)

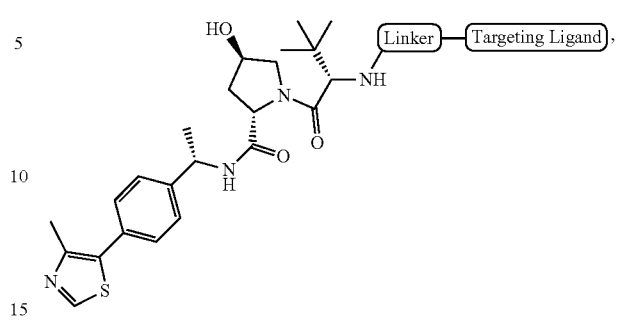

wherein Z is a cyclic group, which in some embodiments is a C5-6 carbocyclic or heterocyclic group. In certain embodiments, the cyclic group

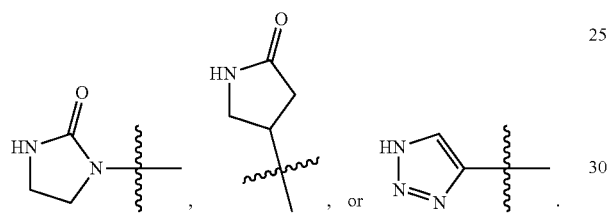

In some embodiments, the bivalent compounds of the present invention have a structure represented by any of the following formulas:

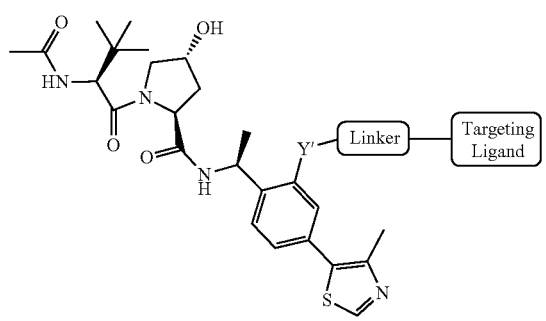

wherein Y' is a bond, N, O or C,

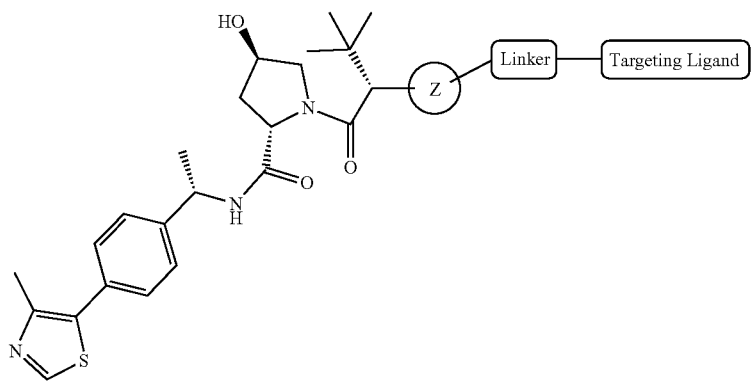

wherein Z is as defined above, or a pharmaceutically acceptable salt, isotopic isomer or stereoisomer thereof.

In some embodiments, the cyclic group is phenyl, pyrrolyl, furanyl, thiophenyl, pyrazolyl, imidazolyl, oxazolyl, thiazolyl, pyridinyl, pyridazinyl, pyrimidinyl, benzofuranyl, benzothiophenyl, indolyl, quinolinyl, or isoquinolinyl. In certain embodiments, the cyclic group is

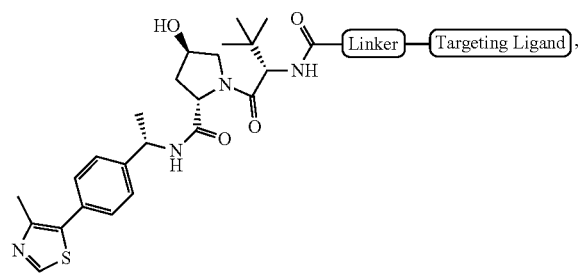

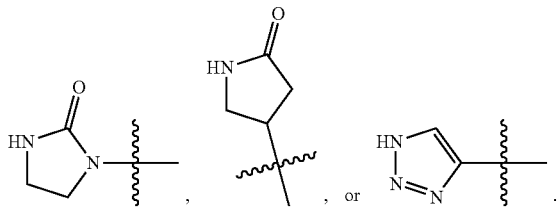 [SMILES: *N1CCNC1=O ; *C1CNC(=O)C1 ; *c1c[nH]nn1]

Yet other degrons that bind VHL and which may be suitable for use in the present invention are disclosed in U.S. Patent Application Publication 2017/0121321 A1. Further examples of degrons that may be suitable for use in the present invention are described in U.S. Patent Application Publication 2018/0015085 (e.g., the indolinones such as isoindolinones and isoindoline-1,3-diones embraced by formula IA ad IA' therein, the bridged cycloalkyl compounds embraced by formula IB and IB' therein).

Thus, in some embodiments, the bivalent compounds of the present invention have a structure represented by any structures generated by the combination of structures TL-1, L1 to L9, amd the structures of the degrons described herein, including D1 to D5, or a pharmaceutically acceptable salt or stereoisomer thereof.

Accordingly, in some embodiments, the bivalent compounds of the present invention have a structure represented the following formulas (wherein the PB1 targeting ligand is shown generically):

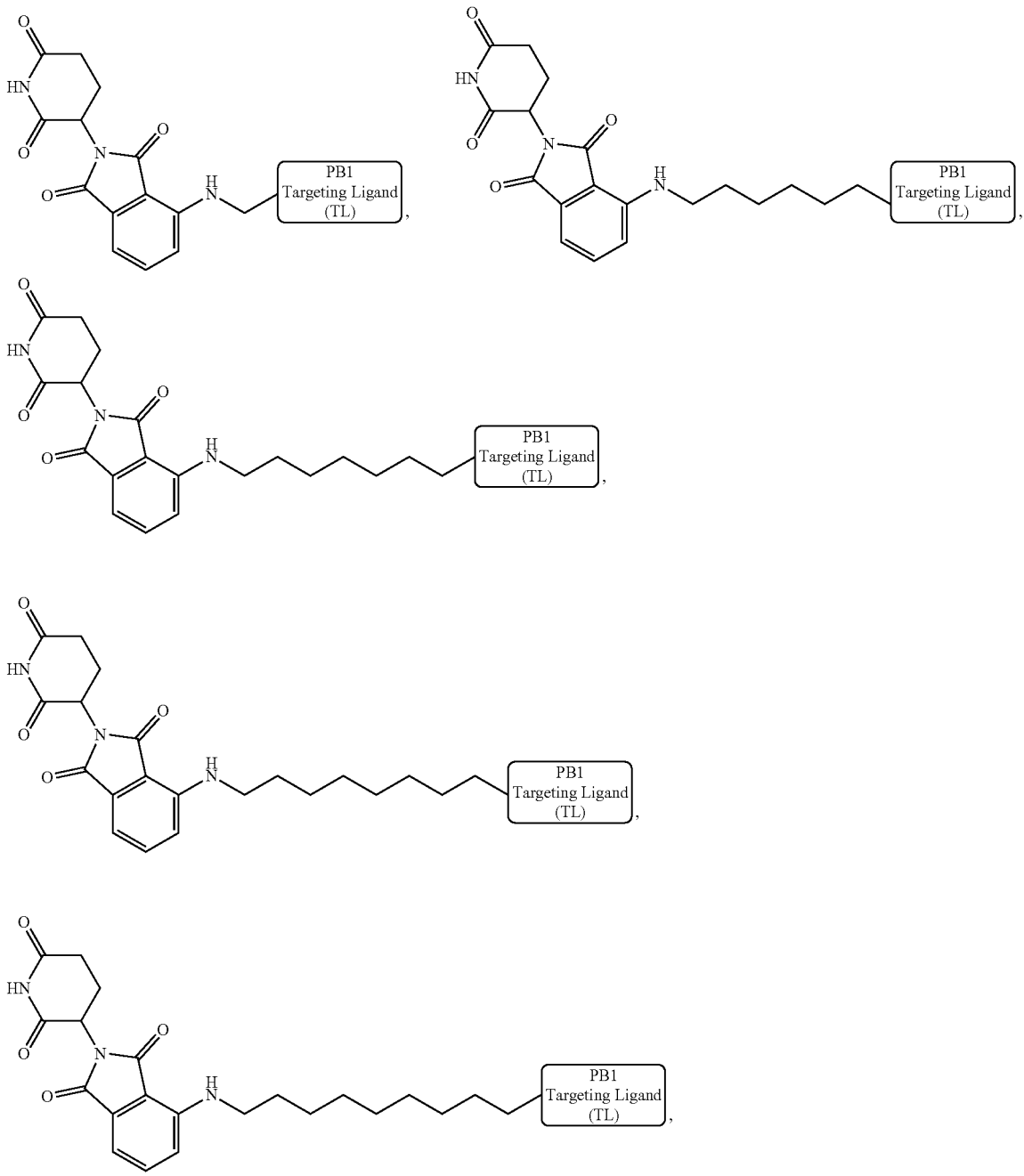

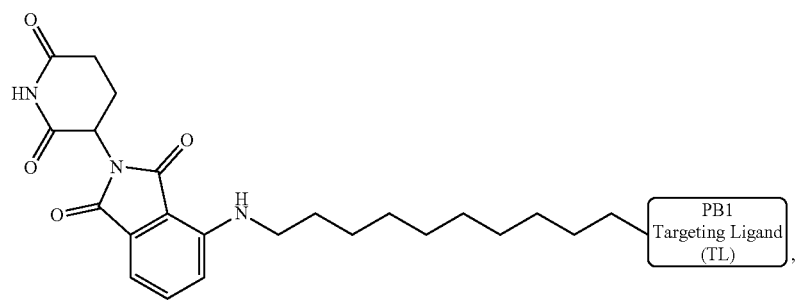
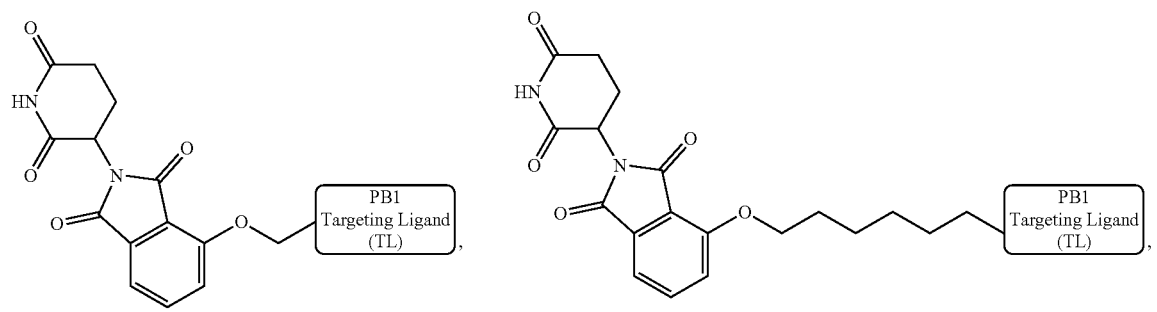
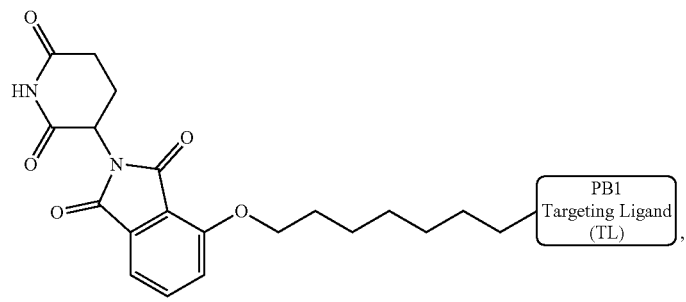
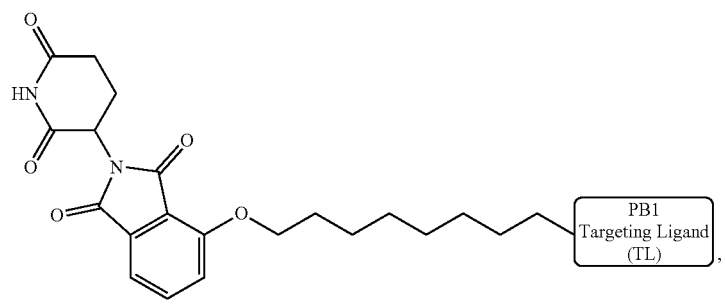
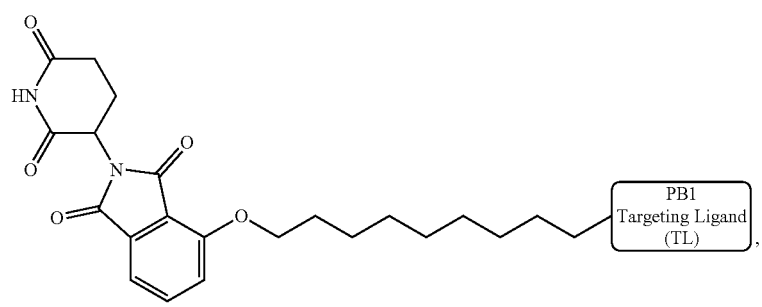

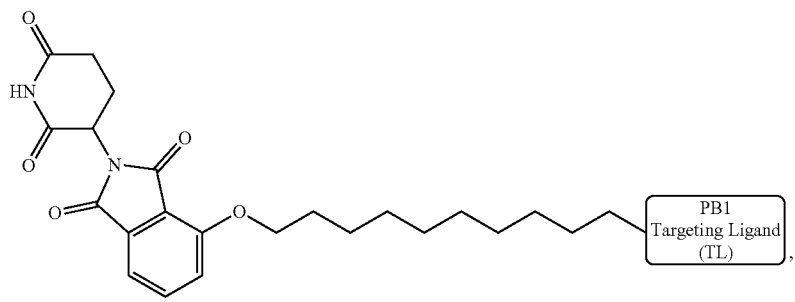
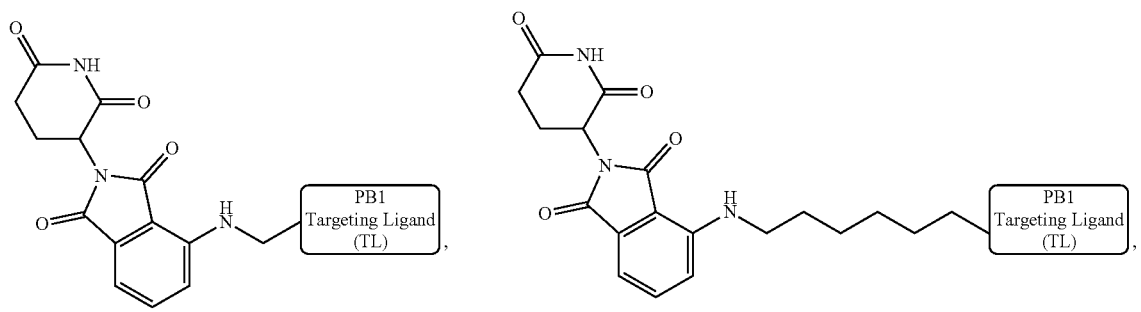
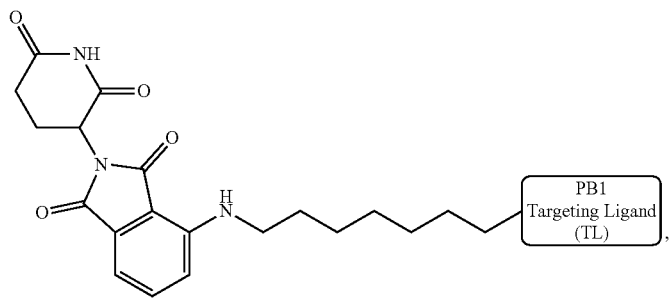
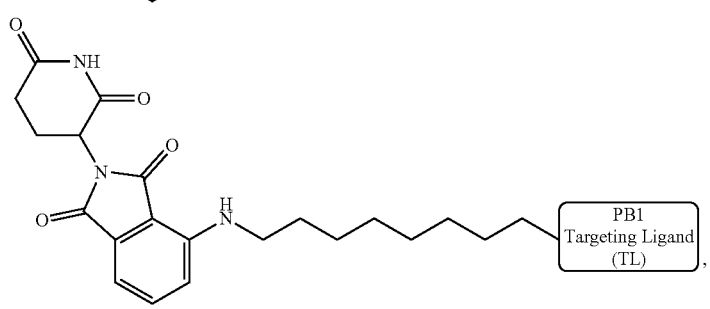
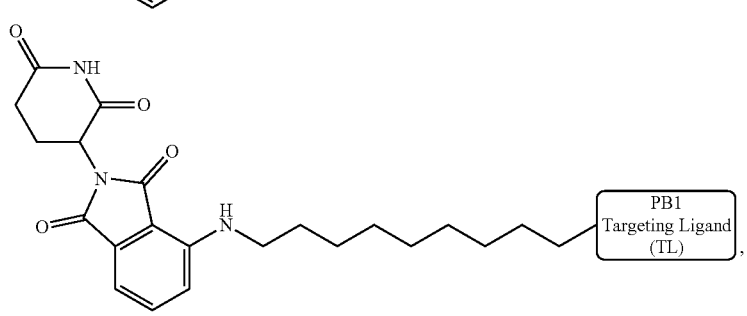

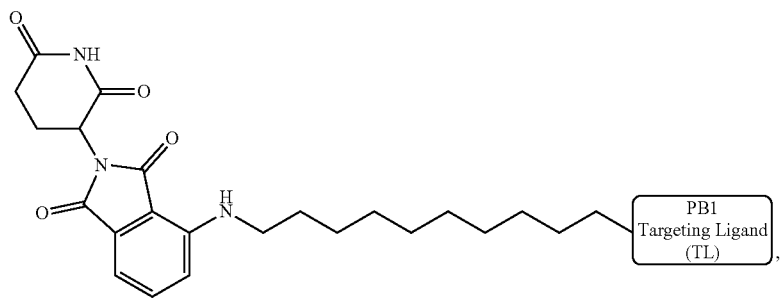
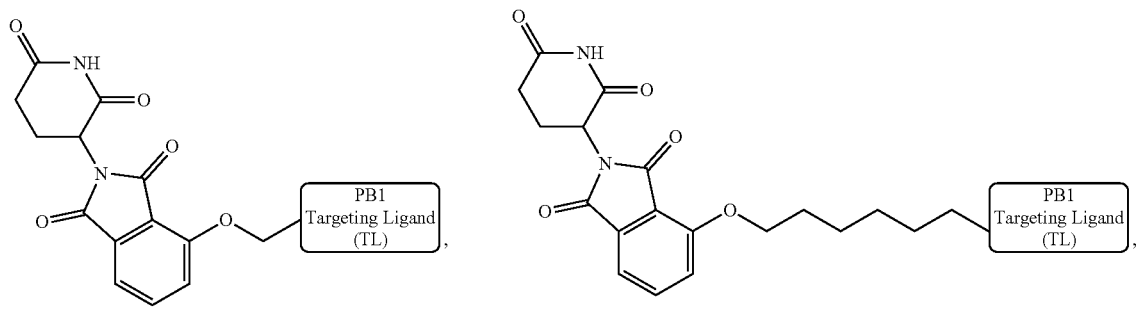
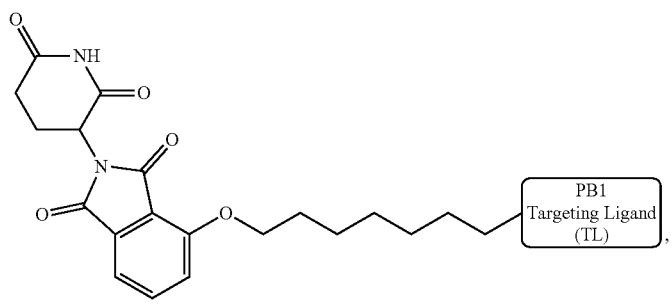
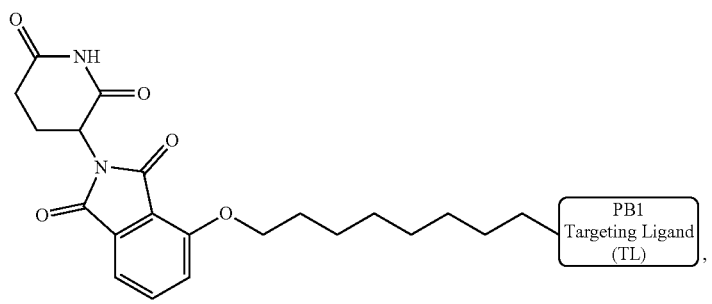
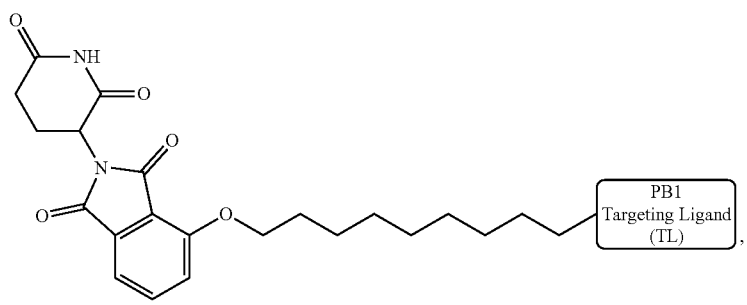

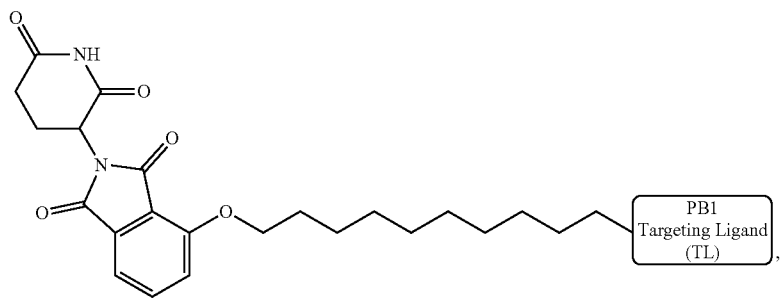
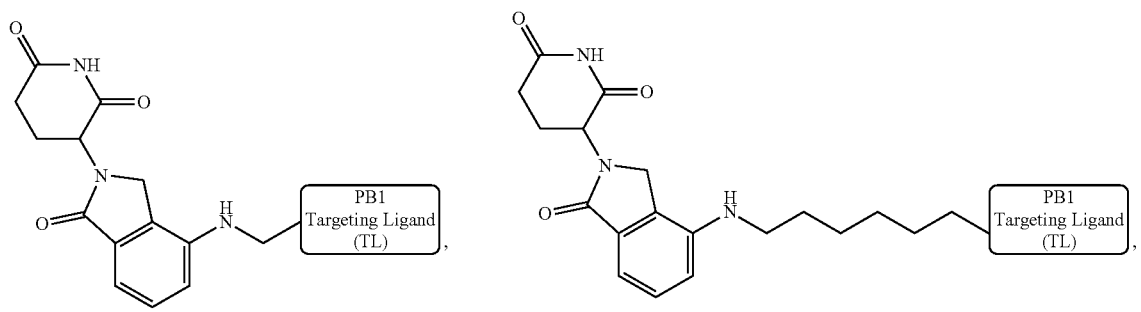
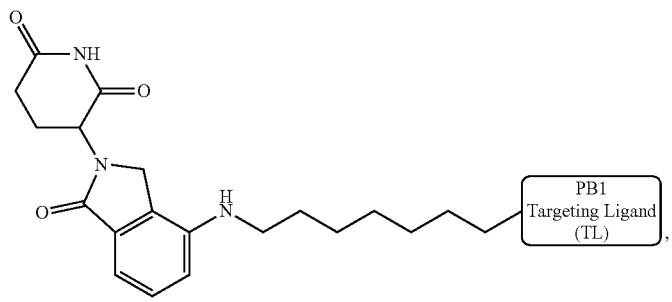
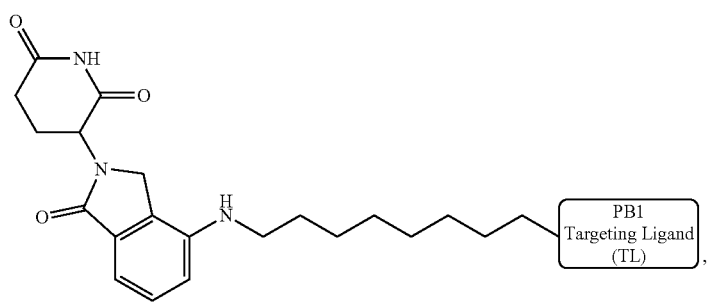
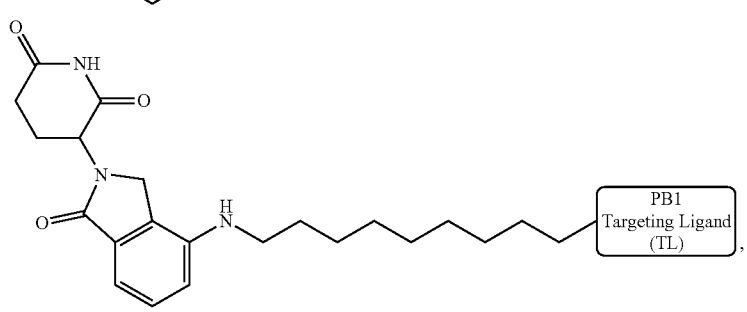

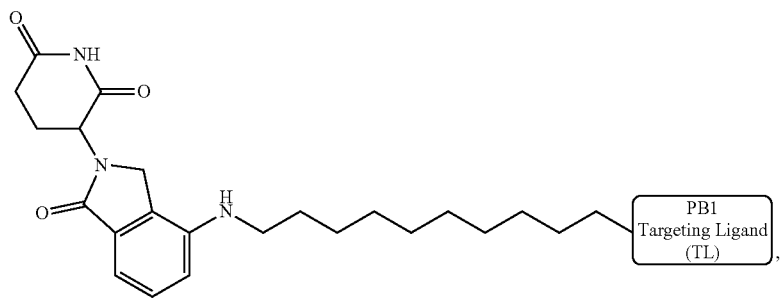
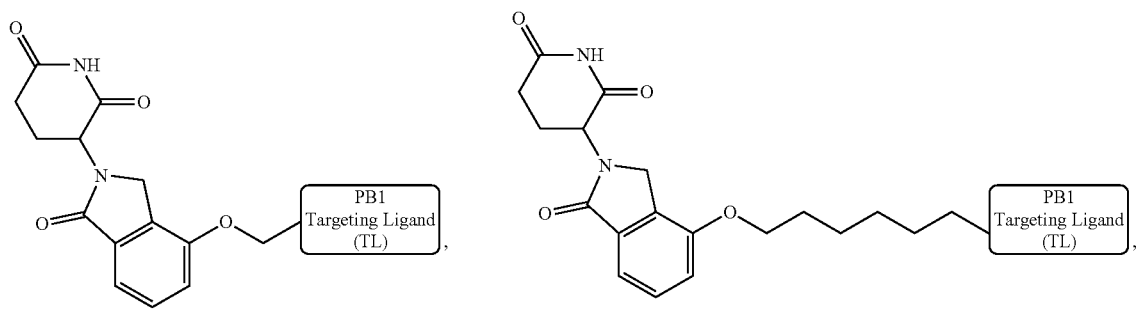
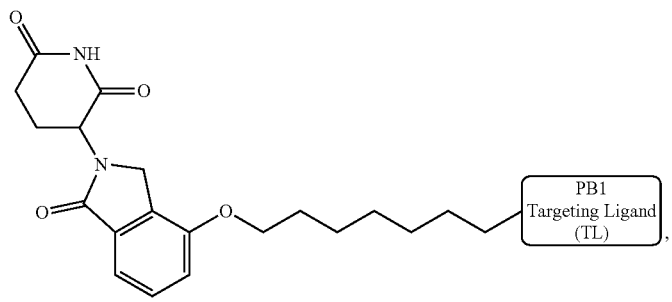
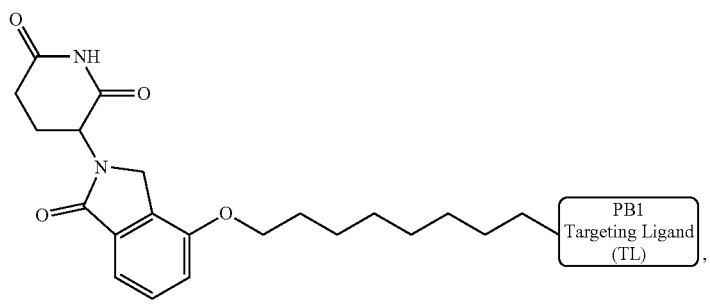
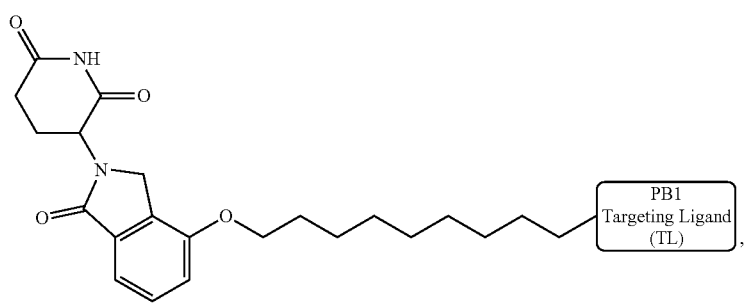

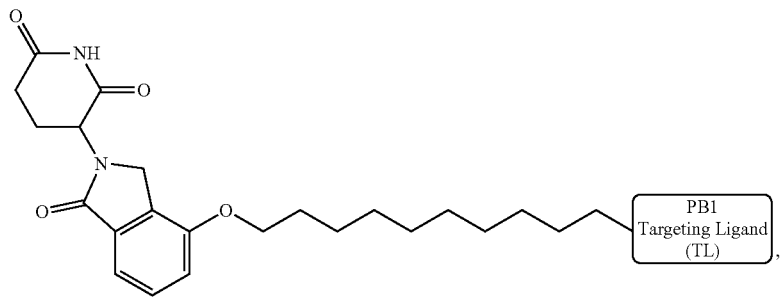
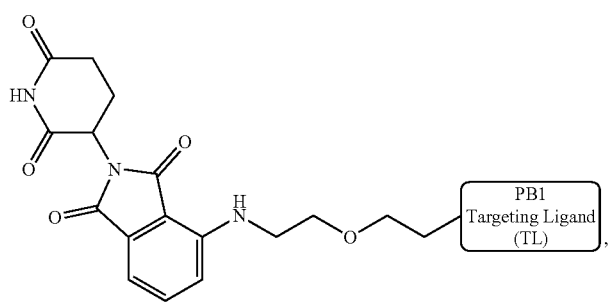
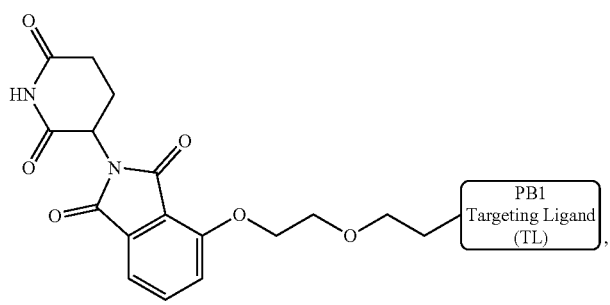
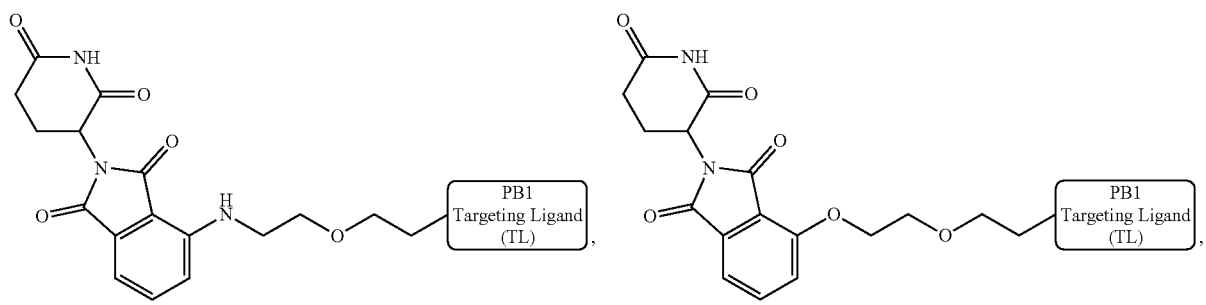
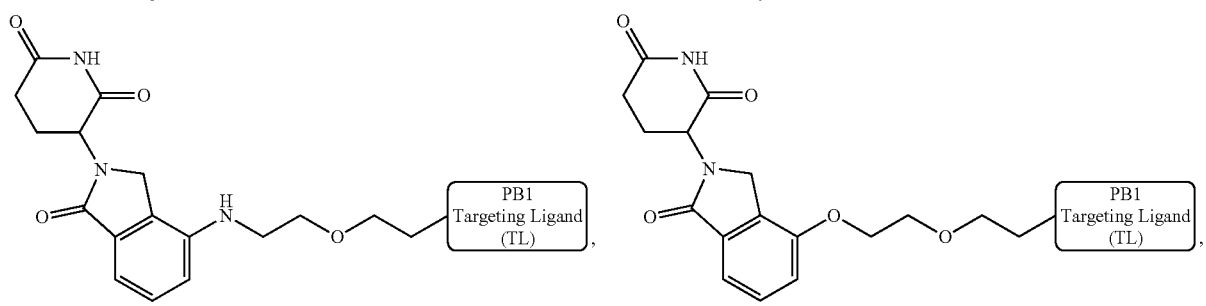

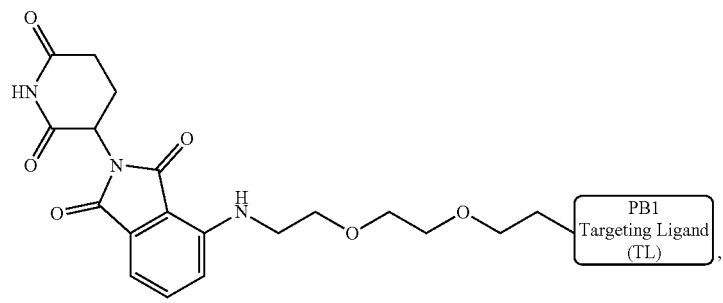
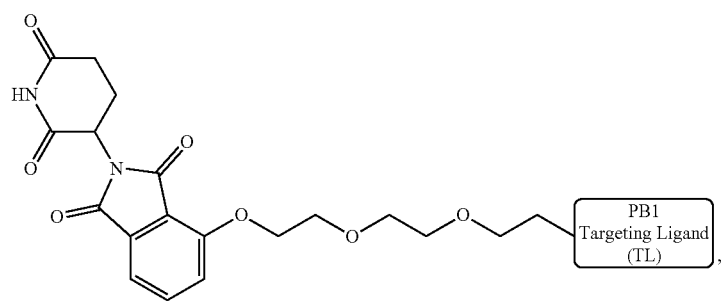
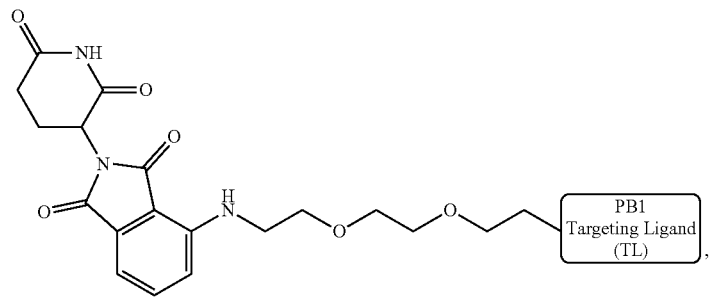
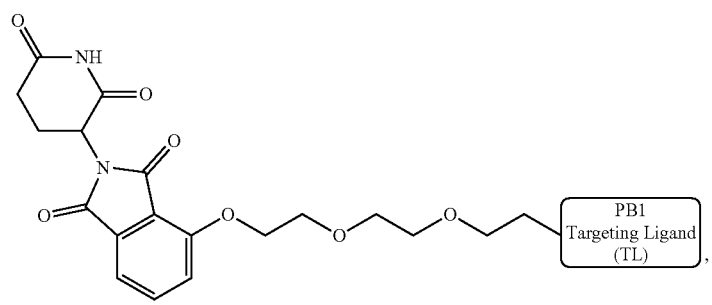
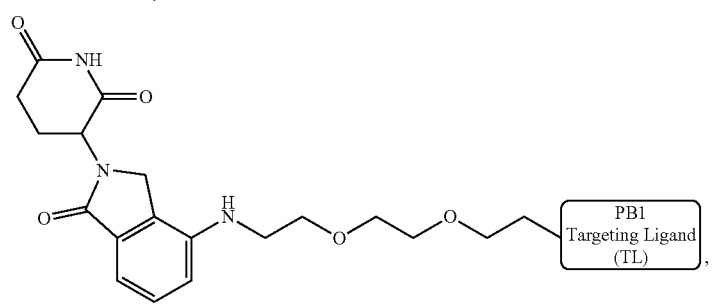

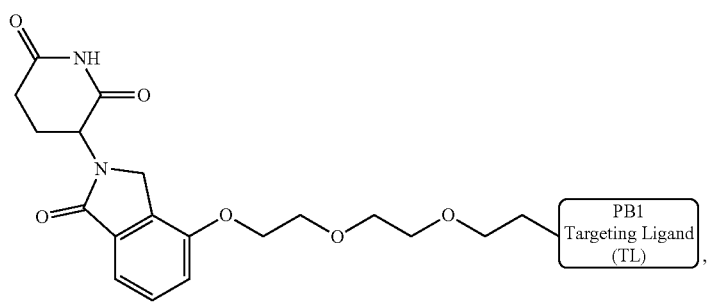
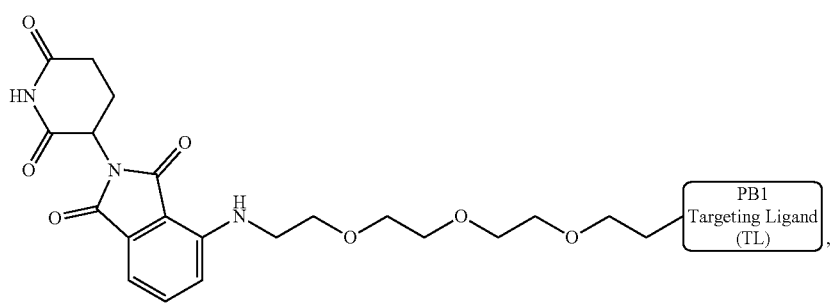
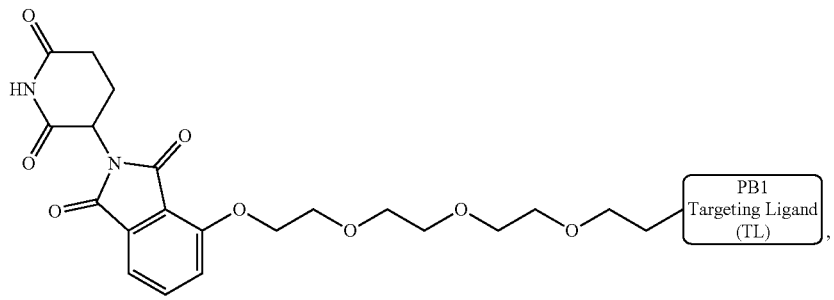
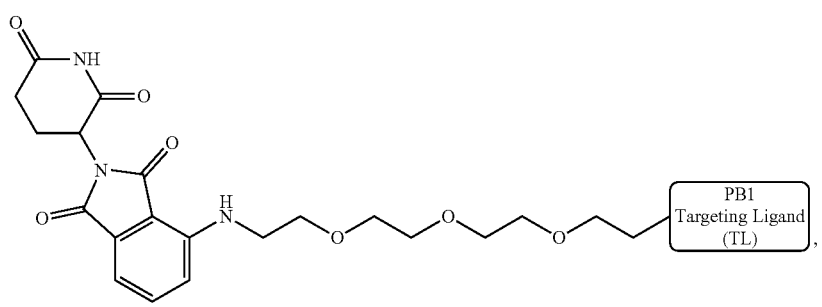
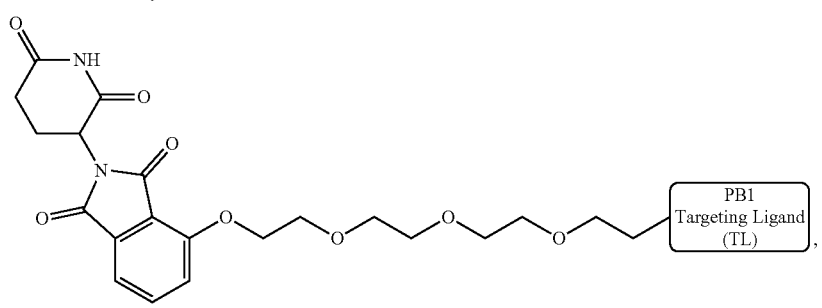

-continued
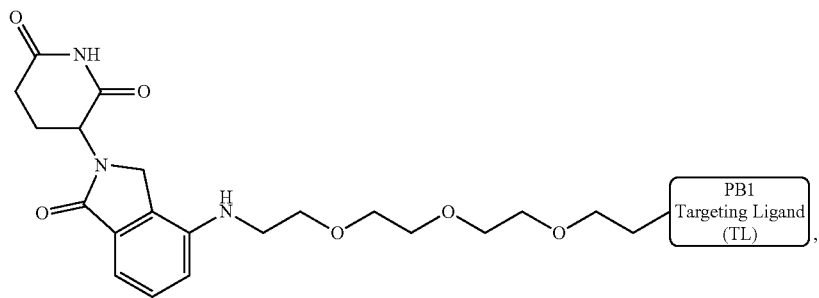
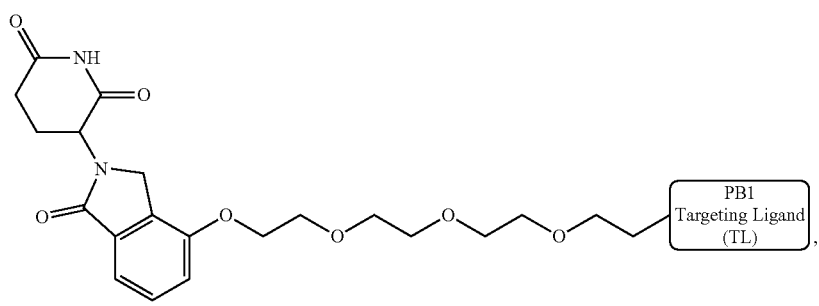
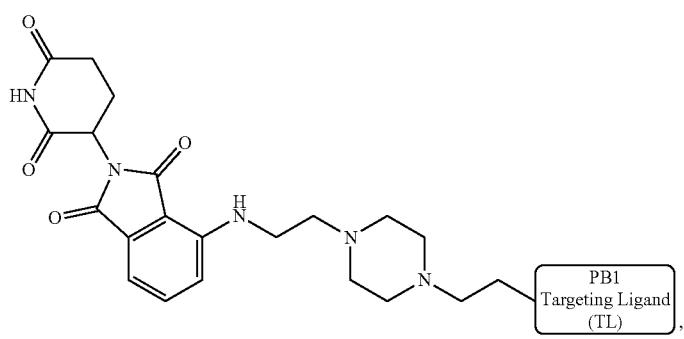
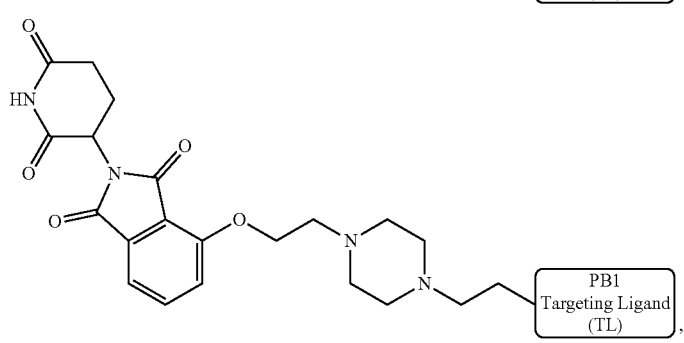
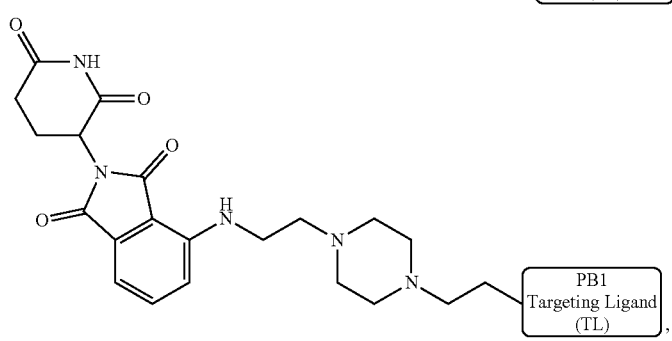

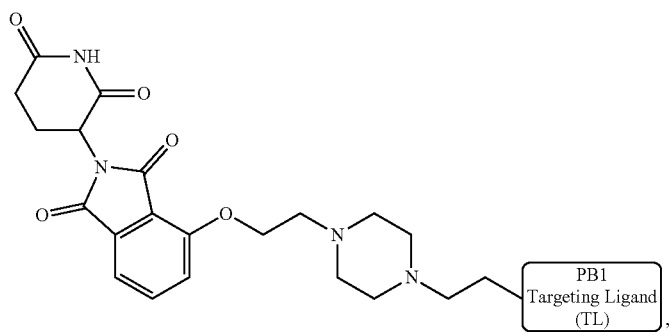
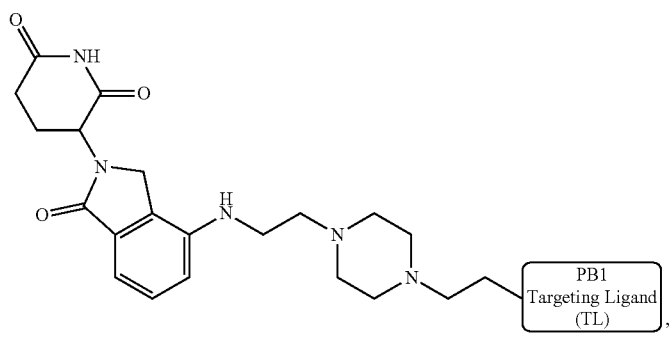
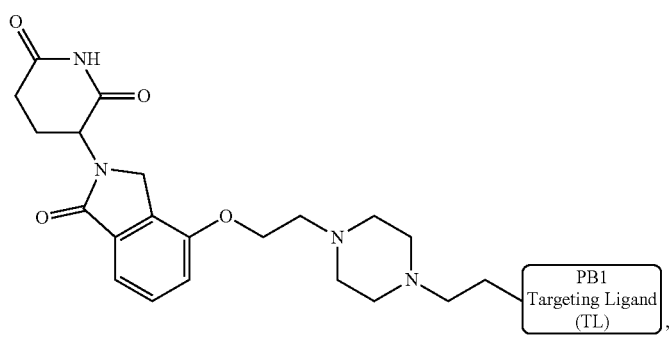
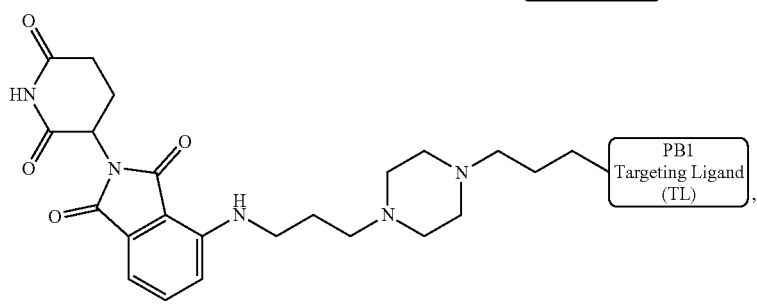
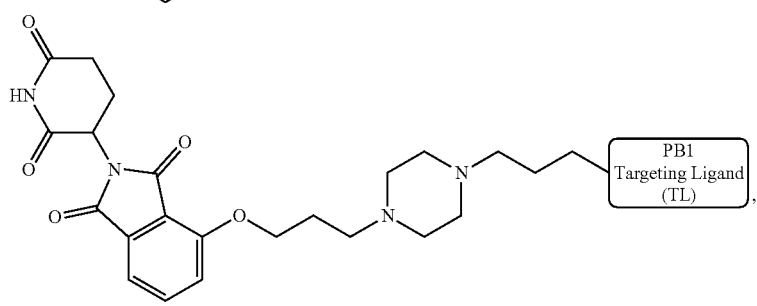

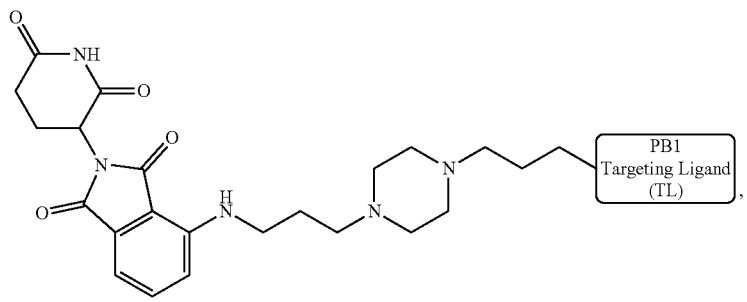
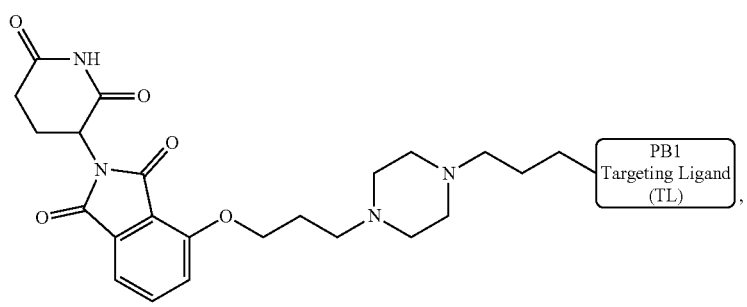
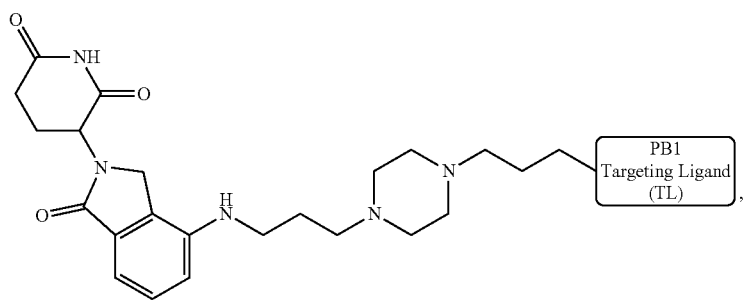
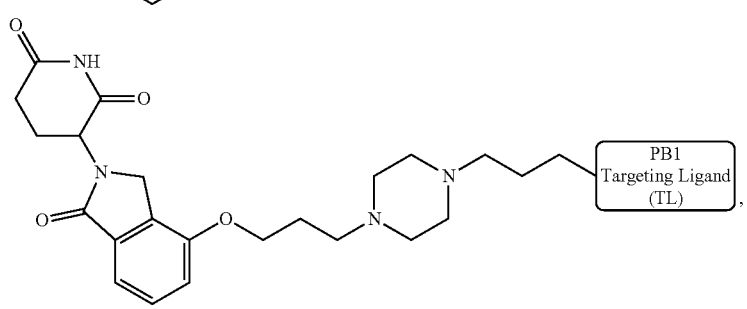
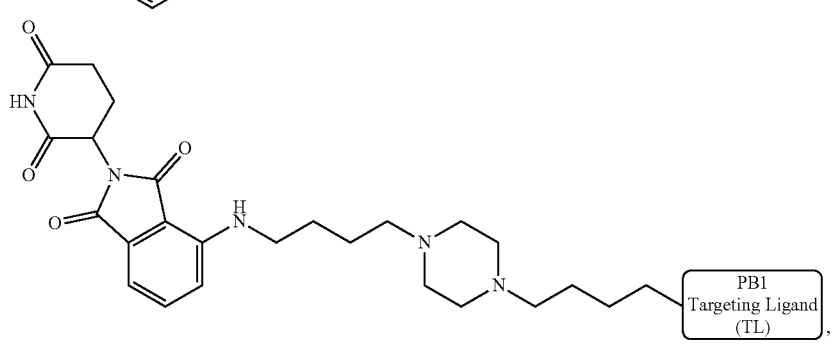

-continued
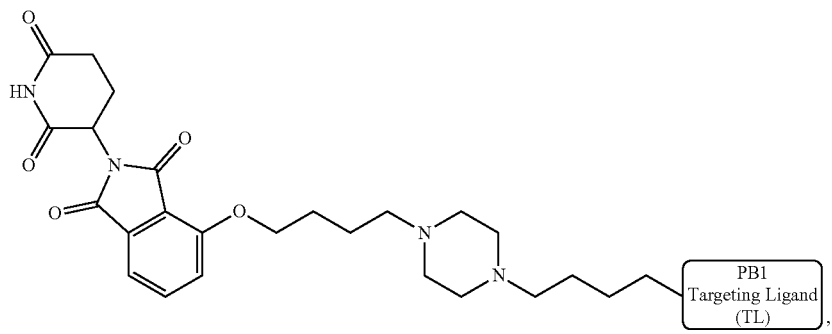
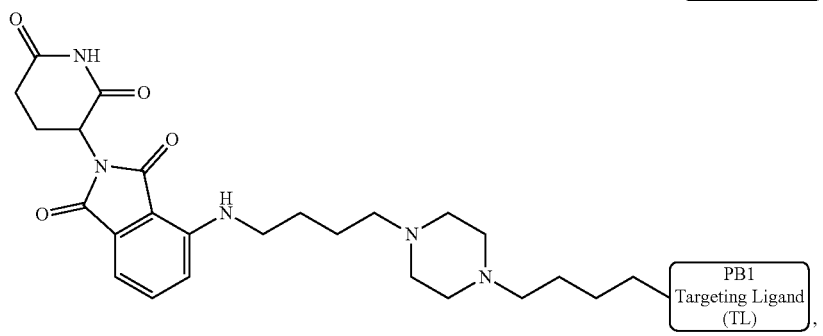
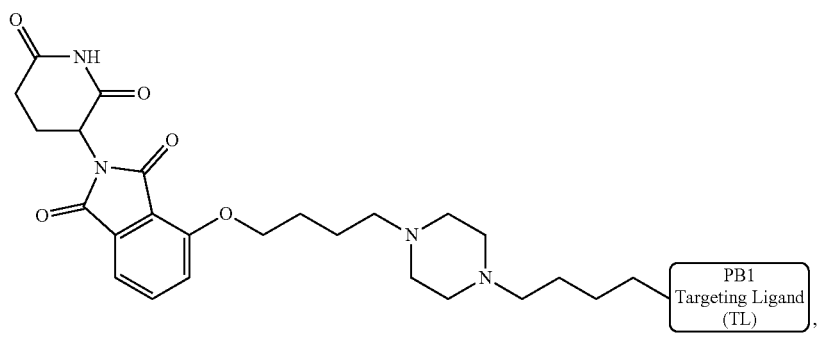
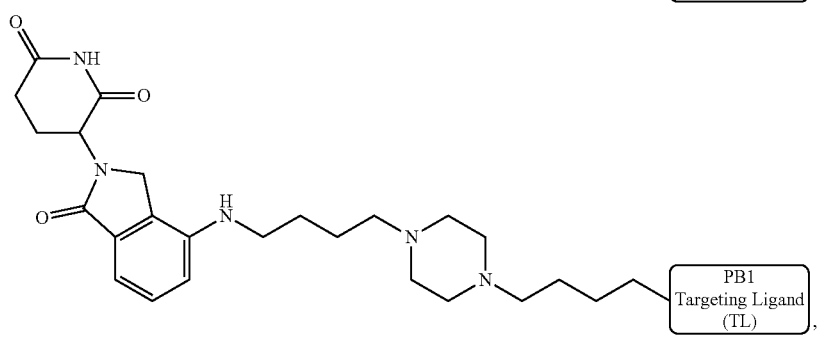
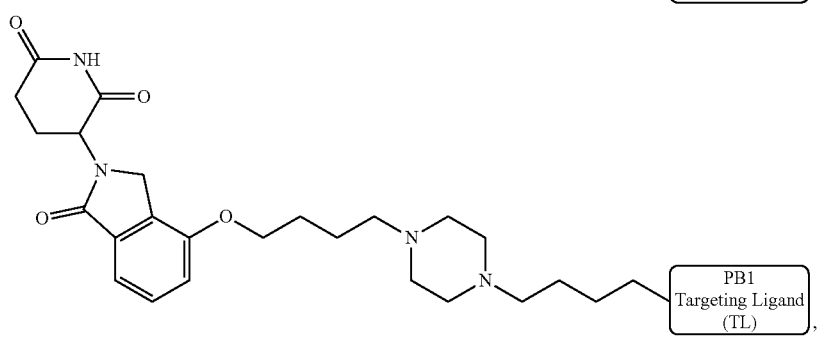

-continued
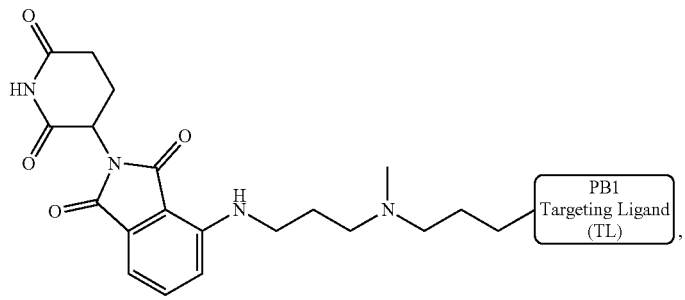
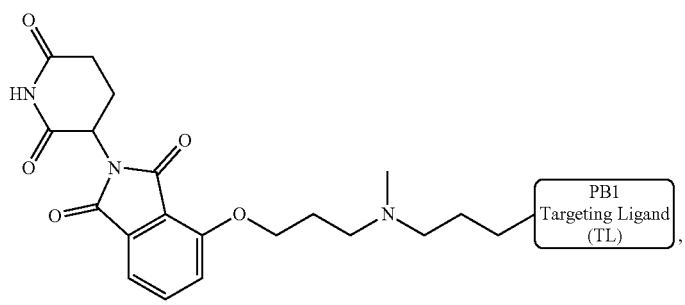
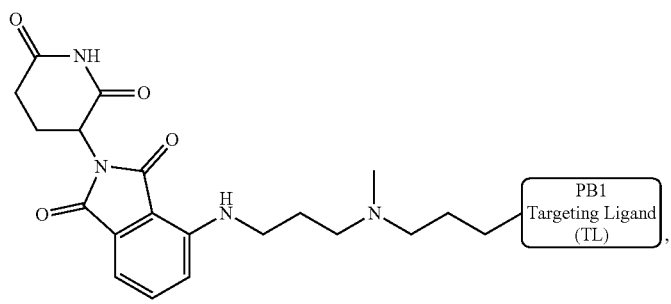
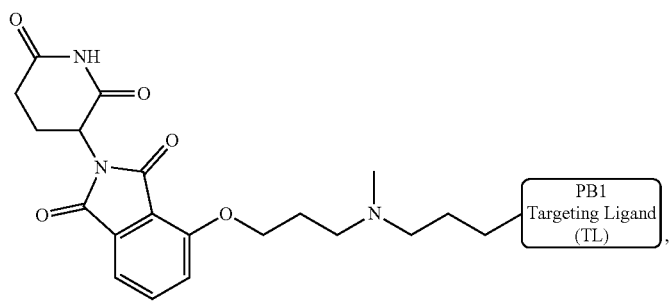
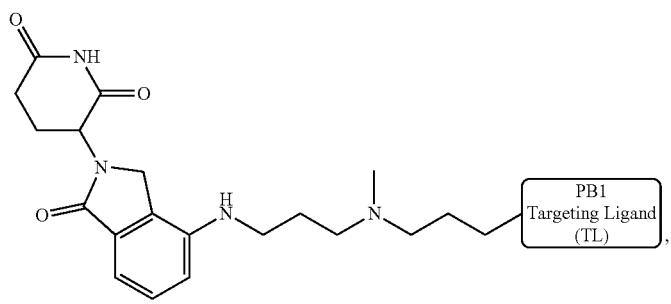

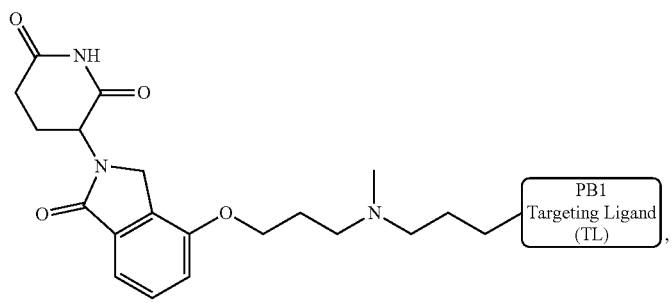
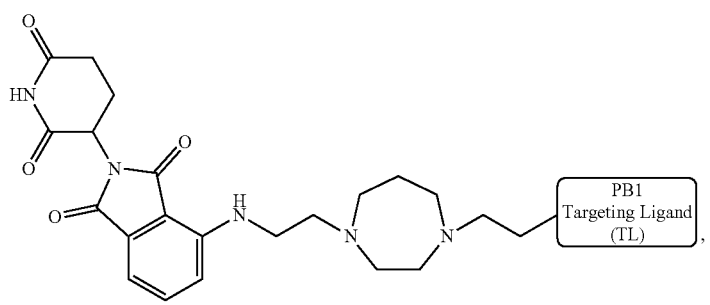
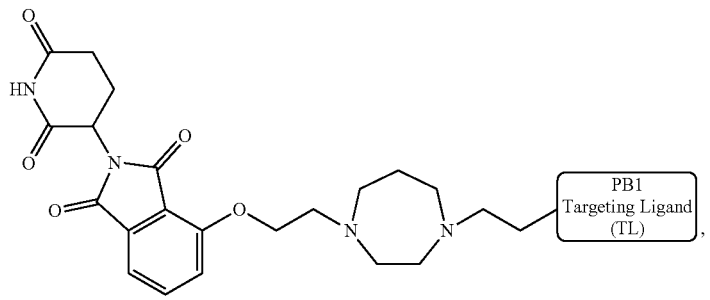
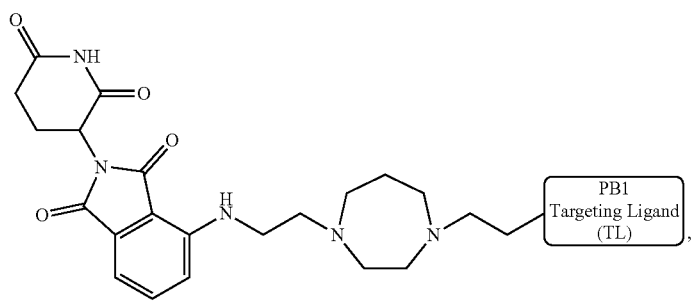
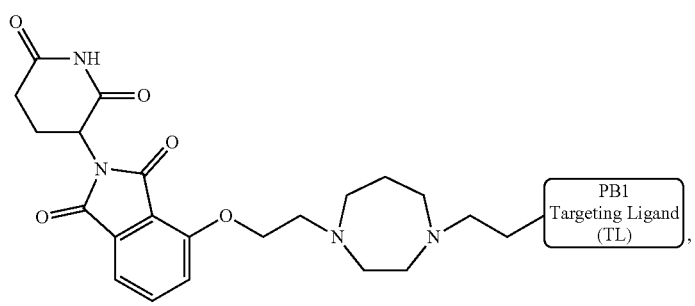

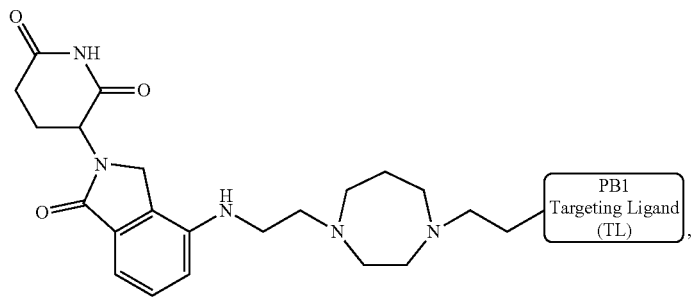
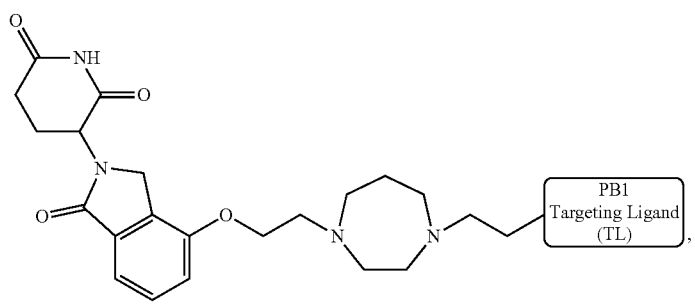
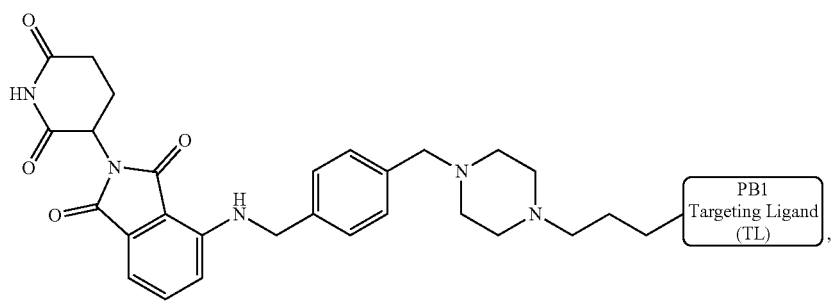
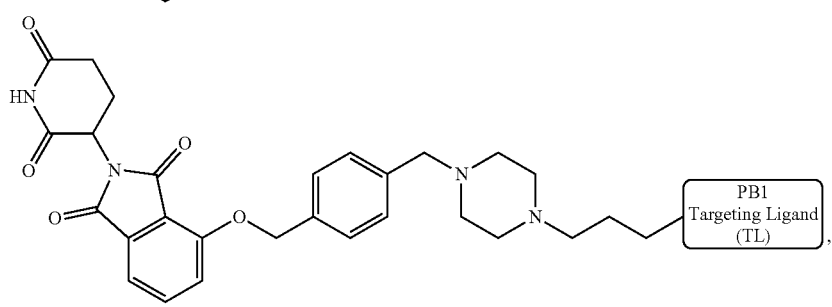
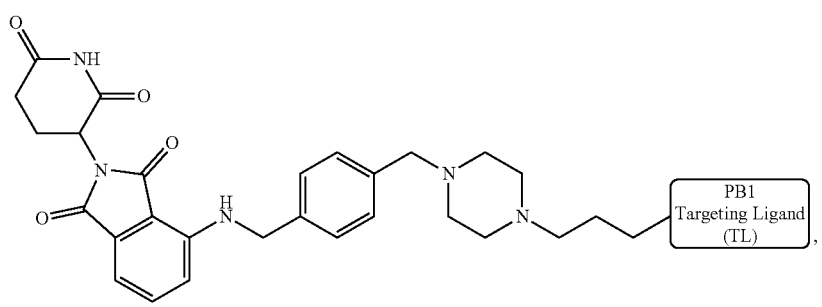

-continued
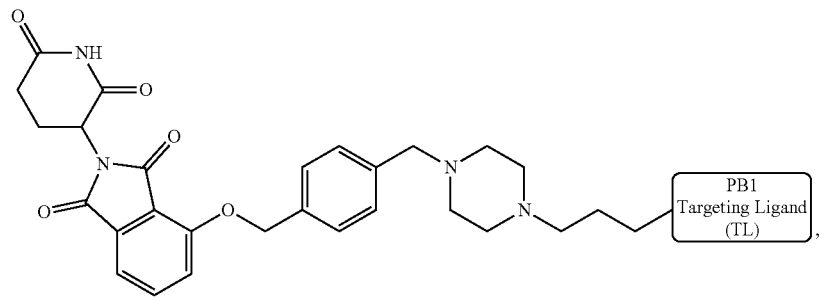
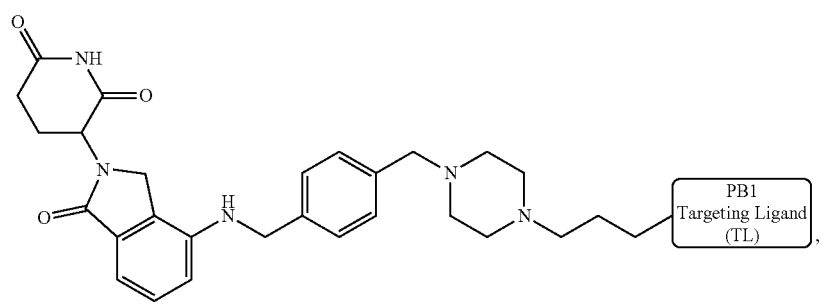
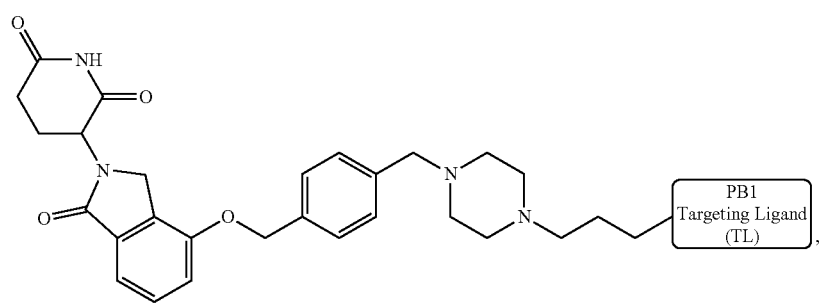
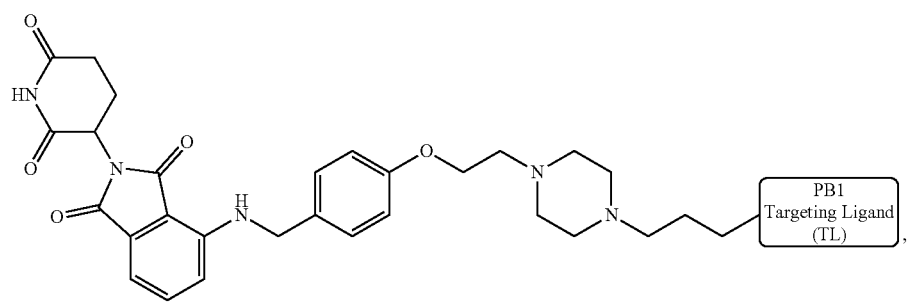
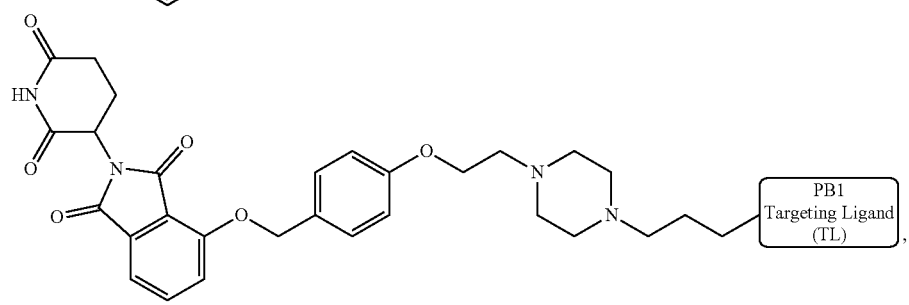

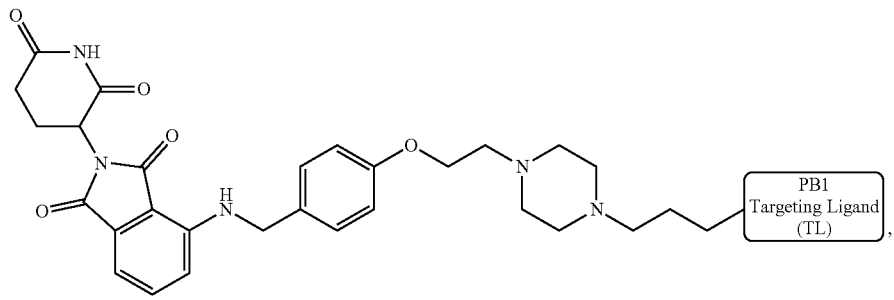
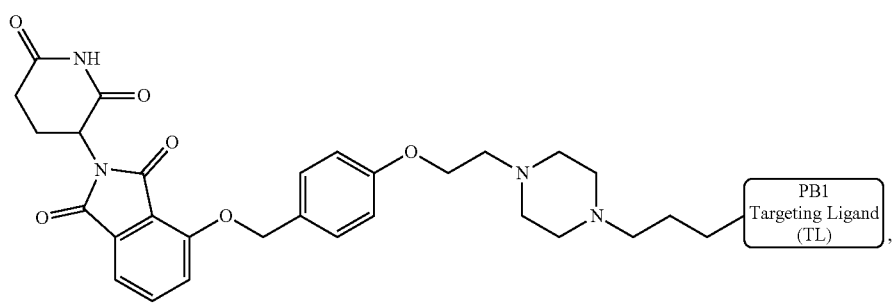
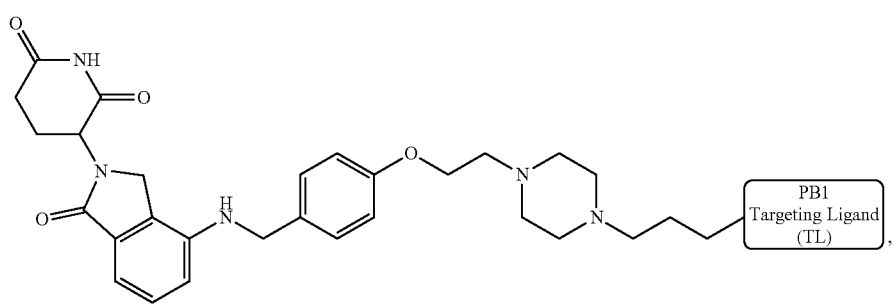
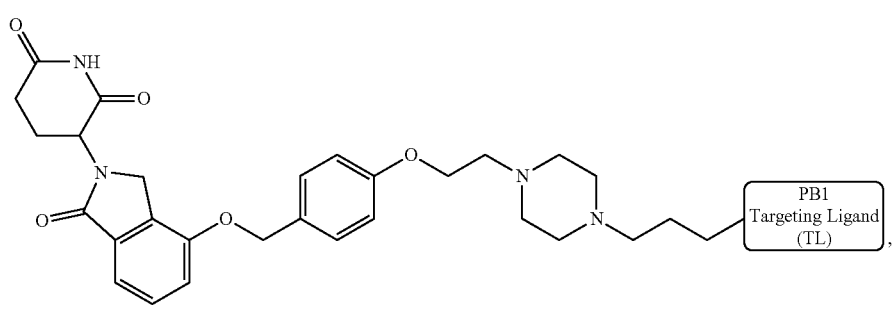
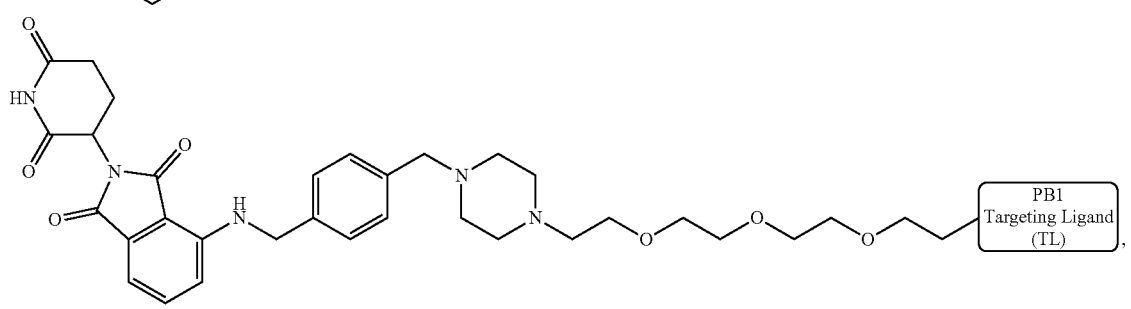

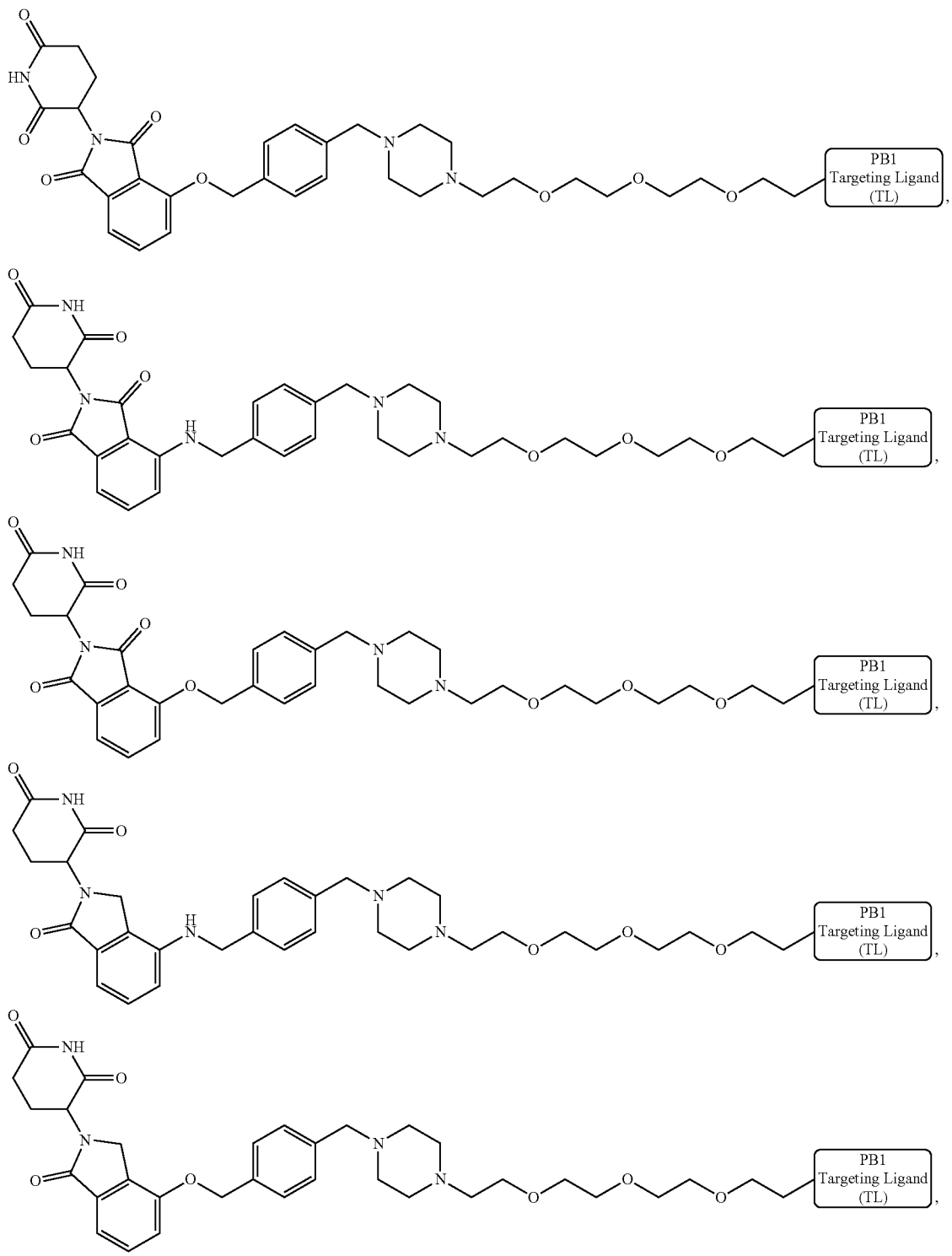

or a pharmaceutically acceptable salt or stereoisomer thereof.

The above structures are representative bivalent compounds of the present invention that contain cereblon targeted degrons (D1). VHL targeted degrons (D2-D5) can be substituted for the cereblon targeted degrons (D1) in the above structures to represent further bivalent compounds of the present invention.

Further representative bivalent compounds of the present invention are represented by the following structures:

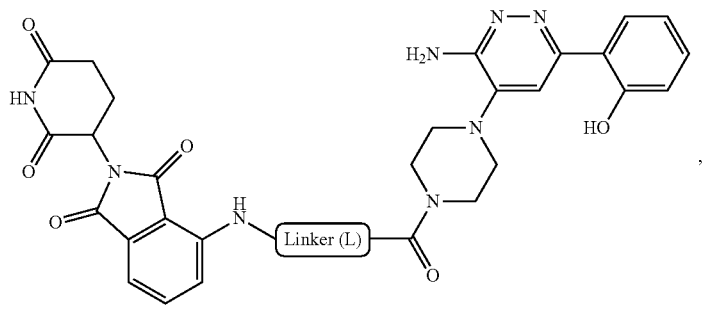
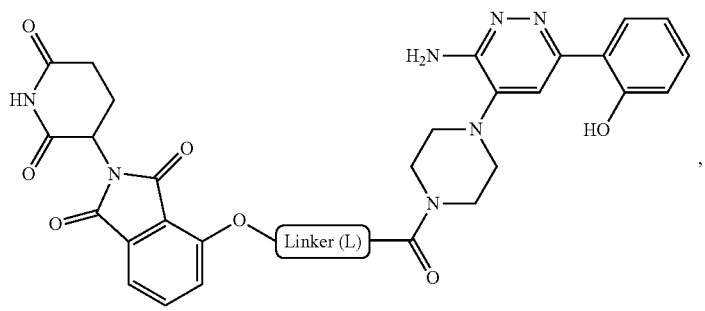
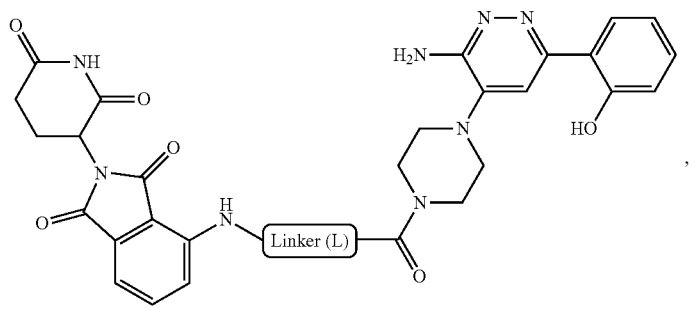
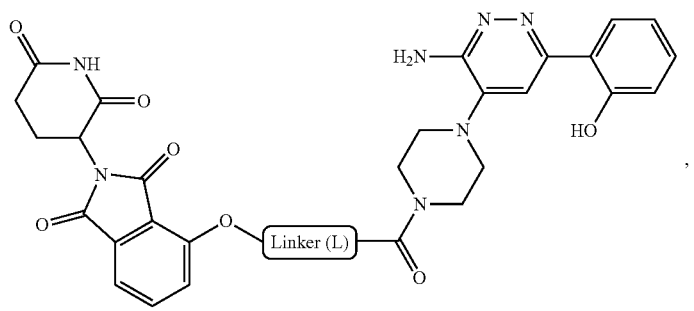
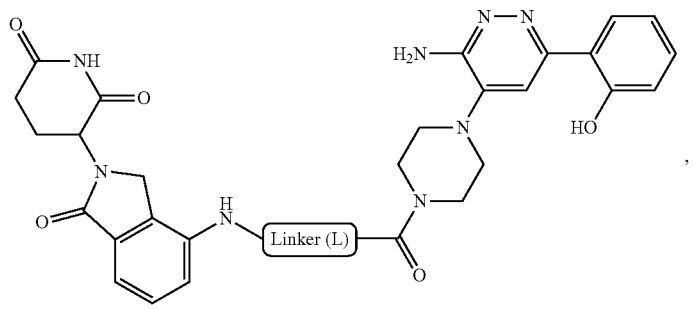

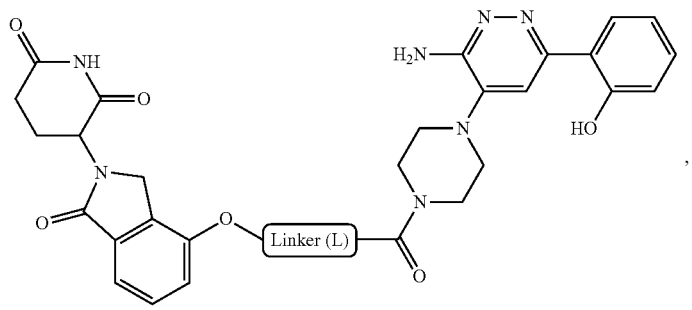
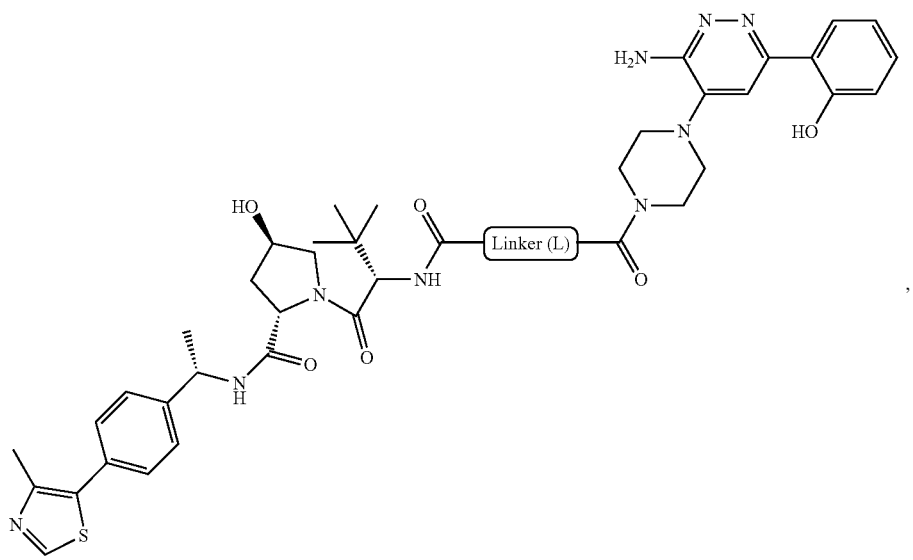
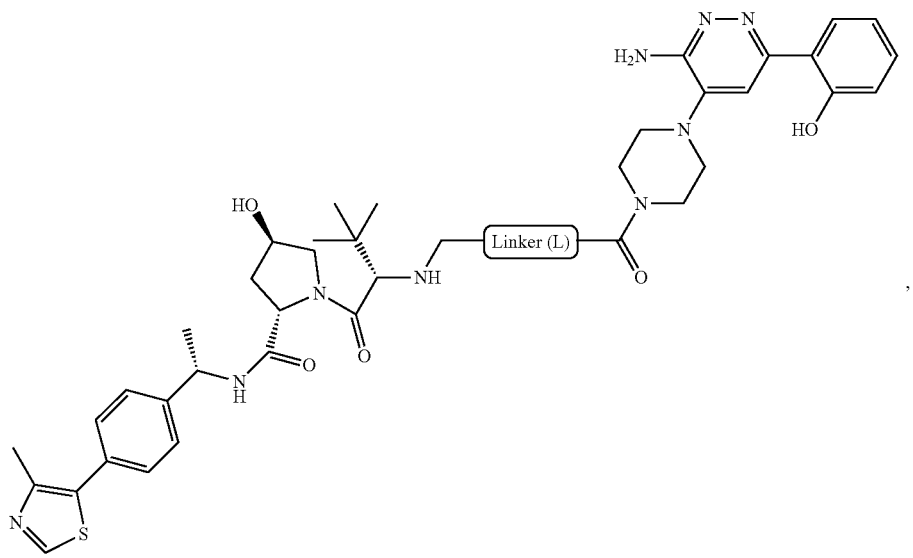

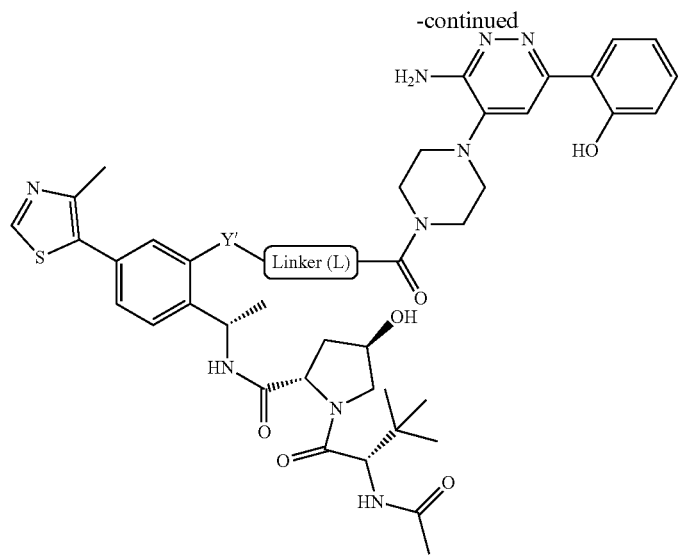
wherein Y' is a bond, N, O or C,
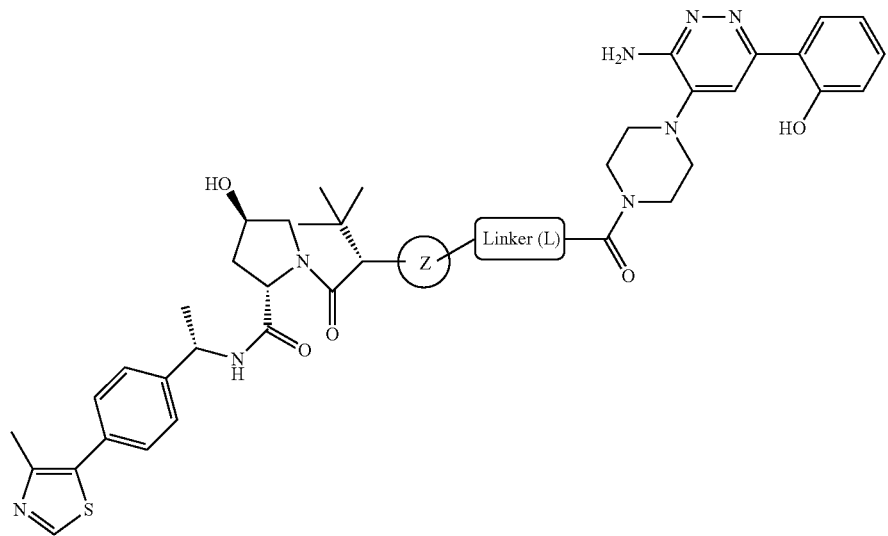
wherein Z is as defined above, or a pharmaceutically acceptable salt or stereoisomer thereof.
In some embodiments, the bivalent compounds of the present invention have the following structures:
(1)
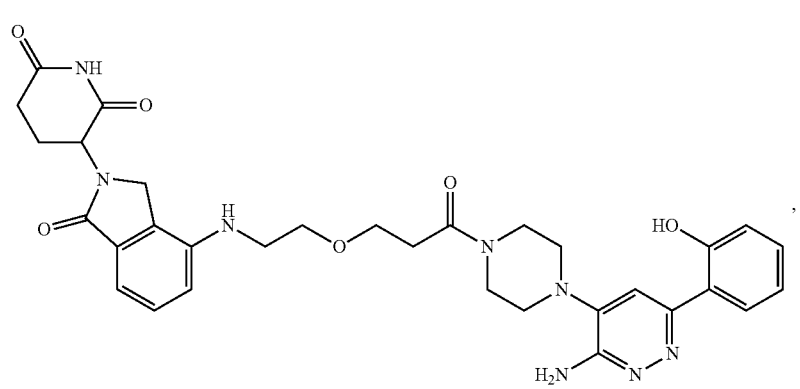

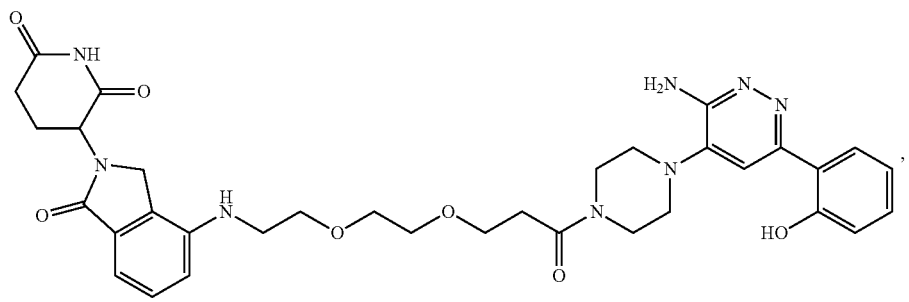
(2)
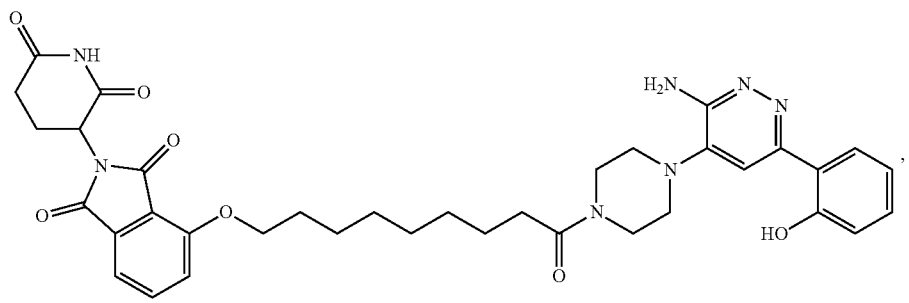
(3)
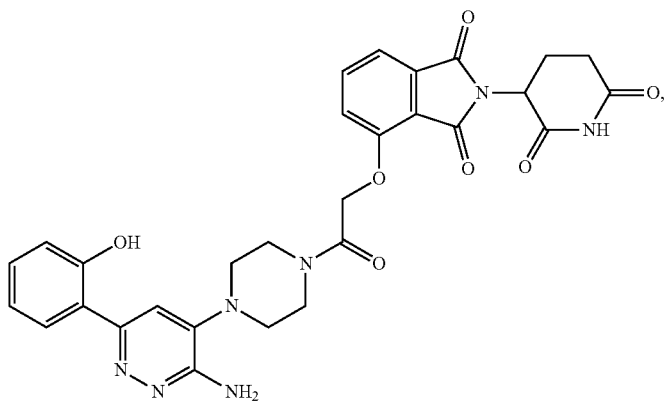
(4)
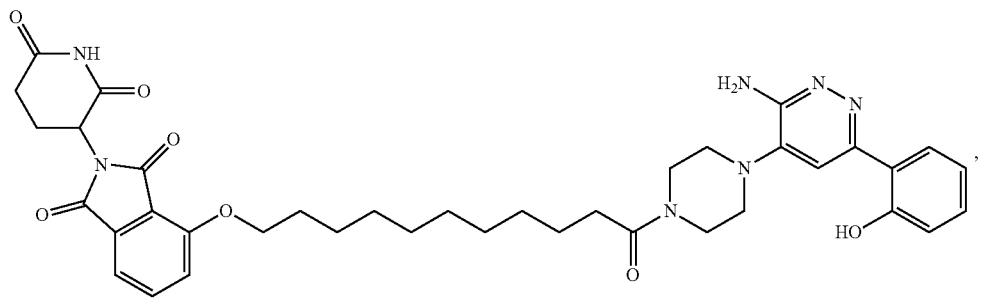
(5)

(6)
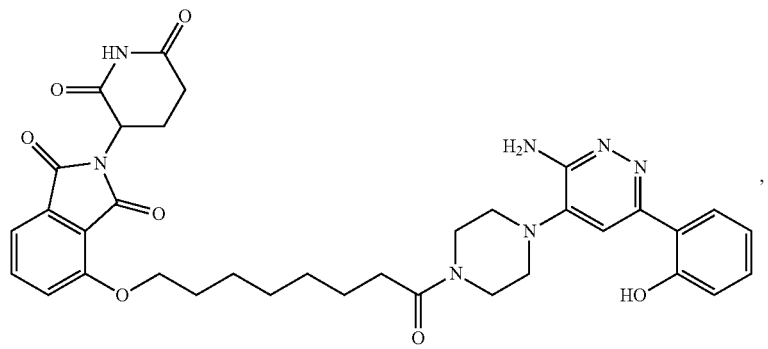
(7)
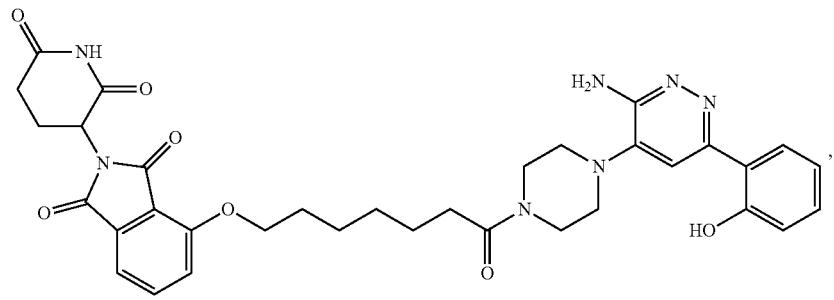
(8)
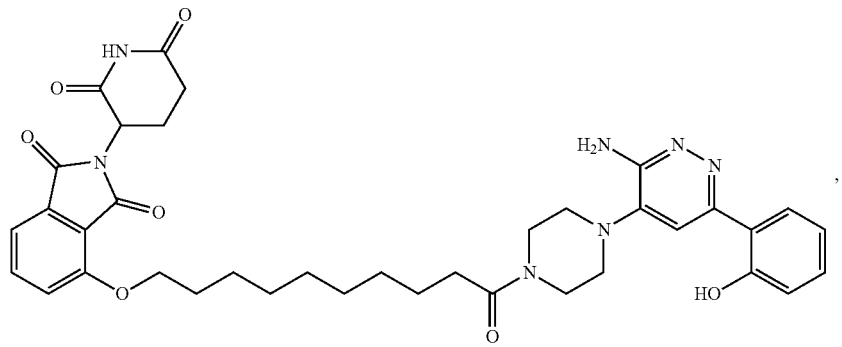
(9)
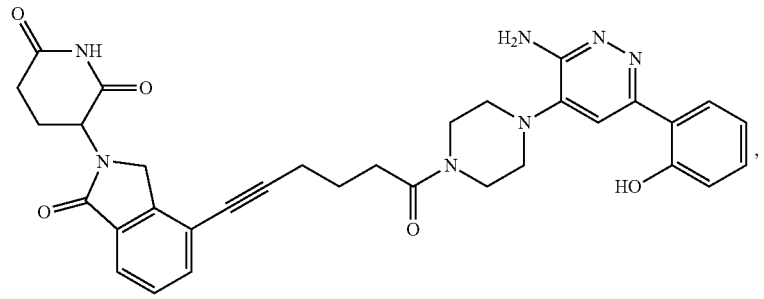
(10)
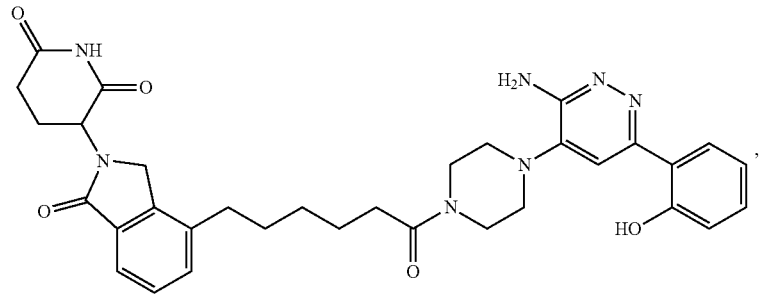

(11)
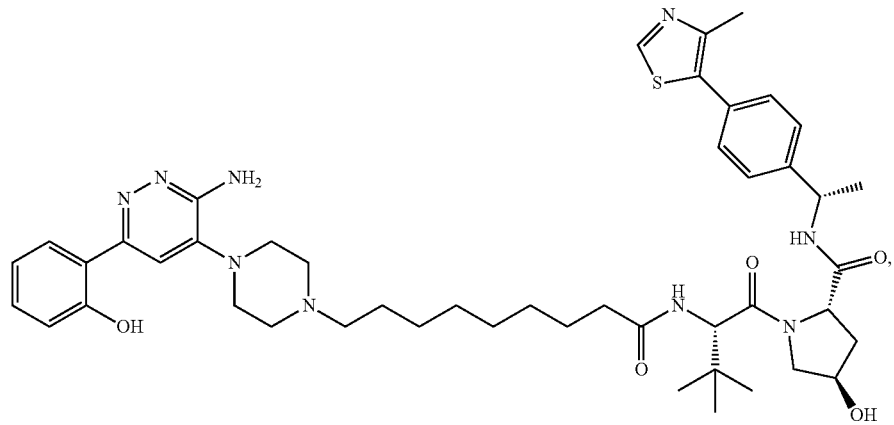
(12)
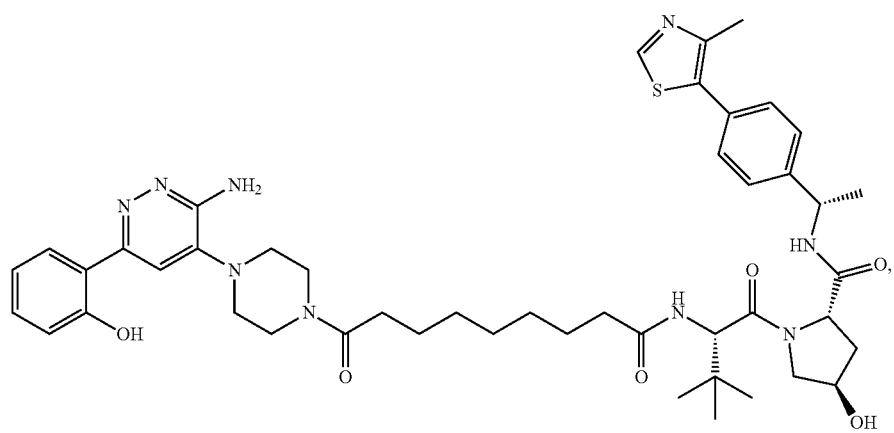
(13)
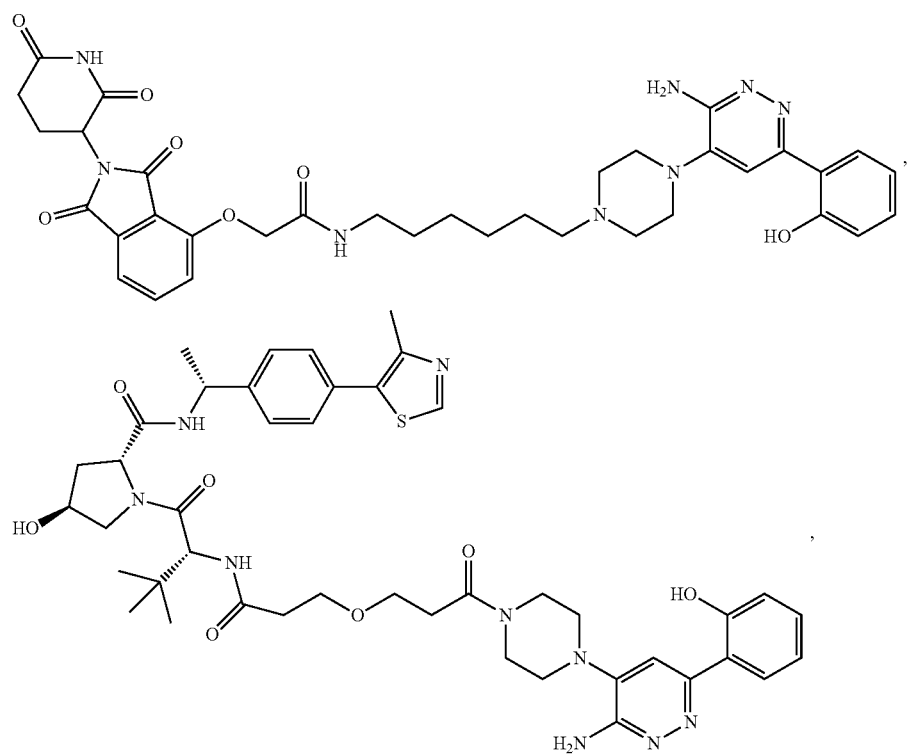

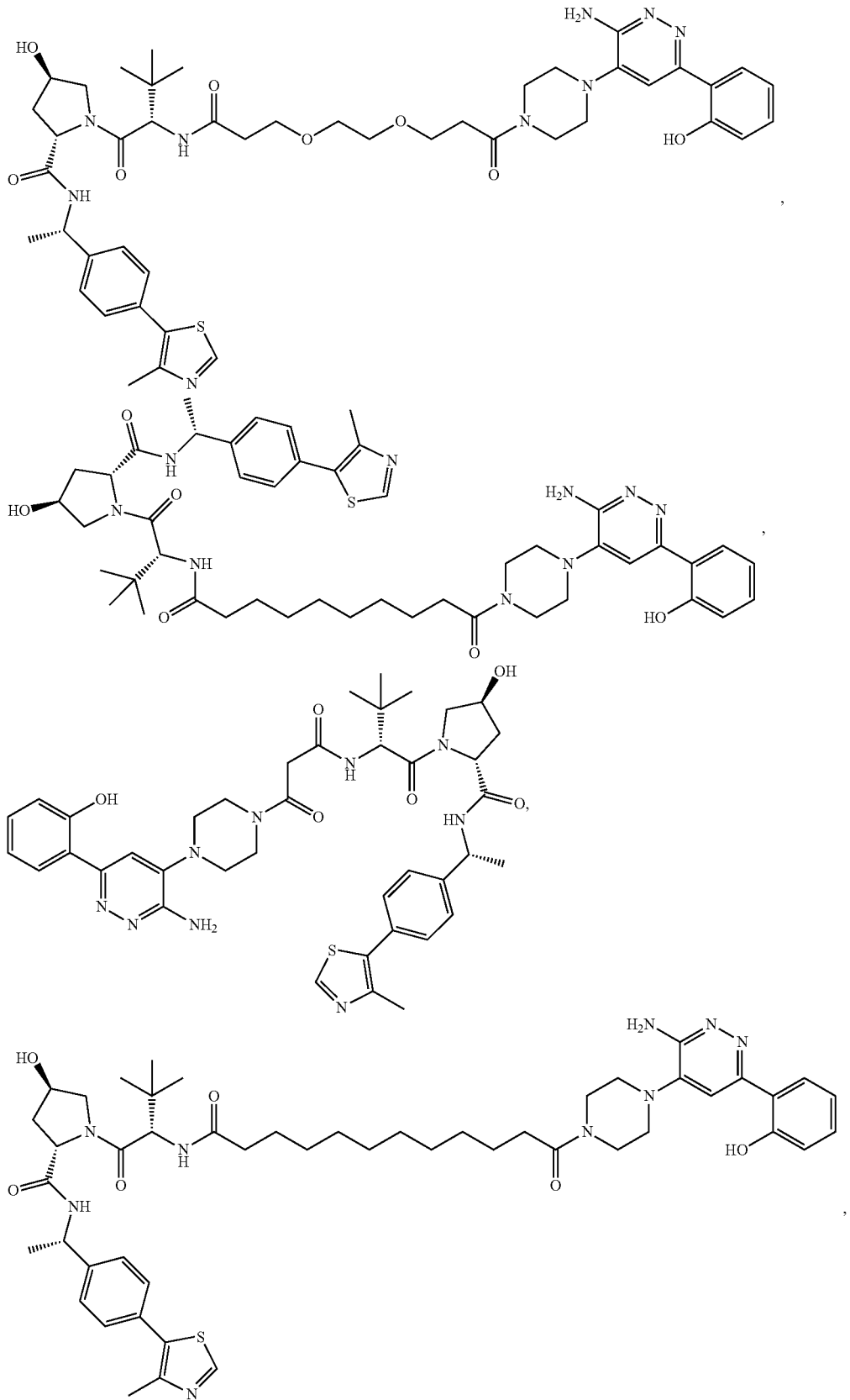

-continued
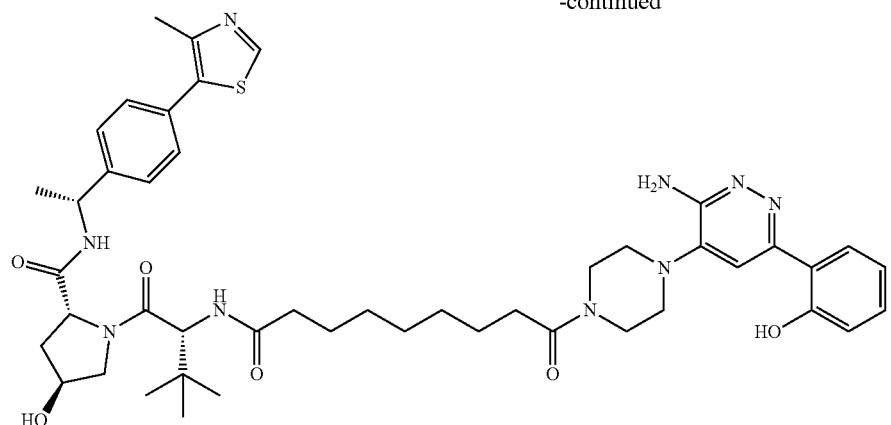
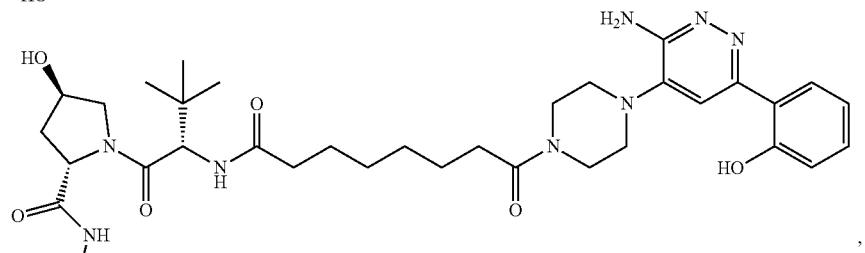
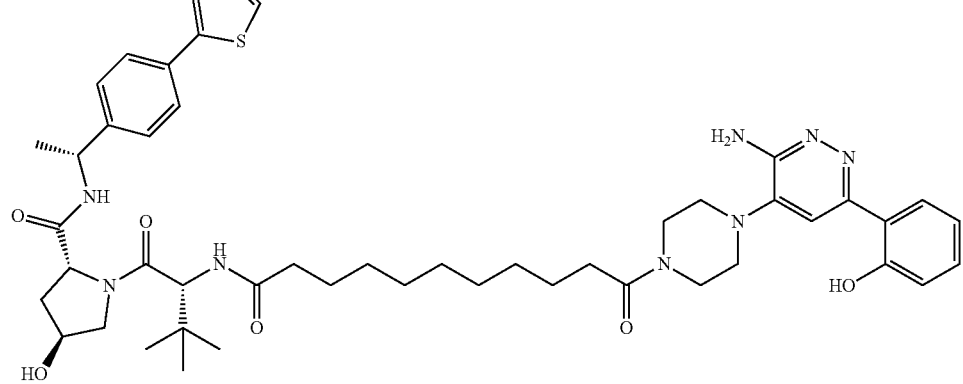
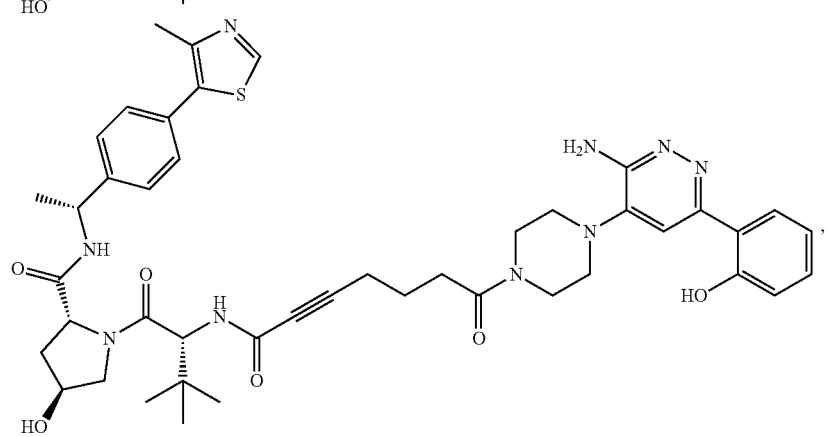

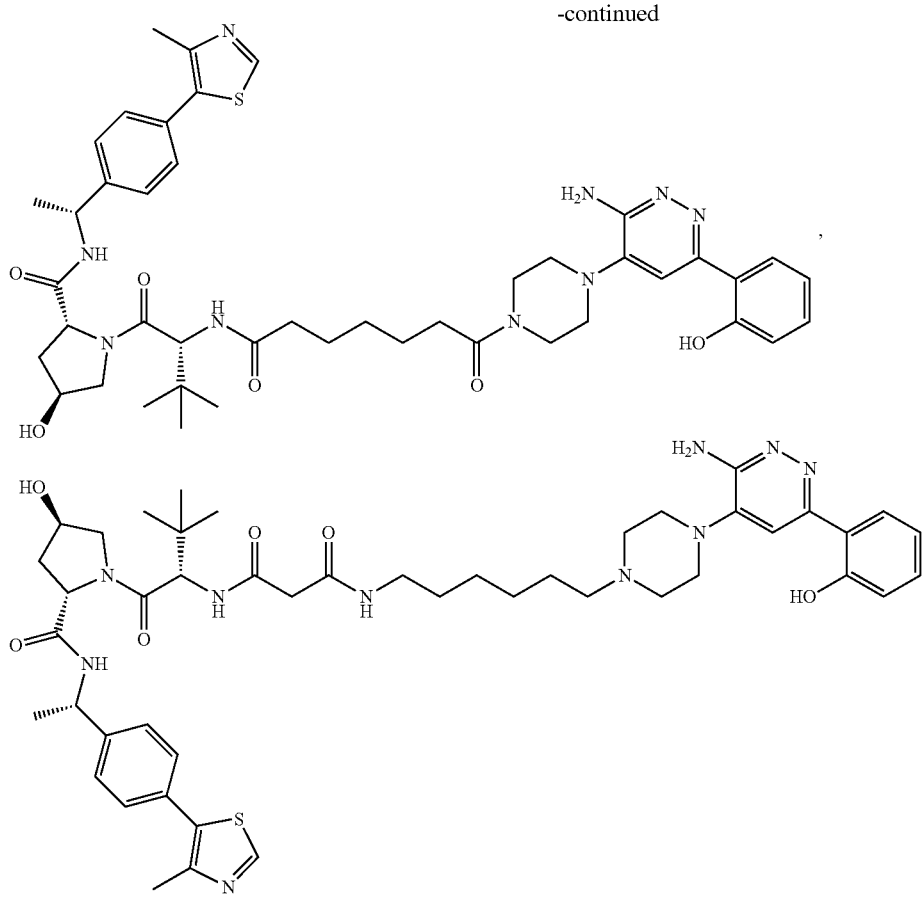

or a pharmaceutically acceptable salt or stereoisomer thereof.

Bivalent compounds of the present invention may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the bivalent compound of the present invention with a suitable acid or a base. Examples of pharmaceutically acceptable salts of the bivalent compounds of this invention include those derived from suitable inorganic bases such as Li, Na, K, Ca, Mg, Fe, Cu, Al, Zn and Mn salts. Examples of pharmaceutically acceptable, non-toxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluene-sulfonate salts and the like. Certain bivalent compounds of the invention can form pharmaceutically acceptable salts with various organic bases such as lysine, arginine, guanidine, diethanolamine or metformin.

In some embodiments, the bivalent compounds of the present invention may be isotopic derivatives in that they have at least one desired isotopic substitution of an atom, at an amount above the natural abundance of the isotope, i.e., enriched. In one embodiment, the bivalent compounds include deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances.

Bivalent compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the bivalent compounds of the present invention may be made and used in the form of individual isomers and substantially free of other isomers, or in the form of a mixture of various isomers, e.g., racemic mixtures of stereoisomers.

Methods of Synthesis

In another aspect, the present invention is directed to a method for making a bivalent compound of formula I, or a pharmaceutically acceptable salt or stereoisomer thereof. Broadly, the inventive bivalent compounds or pharmaceutically-acceptable salts or stereoisomers thereof may be prepared by any process known to be applicable to the preparation of chemically related compounds. The bivalent compounds of the present invention will be better understood in connection with the synthetic schemes that described in various working examples and which illustrate non-limiting methods by which the bivalent compounds of the invention may be prepared.

Pharmaceutical Compositions

In some embodiments, the present invention is directed to a pharmaceutical composition that includes a therapeutically effective amount of the bivalent compound of formula I or a pharmaceutically acceptable salt or stereoisomer thereof, and a pharmaceutically acceptable carrier. The bivalent compounds of the present invention may be formulated into several different types of pharmaceutical compositions that contain a therapeutically effective amount of the bivalent compound, and a pharmaceutically acceptable carrier.

Broadly, the inventive bivalent compounds may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral), parenteral (e.g., subcutaneous (s.c.), intravenous (i.v.), intramuscular (i.m.), and intrasternal injection, or infusion techniques, intra-arterial, intramedullary, intrathecal, intraventricular, transdermal, interdermal, rectal, intravaginal, intraperitoneal, topical mucosal, nasal, buccal, sublingual, intratracheal instillation, bronchial instillation, and/or inhalation. In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). In some embodiments, the compositions are formulated for oral or intravenous administration (e.g., systemic intravenous injection).

The term "pharmaceutically acceptable carrier," as known in the art, refers to a pharmaceutically acceptable material, composition or vehicle, suitable for administering bivalent compounds of the present invention to mammals. Suitable carriers may include, for example, liquids (both aqueous and non-aqueous alike, and combinations thereof), solids, encapsulating materials, gases, and combinations thereof (e.g., semi-solids), that function to carry or transport the compound from one organ, or portion of the body, to another organ or portion of the body. A carrier is "acceptable" in the sense of being physiologically inert to and compatible with the other ingredients of the formulation, and which is non-toxic to the subject or patient. Depending on the type of formulation, the composition may further include one or more pharmaceutically acceptable excipients.

Accordingly, bivalent compounds of formula I may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Bivalent compounds may also be formulated for rapid, intermediate or extended release.

Solid dosage forms for oral administration include capsules, tablets, pills, powders, and granules. In such solid dosage forms, the active bivalent compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bivalent compounds of formula I may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

In some embodiments, bivalent compounds of formula I may be formulated into tablets that may include excipients such as lactose monohydrate, microcrystalline cellulose, sodium starch glycolate, magnesium tartrate, and hydrophobic colloidal silica.

They may be formulated as solutions for parenteral and oral delivery forms, particularly to the extent that they are water-soluble. Parenteral administration may also be advantageous in that the compound may be administered relatively quickly such as in the case of a single-dose treatment and/or an acute condition.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bivalent compounds of formula I may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

The compositions may be formulated for buccal or sublingual administration, examples of which include tablets, lozenges and gels.

The compositions formula I may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bivalent compounds formula I may be formulated for topical administration which as used herein, refers to administration intradermally by invention of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

As used herein, the term, "therapeutically effective amount" refers to an amount of a bivalent compound of formula I or a pharmaceutically acceptable salt or a stereoisomer thereof that is effective in producing the desired therapeutic response in a particular patient suffering from a disease or disorder. The term "therapeutically effective amount" thus includes the amount of the bivalent compound of the invention or a pharmaceutically acceptable salt or a stereoisomer thereof, that when administered, induces a positive modification in the disease or disorder to be treated (e.g., to selectively inhibit/degrade PB1, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amount of PB1 in diseased cells.

The total daily dosage of the compounds and usage thereof may be decided in accordance with standard medical practice, e.g., by the attending physician using sound medical judgment. Accordingly, the specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

Bivalent compounds of formula I may be effective over a wide dosage range. In some embodiments, the total daily dosage (e.g., for adult humans) may range from about 0.001 to about 1000 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, or in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg).

Methods of Use

In some aspects, the present invention is directed to methods of treating diseases or disorders involving dysfunctional or dysregulated SWI/SNF chromatin-remodeling complex activity, including PB1 activity, that entails administration of a therapeutically effective amount of a bivalent compound formula I or a pharmaceutically acceptable salt or stereoisomer thereof, to a subject in need thereof.

The diseases or disorders may be said to be characterized or mediated by dysfunctional SWI/SNF chromatin-remodeling complex activity, including PB1 activity (e.g., elevated levels of protein or otherwise functionally abnormal relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, bivalent compounds of the invention may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the bivalent compounds of the present invention include inflammatory diseases and conditions, autoimmune diseases, neurodegenerative diseases, heart diseases, viral diseases, chronic and acute kidney diseases or injuries, vascular diseases, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ecodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, autoimmune thyroditis or Hashimoto's disease, Sjogren's syndrome, vitiligo, Wegener granulamatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cerebral malaria, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, thrombosis, restenosis, silicosis, pulmonary sarcosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sudden infant death syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, cystic fibrosis, uveitis, polymyositis, proctitis, interstitial lung fibrosis, dermatomyositis, arteriosclerosis, atherosclerosis, amyotrophic lateral sclerosis, asocality, immune response, varicosis, vaginitis, including chronic recurrent yeast vaginitis, depression, Sudden Infant Death Syndrome, obesity and varicosis.

In other embodiments, the methods are directed to treating subjects having cancer. Broadly, the bivalent compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, gestational trophoblastic tumor glioma, head and neck cancer, Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodyplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with bivalent compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present invention entail treatment of subjects having cell proliferative diseases or disorders of the hematological system, liver (hepatocellular), brain, lung, colorectal (e.g., colon), pancreas, prostate, skin, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, primary CNS lymphoma (PCNSL), marginal zone lymphoma (MZL), leukemia, including chronic lymphocytic leukemia (CLL), childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the long, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polypopsis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

In some embodiments, the bivalent compounds or pharmaceutically acceptable salts or stereoisomers of the present invention are used in the treatment of high-risk neuroblastoma (NB).

In some embodiments, the disease or disorder is acute myeloid leukemia (AML), multiple myeloma (MM), melanoma, rhabdomyosarcoma, or diffuse large B cell lymphoma. In other embodiments, the disease or disorder is small solid tumor. In other embodiments, the disease or disorder is colon cancer, rectum cancer, stomach cancer, breast cancer or pancreatic cancer.

In some embodiments, bivalent compounds of the present invention may be used to treat lung cancer (e.g., NSLC), advanced and metastatic solid tumors, ALK-positive anaplastic large cell lymphoma, central nervous system tumors, neuroblastoma, breast cancer, cholangiocarcinoma, colorectal cancer, head and neck neoplasms, neuroendocrine tumors, ovarian cancer, pancreatic cancer, papillary thyroid cancer, primary brain tumors, renal cell carcinoma, Sarcomas, salivary gland cancers, metastatic anaplastic thyroid cancer, undifferentiated thyroid cancer, glioblastoma, brain metastases, advanced malignant solid neoplasm, metastatic pancreatic adenocarcinoma, stage III and IV pancreatic cancer, melanoma (advanced and unresectable), CD30-positive neoplastic cells, BRAF/NRAS wild-type stage III-IV melanoma, advanced, refractory, and recurrent malignant solid neoplasm, Ann Arbor stage III and stage IV childhood Non-Hodgkin's lymphoma, histiocytosis, recurrent childhood central nervous system neoplasm and Non-Hodgkin's lymphoma, refractory central nervous system neoplasm, ROS1-positive refractory Non-Hodgkin's lymphoma, childhood Langerhans cell histiocytosis, histiocytic sarcoma, juvenile xanthogranuloma, malignant glioma, recurrent childhood ependymoma, malignant germ cell tumor and medulloblastoma, recurrent childhood Non-Hodgkin's lymphoma, rhabdomyosarcoma, and soft tissue sarcoma, recurrent Ewing sarcoma, glioma, hepatoblastoma, neuroblastoma, osteosarcoma, and peripheral primitive neuroectodermal tumor.

The bivalent compounds of formula (I) of the present invention may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of a bivalent compound of formula I of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bivalent compound may be dosed twice a day (BID) over the course of two and a half days (for a total of 5 doses) or once a day (QD) over the course of two days (for a total of 2 doses). In other embodiments, the bivalent compound may be dosed once a day (QD) over the course of five days.

Combination Therapy

The bivalent compounds of formula I of the present invention may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bivalent compound of formula I of the invention in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anticancer agents that may be used in combination with the inventive bivalent compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the bivalent compound of formula I may be used in combination with other anti-cancer agents to treat melanoma, examples of which include Aldesleukin, Binimetinib, Cobimetinib, Dabrafenib, Dacarbazine, Encorafenib, Imlygic, Ipilimumab, Nivolumab, Peginterferon Alfa-2b, Pembrolizumab, Talimogene Laherparepvec, Trametinib, and Vemurafenib.

In some embodiments, the bivalent compound of formula I of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the bivalent compound of formula I of the present invention and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bivalent compound of formula I of the present invention or a pharmaceutical composition. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Unless otherwise noted, reagents and solvents were used as received from commercial suppliers. Proton nuclear magnetic resonance spectra were obtained on Bruker AVANCE spectrometer at 500 MHz for proton. Spectra are given in ppm (δ) and coupling constants, J, are reported in Hertz. The solvent peak was used as the reference peak for proton spectra. Liquid chromatography-mass spectra were obtained on Waters ultra-performance liquid chromatography (UPLC) ion trap electrospray ionization (ESI) mass spectrometer.

Example 1: Synthesis of 3-(4-((2-(3-(4-(3-amino-6-(2-hydroxyphenyl)pyridazin-4-yl)piperazin-1-yl)-3-oxopropoxy)ethyl)amino)-1-oxoisoindolin-2-yl)piperidine-2,6-dione (1)

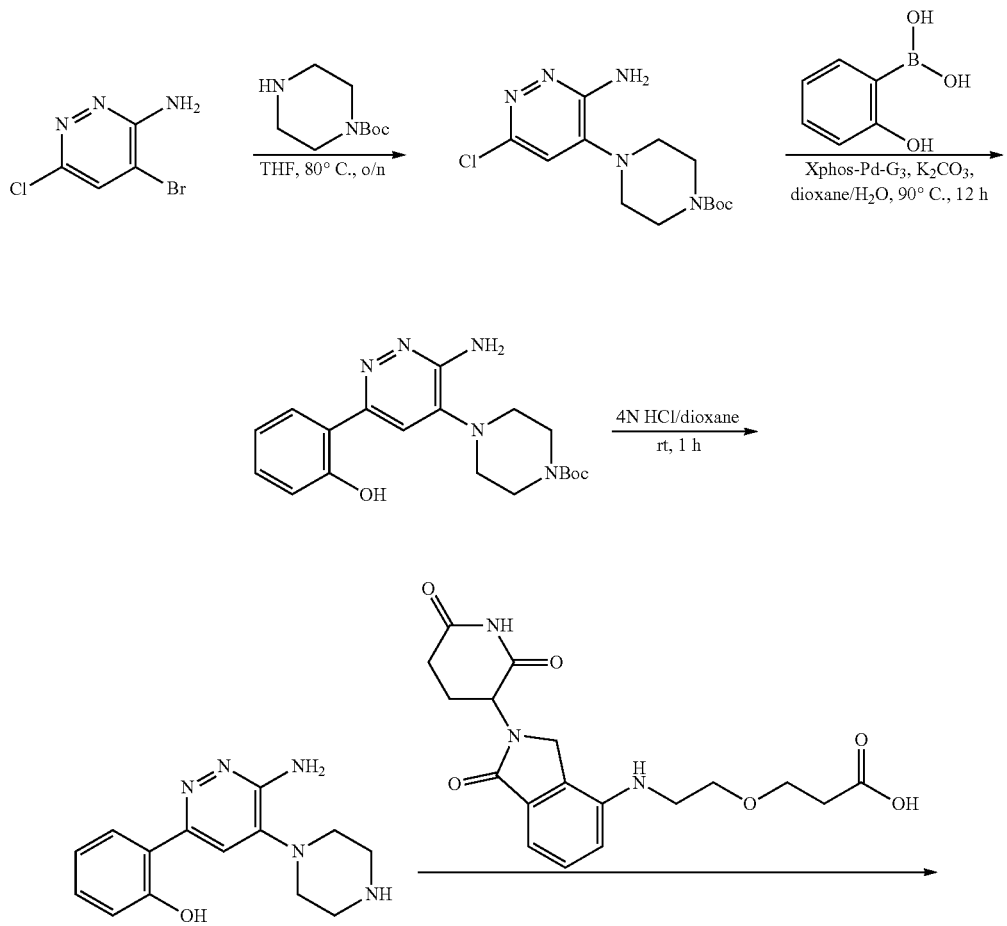

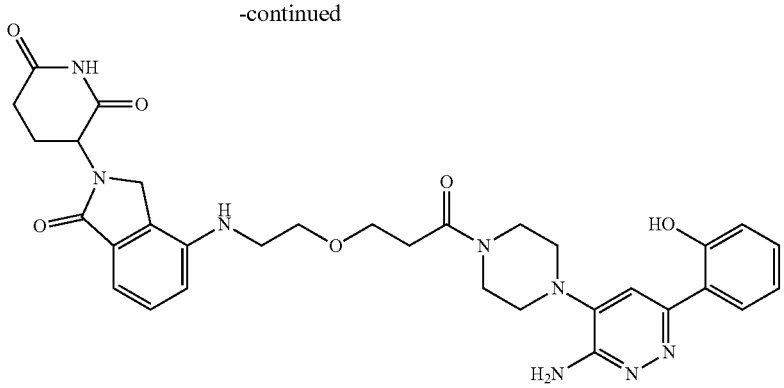

Tert-butyl 4-(3-amino-6-(2-hydroxyphenyl)pyridazin-4-yl)piperazine-1-carboxylate To a solution of tert-butyl 4-(3-amino-6-chloropyridazin-4-yl)piperazine-1-carboxylate (200 mg, 0.64 mmol) in dioxane/H2O (10 mL/1 mL) was added (2-hydroxyphenyl) boronic acid (114 mg, 0.83 mmol), Xphos-Pd-G3 (54 mg, 0.064 mmol) and K$_2$CO$_3$ (180 mg, 1.28 mmol). The reaction mixture was stirred at 90° C. overnight with N$_2$ protected. The reaction mixture was cooled and concentrated. The residue was purified with silica gel column to give the desired product (140 mg, yield 59%). LCMS (m/z): 372 [M+H]$^+$.

2-(6-amino-5-(piperazin-1-yl)pyridazin-3-yl)phenol

To a solution of tert-butyl 4-(3-amino-6-(2-hydroxyphenyl)pyridazin-4-yl)piperazine-1-carboxylate (140 mg, 0.38 mmol) in Dioxane (5 mL) was added 4N HCl/dioxane (3 mL). The reaction mixture was stirred at room temperature (rt) for 1 hour. The solid was filtered to give the desired product (100 mg, 85%) as HCl salt. LCMS (m/z): 272 [M+H]$^+$.

3-(4-((2-(3-(4-(3-amino-6-(2-hydroxyphenyl)pyridazin-4-yl)piperazin-1-yl)-3-oxopropoxy)ethyl)amino)-1-oxoisoindolin-2-yl)piperidine-2,6-dione (1)

The mixture of 2-(6-amino-5-(piperazin-1-yl)pyridazin-3-yl)phenol (10 mg, 0.032 mmol), 3-(2-((2-(2,6-dioxopiperidin-3-yl)-1-oxoisoindolin-4-yl)amino)ethoxy)propanoic acid (12 mg, 0.032 mmol) in dimethyl fumarate (DMF) (0.5 mL) was added (1-[Bis(dimethylamino)methylene]-1H-1,2,3-triazolo[4,5-b]pyridinium 3-oxid hexafluorophosphate, HATU) (20 mg, 0.05 mmol) and N,N-diisopropylethyl amine (DIPEA) (0.03 mL, 0.16 mmol). The reaction mixture was stirred at rt overnight. After completion, the mixture was extracted with ethyl acetate (EA) (50 mL×3), the organic phase was washed with brine (20 mL×3), dried with Na$_2$SO$_4$, filtered, concentrated to remove the solvent, the residue was purified by prep-HPLC to obtain the target compound (white solid, 10.4 mg, yield 52%). LCMS (m/z): 629 [M+H]$^+$. $^1$H NMR (500 MHz, DMSO-d$_6$) δ 14.15 (s, 1H), 11.01 (s, 1H), 8.12-7.78 (m, 1H), 7.52 (s, 1H), 7.36-7.14 (m, 2H), 7.02-6.85 (m, 3H), 6.81 (d, J=8.0 Hz, 1H), 6.41 (s, 2H), 5.58 (t, J=5.6 Hz, 1H), 5.13 (dd, J=13.3, 5.2 Hz, 1H), 4.38-4.14 (m, 2H), 3.81-3.55 (m, 8H), 3.33 (m, 2H), 3.24-2.85 (m, 5H), 2.73-2.57 (m, 3H), 2.31 (m, 1H), 2.09-1.95 (m, 1H).

Example 2: Synthesis of 3-(4-((2-(2-(3-(4-(3-amino-6-(2-hydroxyphenyl)pyridazin-4-yl)piperazin-1-yl)-3-oxopropoxy)ethoxy)ethyl)amino)-1-oxoisoindolin-2-yl)piperidine-2,6-dione

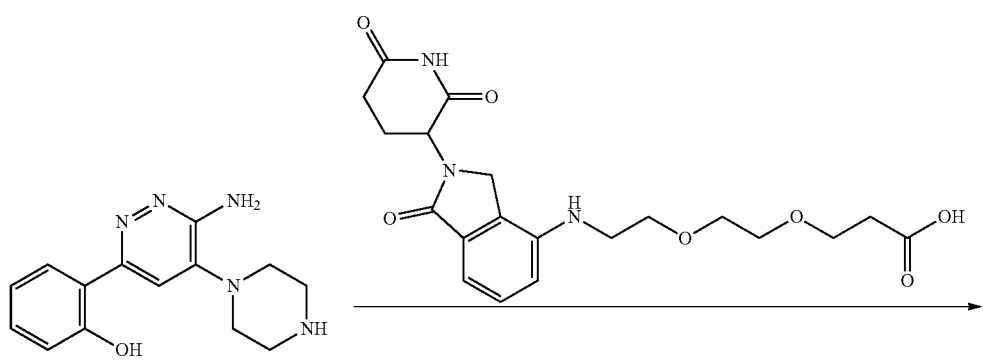

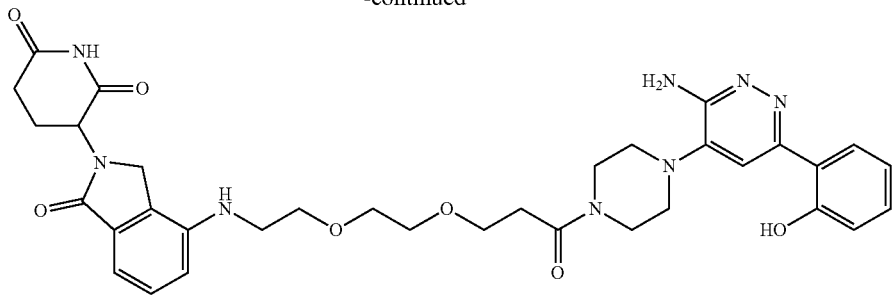

2

A mixture of 2-(6-amino-5-(piperazin-1-yl)pyridazin-3-yl)phenol (10 mg, 0.032 mmol), 3-(2-(2-(((2-(2,6-dioxopiperidin-3-yl)-1-oxoisoindolin-4-yl)amino)ethoxy)ethoxy)propanoic acid (14 mg, 0.032 mmol) in DMF (0.5 mL) was added HATU (20 mg, 0.05 mmol) and DIPEA (0.03 mL, 0.16 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 10.7 mg, yield 50%). LCMS (m/z): 673 [M+H]$^+$. $^1$H NMR (500 MHz, DMSO-d$_6$) δ 14.08 (s, 1H), 10.93 (s, 1H), 7.86-7.81 (m, 1H), 7.45 (s, 1H), 7.24-7.13 (m, 2H), 6.87 (d, J=7.4 Hz, 1H), 6.81 (m, 2H), 6.71 (d, J=8.1 Hz, 1H), 6.34 (s, 2H), 5.48 (t, J=5.8 Hz, 1H), 5.04 (dd, J=13.2, 5.1 Hz, 1H), 4.15 (d, J=17.1 Hz, 1H), 4.05 (d, J=17.1 Hz, 1H), 3.60 (m, 6H), 3.52 (t, J=5.9 Hz, 2H), 3.47 (m, 4H), 3.23 (d, J=5.6 Hz, 2H), 3.03-2.98 (m, 2H), 2.96 (m, 2H), 2.85 (m, 1H), 2.56 (m, 1H), 2.43 (m, 4H), 2.24 (m, 1H), 1.96 (m, 1H).

Example 3: Synthesis of 4-((9-(4-(3-amino-6-(2-hydroxyphenyl)pyridazin-4-yl)piperazin-1-yl)-9-oxononyl)oxy)-2-(2,6-dioxopiperidin-3-yl)isoindoline-1,3-dione (3)

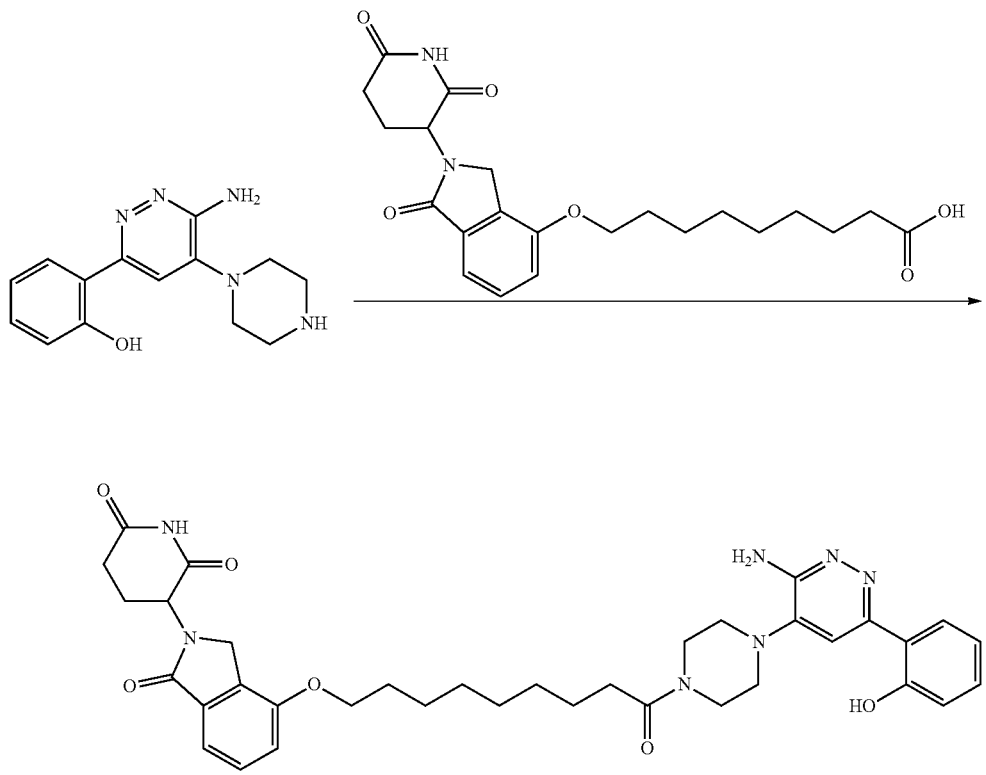

3

The mixture of 2-(6-amino-5-(piperazin-1-yl)pyridazin-3-yl)phenol (10 mg, 0.032 mmol), 9-((2-(2,6-dioxopiperidin-3-yl)-1,3-dioxoisoindolin-4-yl)oxy)nonanoic acid (14 mg, 0.032 mmol) in DMF (0.5 mL) was added HATU (20 mg, 0.05 mmol) and DIPEA (0.03 mL, 0.16 mmol). The reaction mixture was stirred at rt overnight. After completion, the mixture was extracted with EA (50 mL×3), the organic phase was washed with brine (20 mL×3), dried with $Na_2SO_4$, filtered, concentrated to remove the solvent, the residue was purified by prep-HPLC to obtain the target compound (white solid, 8.9 mg, yield 41%). LCMS (m/z): 684 [M+H]$^+$. $^1$H NMR (500 MHz, DMSO-d$_6$) δ 11.03 (s, 1H), 7.77-7.70 (m, 1H), 7.54 (d, J=7.7 Hz, 1H), 7.47-7.39 (m, 2H), 7.37 (d, J=7.3 Hz, 1H), 7.31 (t, J=7.7 Hz, 1H), 7.28 (s, 2H), 6.96 (d, J=8.2 Hz, 1H), 6.91 (t, J=7.5 Hz, 1H), 5.01 (dd, J=12.8, 5.5 Hz, 1H), 4.13 (t, J=6.4 Hz, 2H), 3.61 (t, J=5.0 Hz, 4H), 3.20 (s, 2H), 3.15 (t, J=5.1 Hz, 2H), 2.86-2.75 (m, 1H), 2.52 (m, 1H), 2.50-2.38 (m, 2H), 2.28 (t, J=7.5 Hz, 2H), 1.96 (tt, J=7.7, 4.6 Hz, 1H), 1.69 (p, J=6.8 Hz, 2H), 1.41 (m, 4H), 1.33-1.21 (m, 6H).

Example 4: Synthesis of 4-(2-(4-(3-amino-6-(2-hydroxyphenyl)pyridazin-4-yl)piperazin-1-yl)-2-oxoethoxy)-2-(2,6-dioxopiperidin-3-yl)isoindoline-1,3-dione (4)

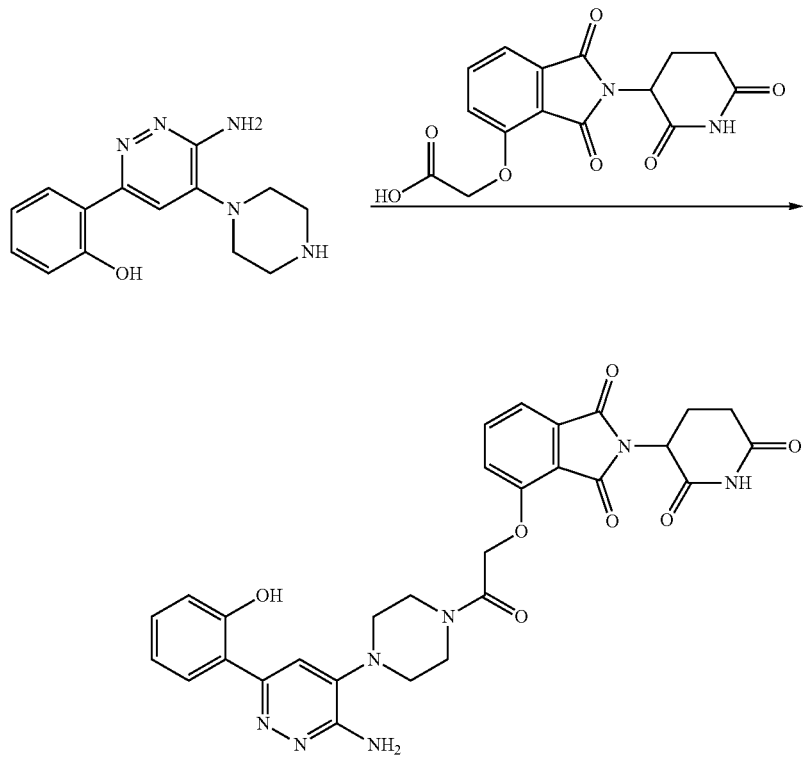

4

A mixture of 2-(6-amino-5-(piperazin-1-yl)pyridazin-3-yl)phenol (20 mg, 0.065 mmol), 2-((2-(2,6-dioxopiperidin-3-yl)-1,3-dioxoisoindolin-4-yl)oxy)acetic acid (22 mg, 0.065 mmol) in DMF (1 mL) was added HATU (37 mg, 0.1 mmol) and DIPEA (0.06 mL, 0.33 mmol). The reaction mixture was stirred at rt overnight. After completion, the mixture was extracted with EA (50 mL×3), the organic phase was washed with brine (20 mL×3), dried with $Na_2SO_4$, filtered, concentrated to remove the solvent, the residue was purified by prep-HPLC to obtain the target compound (white solid, 6.7 mg, yield 18%). LCMS (m/z): 586 [M+H]$^+$. $^1$H NMR (500 MHz, DMSO-d$_6$) δ 11.11 (s, 1H), 7.80 (m, 1H), 7.60 (dd, J=7.8, 1.7 Hz, 1H), 7.52 (s, 1H), 7.48 (m, 1H), 7.45-7.37 (m, 2H), 7.19 (m, 1H), 7.08-6.97 (m, 2H), 5.26 (s, 2H), 5.14-5.07 (m, 1H), 3.72 (m, 4H), 3.39 (s, 2H), 3.30 (s, 2H), 2.94-2.84 (m, 1H), 2.66-2.52 (m, 2H), 2.50 (m, 2H), 2.10-2.00 (m, 1H).

Example 5: Synthesis of 4-((11-(4-(3-amino-6-(2-hydroxyphenyl)pyridazin-4-yl)piperazin-1-yl)-11-oxoundecyl)oxy)-2-(2,6-dioxopiperidin-3-yl)isoindoline-1,3-dione(5)

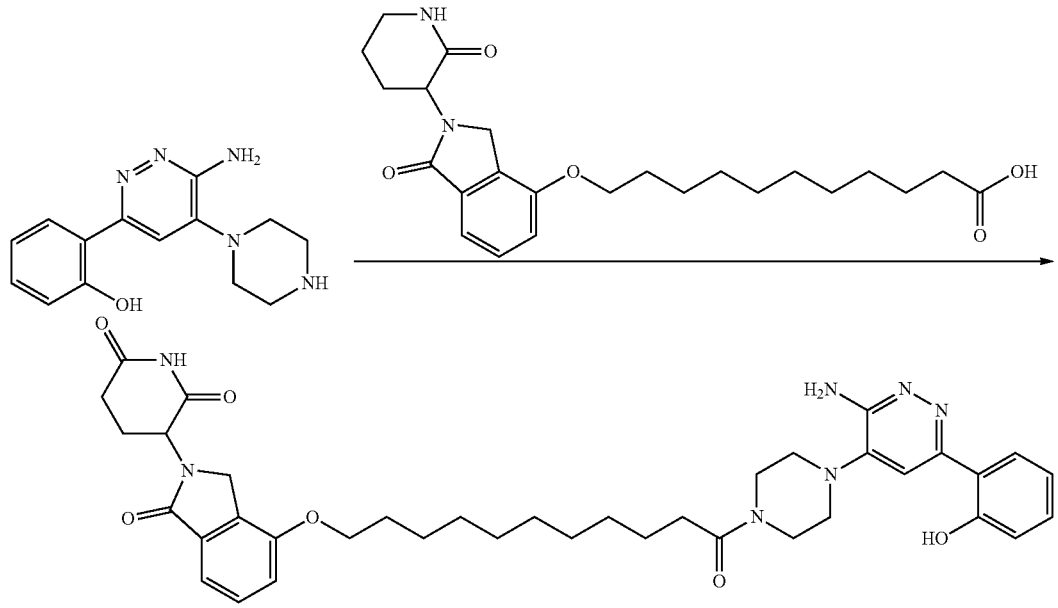

5

A mixture of 2-(6-amino-5-(piperazin-1-yl)pyridazin-3-yl)phenol (16 mg, 0.052 mmol), 11-((2-(2,6-dioxopiperidin-3-yl)-1,3-dioxoisoindolin-4-yl)oxy)undecanoic acid (24 mg, 0.052 mmol) in DMF (1 mL) was added HATU (30 mg, 0.078 mmol) and DIPEA (0.05 mL, 0.26 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 6.9 mg, yield 19%). LCMS (m/z): 712 [M+H]$^+$. $^1$H NMR (500 MHz, DMSO-d$_6$) δ 14.09 (s, 1H), 11.03 (s, 1H), 7.84 (dd, J=8.5, 1.6 Hz, 1H), 7.73 (dd, J=8.6, 7.2 Hz, 1H), 7.48-7.40 (m, 2H), 7.37 (d, J=7.2 Hz, 1H), 7.17 (td, J=7.7, 1.6 Hz, 1H), 6.85-6.78 (m, 2H), 6.33 (s, 2H), 5.01 (dd, J=12.8, 5.4 Hz, 1H), 4.12 (t, J=6.4 Hz, 2H), 3.61 (t, J=5.2 Hz, 4H), 2.99 (dd, J=21.3, 5.3 Hz, 4H), 2.81 (ddd, J=16.8, 13.8, 5.4 Hz, 1H), 2.56-2.38 (m, 2H), 2.27 (t, J=7.5 Hz, 2H), 2.03-1.91 (m, 1H), 1.68 (p, J=6.6 Hz, 2H), 1.44 (s, 2H), 1.37 (q, J=7.2 Hz, 2H), 1.27 (s, 2H), 1.24-1.20 (m, 8H).

Example 6: Synthesis of 4-((8-(4-(3-amino-6-(2-hydroxyphenyl)pyridazin-4-yl)piperazin-1-yl)-8-oxooctyl)oxy)-2-(2,6-dioxopiperidin-3-yl)isoindoline-1,3-dione (6)

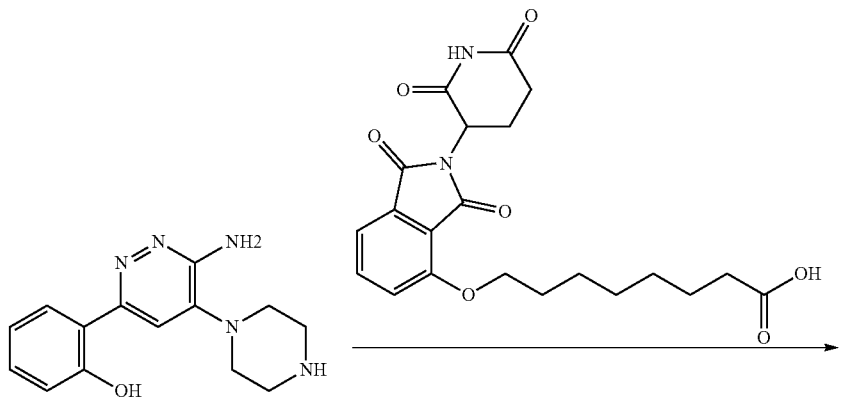

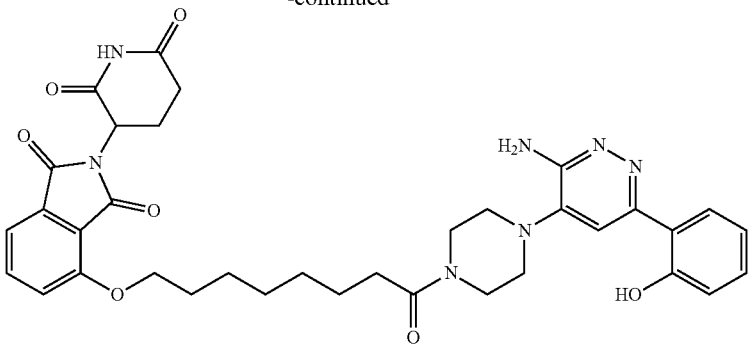

A mixture of 2-(6-amino-5-(piperazin-1-yl)pyridazin-3-yl)phenol (16 mg, 0.052 mmol), 8-((2-(2,6-dioxopiperidin-3-yl)-1,3-dioxoisoindolin-4-yl)oxy)octanoic acid (22 mg, 0.052 mmol) in DMF (1 mL) was added HATU (30 mg, 0.078 mmol) and DIPEA (0.05 mL, 0.26 mmol). The reaction mixture was stirred at rt overnight. After completion, the mixture was extracted with EA (50 mL×3), the organic phase was washed with brine (20 mL×3), dried with $Na_2SO_4$, filtered, concentrated to remove the solvent, the residue was purified by prep-HPLC to obtain the target compound (white solid, 7.7 mg, yield 22%). LCMS (m/z): 670 [M+H]$^+$. $^1$H NMR (500 MHz, DMSO-d$_6$) δ 11.02 (s, 1H), 7.73 (dd, J=8.5, 7.2 Hz, 1H), 7.53 (dd, J=7.8, 1.7 Hz, 1H), 7.47-7.39 (m, 2H), 7.37 (d, J=7.2 Hz, 1H), 7.35-7.28 (m, 1H), 6.96 (d, J=8.3 Hz, 1H), 6.91 (t, J=7.5 Hz, 1H), 5.00 (dd, J=12.8, 5.4 Hz, 1H), 4.13 (t, J=6.4 Hz, 2H), 3.61 (m, 7H), 3.18 (m, 4H), 2.81 (m, 1H), 2.56-2.44 (m, 1H), 2.42 (m, 1H), 2.29 (t, J=7.4 Hz, 2H), 1.95 (m, 1H), 1.69 (m, 2H), 1.46 (m, 2H), 1.39 (m, 2H), 1.34-1.22 (m, 4H).

Example 7: Synthesis of 4-((7-(4-(3-amino-6-(2-hydroxyphenyl)pyridazin-4-yl)piperazin-1-yl)-7-oxoheptyl)oxy)-2-(2,6-dioxopiperidin-3-yl)isoindoline-1,3-dione (7)

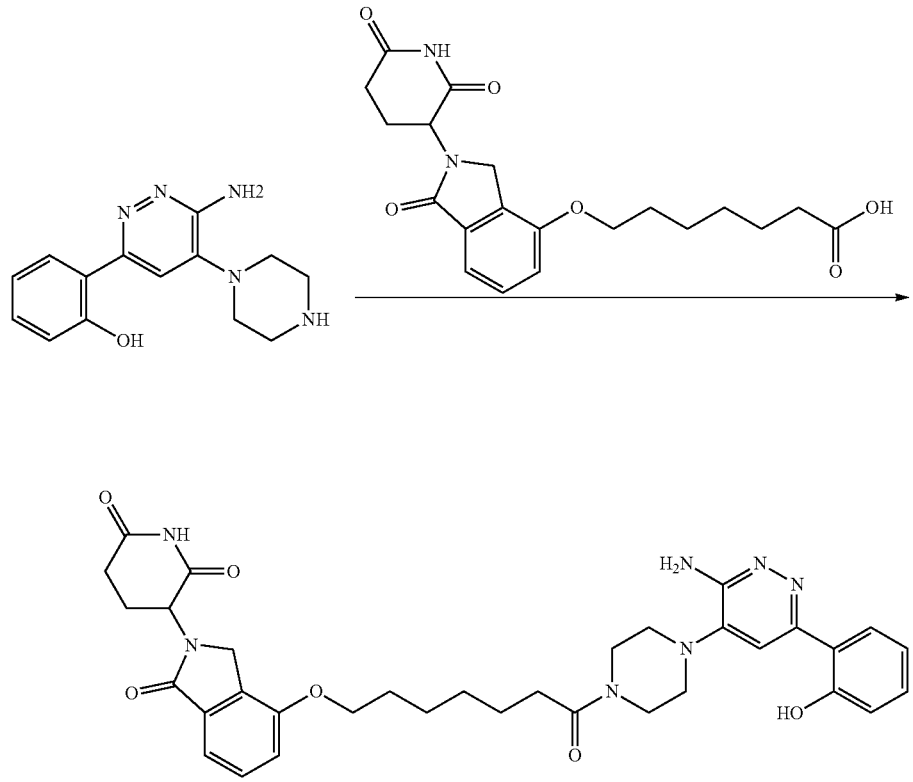

A mixture of 2-(6-amino-5-(piperazin-1-yl)pyridazin-3-yl)phenol (15 mg, 0.049 mmol), 7-((2-(2,6-dioxopiperidin-3-yl)-1,3-dioxoisoindolin-4-yl)oxy)heptanoic acid (20 mg, 0.049 mmol) in DMF (1 mL) was added HATU (28 mg, 0.074 mmol) and DIPEA (0.05 mL, 0.26 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 7.5 mg, yield 23%). LCMS (m/z): 656 [M+H]$^+$. $^1$H NMR (500 MHz, DMSO-d$_6$) δ 11.10 (s, 1H), 7.81 (t, J=7.9 Hz, 1H), 7.61-7.54 (m, 1H), 7.52 (d, J=8.5 Hz, 1H), 7.48 (s, 1H), 7.45 (d, J=7.2 Hz, 1H), 7.40 (t, J=7.8 Hz, 1H), 7.07-6.96 (m, 2H), 5.08 (dd, J=12.9, 5.4 Hz, 1H), 4.21 (t, J=6.4 Hz, 4H), 3.69 (t, J=4.7 Hz, 4H), 3.29 (s, 1H), 3.24 (s, 1H), 3.10 (m, 1H), 2.93-2.82 (m, 2H), 2.62-2.52 (m, 2H), 2.38 (t, J=7.4 Hz, 2H), 2.03 (m, 1H), 1.77 (m, 2H), 1.52 (m, 4H), 1.38 (m, 2H), 1.18 (m, 1H).

Example 8: Synthesis of 4-((10-(4-(3-amino-6-(2-hydroxyphenyl)pyridazin-4-yl)piperazin-1-yl)-10-oxodecyl)oxy)-2-(2,6-dioxopiperidin-3-yl)isoindoline-1,3-dione (8)

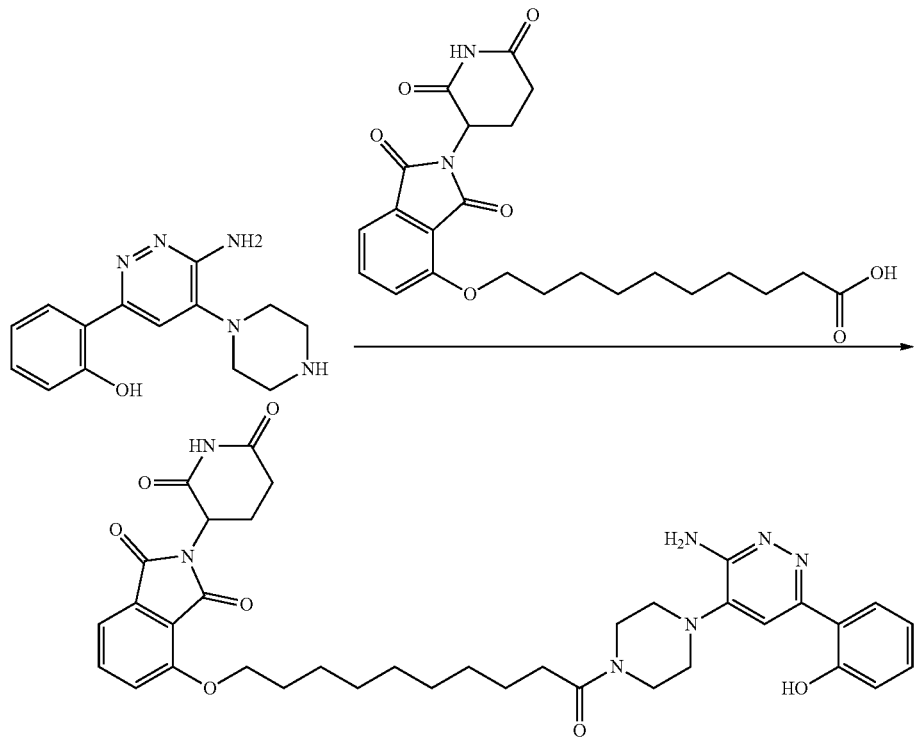

8

A mixture of 2-(6-amino-5-(piperazin-1-yl)pyridazin-3-yl)phenol (15 mg, 0.049 mmol), 10-((2-(2,6-dioxopiperidin-3-yl)-1,3-dioxoisoindolin-4-yl)oxy)decanoic acid (22 mg, 0.049 mmol) in DMF (1 mL) was added HATU (28 mg, 0.074 mmol) and DIPEA (0.05 mL, 0.26 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 14.7 mg, yield 43%). LCMS (m/z): 698 [M+H]$^+$. $^1$H NMR (500 MHz, DMSO-d$_6$) δ 14.17 (s, 1H), 11.10 (s, 1H), 7.94-7.89 (m, 1H), 7.80 (dd, J=8.5, 7.2 Hz, 1H), 7.55-7.48 (m, 2H), 7.44 (d, J=7.3 Hz, 1H), 7.24 (td, J=7.6, 1.6 Hz, 1H), 6.89 (m, 2H), 6.41 (s, 2H), 5.08 (dd, J=12.8, 5.5 Hz, 1H), 4.20 (t, J=6.4 Hz, 2H), 3.69 (m, 4H), 3.18 (m, 1H), 3.06 (m, 4H), 2.89 (m, 1H), 2.64-2.51 (m, 2H), 2.35 (t, J=7.5 Hz, 2H), 2.03 (m, 1H), 1.76 (m, 2H), 1.49 (m, 4H), 1.33 (m, 7H).

Example 9: Synthesis of 3-(4-(6-(4-(3-amino-6-(2-hydroxyphenyl)pyridazin-4-yl)piperazin-1-yl)-6-oxohex-1-yn-1-yl)-1-oxoisoindolin-2-yl)piperidine-2,6-dione (9)

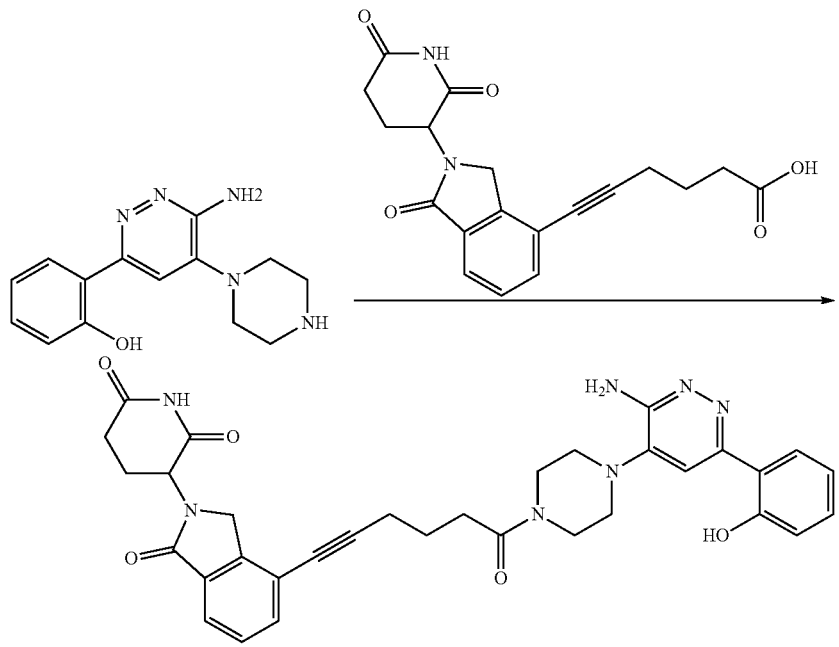

The mixture of 2-(6-amino-5-(piperazin-1-yl)pyridazin-3-yl)phenol (15 mg, 0.049 mmol), 6-(2-(2,6-dioxopiperidin-3-yl)-1-oxoisoindolin-4-yl)hex-5-ynoic acid (17 mg, 0.049 mmol) in DMF (1 mL) was added HATU (28 mg, 0.074 mmol) and DIPEA (0.05 mL, 0.26 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 9 mg, yield 15%). LCMS (m/z): 608 [M+H]$^+$. $^1$H NMR (500 MHz, DMSO-d$_6$) δ 14.17 (s, 1H), 10.99 (s, 1H), 7.92 (dd, J=8.4, 1.6 Hz, 1H), 7.57 (m, 1H), 7.53 (s, 1H), 7.50-7.42 (m, 2H), 7.25 (td, J=7.5, 1.6 Hz, 1H), 6.89 (m, 2H), 6.41 (s, 2H), 5.14 (dd, J=13.3, 5.1 Hz, 1H), 4.48 (d, J=17.1 Hz, 1H), 4.33 (d, J=17.1 Hz, 1H), 3.68 (s, 4H), 3.13-2.98 (m, 4H), 2.66 (t, J=7.7 Hz, 2H), 2.37 (t, J=7.4 Hz, 2H), 1.62 (m, 4H), 1.45-1.29 (m, 2H).

Example 10: Synthesis of 3-(4-(6-(4-(3-amino-6-(2-hydroxyphenyl)pyridazin-4-yl)piperazin-1-yl)-6-oxohexyl)-1-oxoisoindolin-2-yl)piperidine-2,6-dione (10)

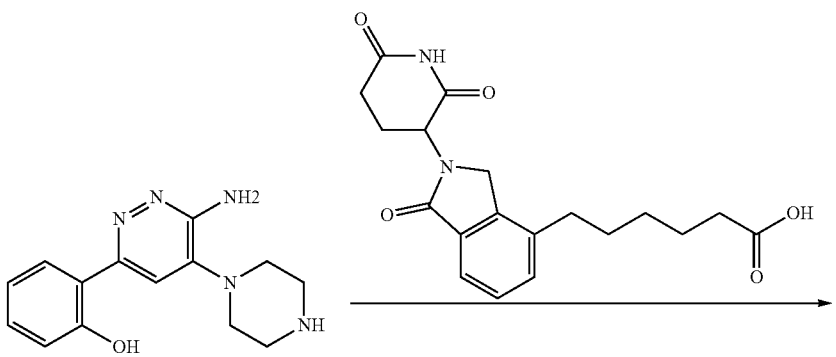

-continued

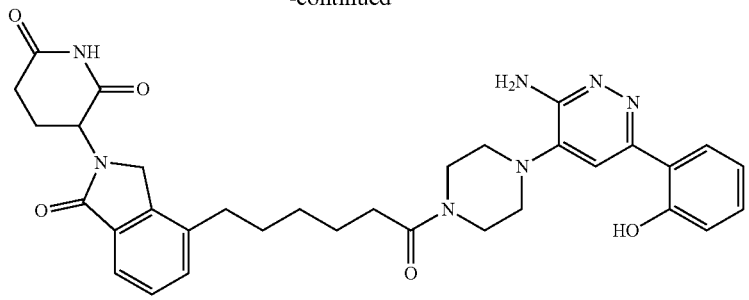

10

The mixture of 2-(6-amino-5-(piperazin-1-yl)pyridazin-3-yl)phenol (15 mg, 0.049 mmol), 6-(2-(2,6-dioxopiperidin-3-yl)-1-oxoisoindolin-4-yl)hexanoic acid (18 mg, 0.049 mmol) in DMF (1 mL) was added HATU (28 mg, 0.074 mmol) and DIPEA (0.05 mL, 0.26 mmol). The reaction mixture was stirred at rt overnight. After completion, the mixture was extracted with EA (50 mL×3), the organic phase was washed with brine (20 mL×3), dried with Na₂SO₄, filtered, concentrated to remove the solvent, the residue was purified by prep-HPLC to obtain the target compound (white solid, 12 mg, yield 20%). LCMS (m/z): 612 [M+H]⁺. ¹H NMR (500 MHz, DMSO-d6) δ 14.16 (s, 1H), 11.00 (s, 1H), 7.90 (dd, J=8.5, 1.6 Hz, 1H), 7.72 (dd, J=7.6, 1.0 Hz, 1H), 7.67 (dd, J=7.7, 1.0 Hz, 1H), 7.56-7.46 (m, 2H), 7.28-7.20 (m, 1H), 6.89 (m, 2H), 6.41 (s, 2H), 5.15 (dd, J=13.3, 5.1 Hz, 1H), 4.49 (d, J=17.7 Hz, 1H), 4.34 (d, J=17.7 Hz, 1H), 3.71 (t, J=5.0 Hz, 4H), 3.18 (d, J=5.1 Hz, 1H), 3.07 (dt, J=21.7, 4.9 Hz, 4H), 2.91 (m, 1H), 2.63-2.53 (m, 5H), 2.46 (m, 1H), 2.01 (m, 1H), 1.86 (m, 2H).

Example 11: Synthesis of 4-((9-(4-(3-amino-6-(2-hydroxyphenyl)pyridazin-4-yl)piperazin-1-yl)-9-oxononyl)oxy)-2-(1-methyl-2,6-dioxopiperidin-3-yl)isoindoline-1,3-dione(Compound G)

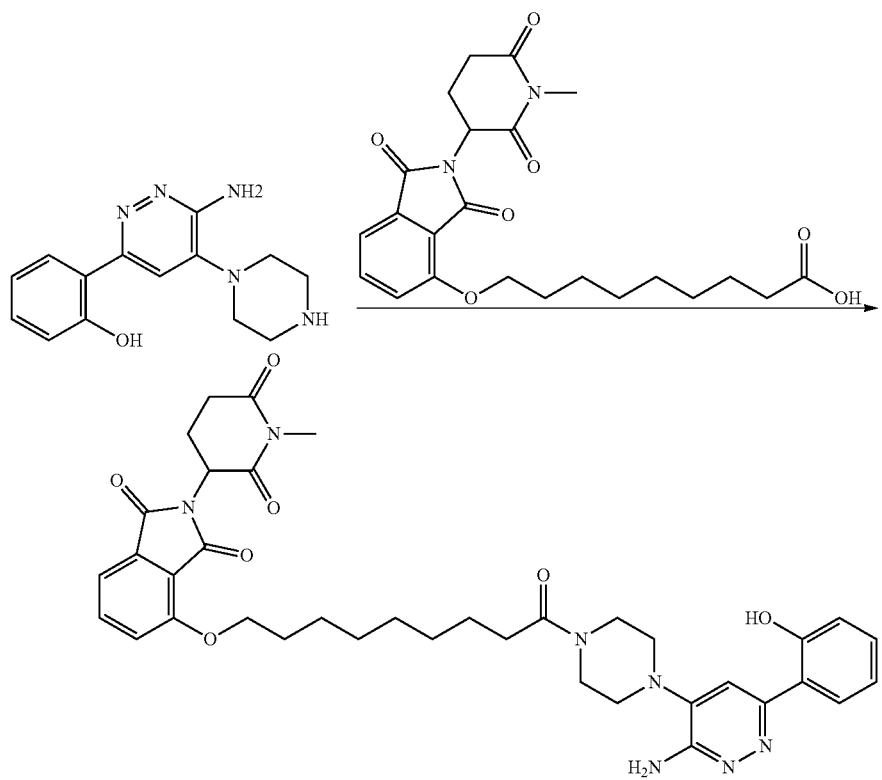

Compound G

The mixture of 2-(6-amino-5-(piperazin-1-yl)pyridazin-3-yl)phenol (14 mg, 0.045 mmol), 9-((2-(1-methyl-2,6-dioxopiperidin-3-yl)-1,3-dioxoisoindolin-4-yl)oxy)nonanoic acid (20 mg, 0.045 mmol) in DMF (1 mL) was added HATU (26 mg, 0.07 mmol) and DIPEA (0.03 mL, 0.16 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 5.3 mg, yield 17%). LCMS (m/z): 698 [M+H]$^+$. $^1$H NMR (500 MHz, DMSO-d$_6$) δ 7.81 (dd, J=8.5, 7.2 Hz, 1H), 7.61 (dd, J=7.8, 1.7 Hz, 1H), 7.56-7.47 (m, 2H), 7.45 (d, J=7.3 Hz, 1H), 7.42-7.25 (m, 1H), 7.03 (d, J=8.2 Hz, 1H), 6.98 (t, J=7.5 Hz, 1H), 5.15 (dd, J=13.0, 5.4 Hz, 1H), 4.20 (t, J=6.4 Hz, 2H), 3.68 (m, 4H), 3.25 (m, 4H), 3.02 (s, 3H), 2.95 (m, J=17.2, 13.9, 5.4 Hz, 1H), 2.76 (ddd, J=17.2, 4.5, 2.5 Hz, 1H), 2.60-2.51 (m, 4H), 2.35 (t, J=7.5 Hz, 2H), 2.05 (dtd, J=13.1, 5.4, 2.6 Hz, 1H), 1.81-1.72 (m, 2H), 1.57-1.41 (m, 4H), 1.32 (m, 6H).

Example 12: (2S,4R)-1-((S)-2-(9-(4-(3-amino-6-(2-hydroxyphenyl)pyridazin-4-yl)piperazin-1-yl)nonanamido)-3,3-dimethylbutanoyl)-4-hydroxy-N—((S)-1-(4-(4-methylthiazol-5-yl)phenyl)ethyl)pyrrolidine-2-carboxamide (11)

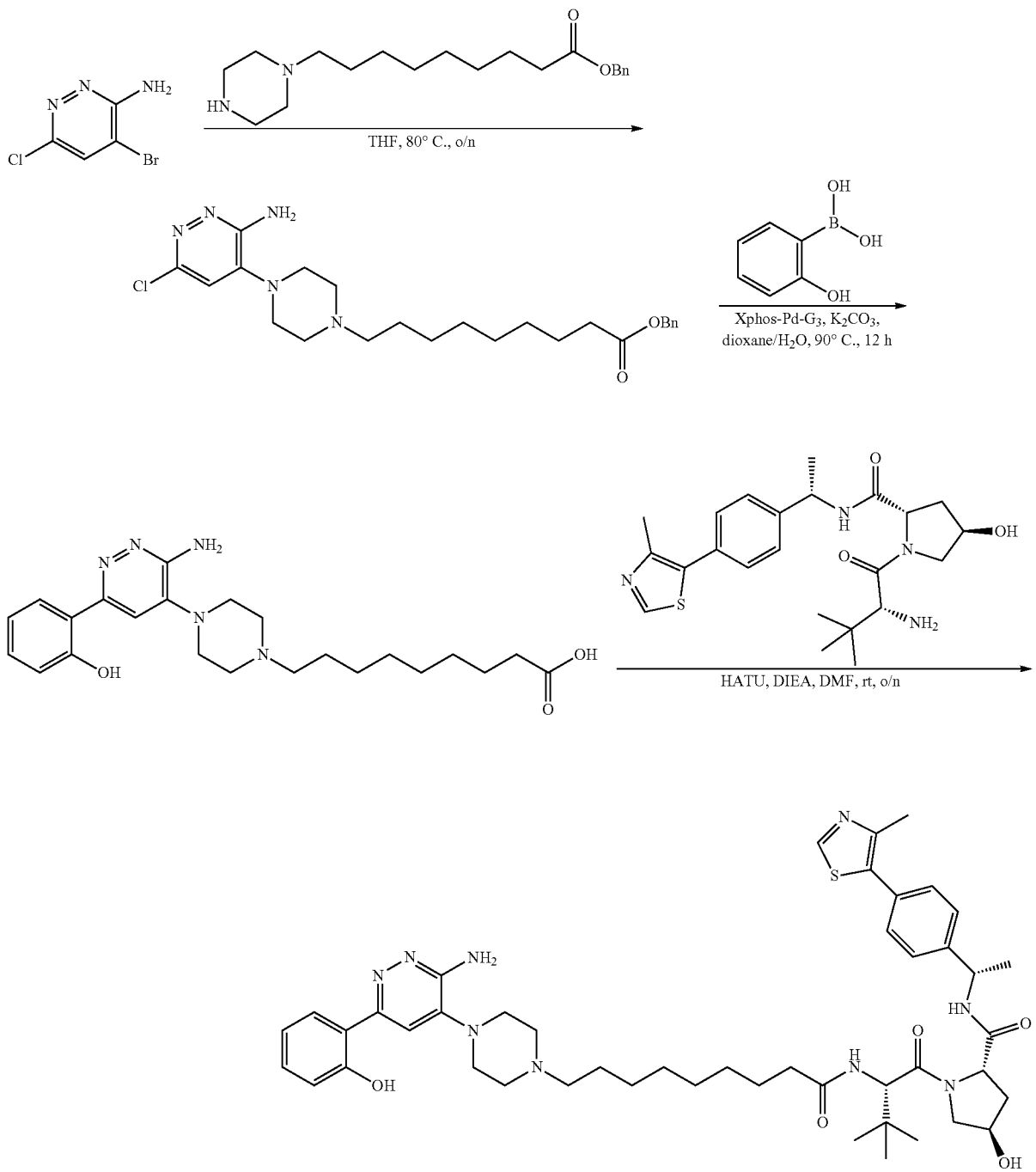

Benzyl 9-(4-(3-amino-6-chloropyridazin-4-yl)piperazin-1-yl)nonanoate

To a solution of 4-bromo-6-chloropyridazin-3-amine (208 mg, 1 mmol) in MeCN (5 mL) was added benzyl 9-(piperazin-1-yl)nonanoate (400 mg, 1.2 mmol) and DIEA (650 mg, 5 mmol). The reaction mixture was stirred in a seal tube at 100° C. overnight. The reaction mixture was cooled and concentrated. The residue was purified with sil gel column to give the desire product (180 mg, yield 39%). LCMS (m/z): 460 [M+H]$^+$.

9-(4-(3-Amino-6-(2-hydroxyphenyl)pyridazin-4-yl)piperazin-1-yl)nonanoic Acid To a solution of benzyl 9-(4-(3-amino-6-chloropyridazin-4-yl)piperazin-1-yl)nonanoate (180 mg, 0.4 mmol) in dioxane/H2O (10 mL/1 mL) was added (2-hydroxyphenyl)boronic acid (73 mg, 0.53 mmol), Xphos-Pd-G3 (34 mg, 0.04 mmol) and K$_2$CO$_3$ (110 mg, 0.8 mmol). The reaction mixture was stirred at 90° C. overnight with N$_2$ protected. The reaction mixture was cooled and concentrated. The residue was purified with sil gel column to give the desire product (54 mg, yield 32%). LCMS (m/z): 428 [M+H]$^+$.

(2S,4R)-1-((S)-2-(9-(4-(3-amino-6-(2-hydroxyphenyl)pyridazin-4-yl)piperazin-1-yl)nonanamido)-3,3-dimethylbutanoyl)-4-hydroxy-N—((S)-1-(4-(4-methylthiazol-5-yl)phenyl)ethyl)pyrrolidine-2-carboxamide The mixture of (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (8 mg, 0.017 mmol), 9-(4-(3-amino-6-(2-hydroxyphenyl)pyridazin-4-yl)piperazin-1-yl)nonanoic acid (9 mg, 0.017 mmol) in DMF (0.5 mL) was added HATU (9.5 mg, 0.025 mmol) and DIPEA (0.01 mL, 0.05 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 7.8 mg, yield 55%). LCMS (m/z): 854 [M+H]$^+$. $^1$H NMR (500 MHz, DMSO-d$_6$) δ 10.03 (s, 1H), 9.05 (s, 1H), 8.43 (d, J=7.8 Hz, 1H), 7.84 (d, J=9.3 Hz, 1H), 7.74 (d, J=7.8 Hz, 1H), 7.67 (s, 1H), 7.59-7.26 (m, 7H), 7.14-6.96 (m, 2H), 5.09-4.84 (m, 2H), 4.58 (d, J=9.3 Hz, 1H), 4.48 (t, J=8.1 Hz, 1H), 4.39-4.30 (m, 1H), 3.92-3.78 (m, 4H), 3.23-3.12 (m, 4H), 2.51 (s, 3H), 2.37-2.27 (m, 1H), 2.22-1.94 (m, 3H), 1.90-1.81 (m, 1H), 1.79-1.67 (m, 2H), 1.64-1.47 (m, 3H), 1.44 (d, J=7.0 Hz, 3H), 1.41-1.17 (m, 10H), 0.99 (d, J=7.1 Hz, 9H).

Example 13: (2S,4R)-1-((S)-2-(9-(4-(3-Amino-6-(2-hydroxyphenyl)pyridazin-4-yl)piperazin-1-yl)-9-oxonononanamido)-3,3-dimethylbutanoyl)-4-hydroxy-N—((S)-1-(4-(4-methylthiazol-5-yl)phenyl)ethyl)pyrrolidine-2-carboxamide (12)

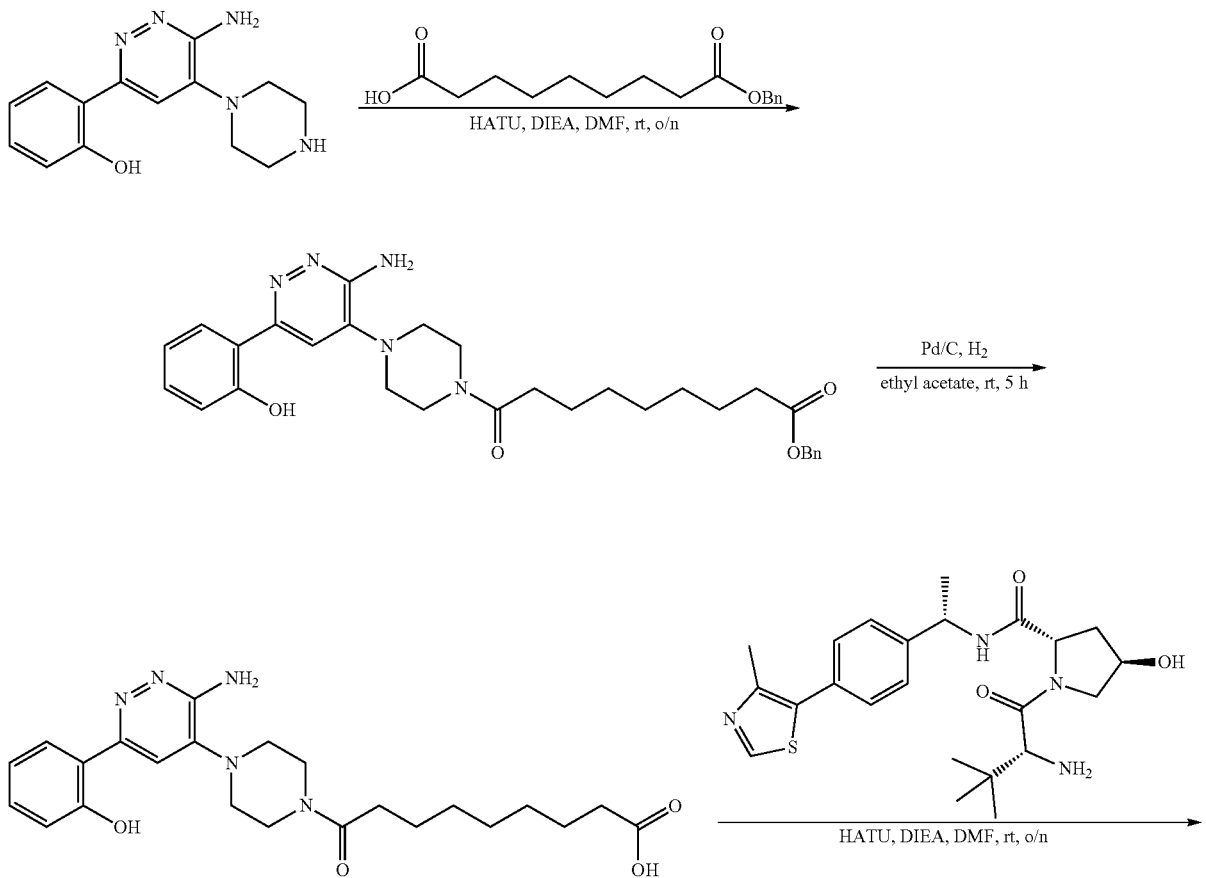

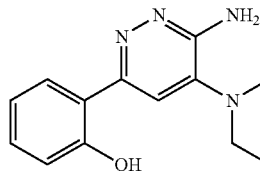
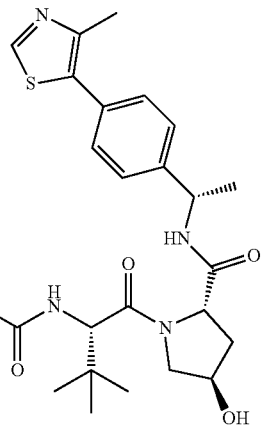

12

Benzyl 9-(4-(3-amino-6-(2-hydroxyphenyl)pyridazin-4-yl)piperazin-1-yl)-9-oxononanoate The mixture of 2-(6-amino-5-(piperazin-1-yl)pyridazin-3-yl)phenol (77 mg, 0.28 mmol), 9-(benzyloxy)-9-oxononanoic acid (56 mg, 0.2 mmol) in DMF (2 mL) was added HATU (114 mg, 0.3 mmol) and DIPEA (0.11 mL, 0.6 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 67 mg, yield 63%). LCMS (m/z): 531 [M+H]$^+$.

9-(4-(3-Amino-6-(2-hydroxyphenyl)pyridazin-4-yl)piperazin-1-yl)-9-oxononanoic Acid To a solution of benzyl 9-(4-(3-amino-6-(2-hydroxyphenyl)pyridazin-4-yl)piperazin-1-yl)-9-oxononanoate (67 mg, 0.13 mmol) in ethyl acetate (5 mL) was added Pd/C (10 mg, 10% w/t). The reaction mixture was stirred under H2 at rt for 5 hours. After completion, the mixture was filtered and then concentrated to obtain the target compound (white solid, 54 mg, yield 94%). LCMS (m/z): 442 [M+H]$^+$.

(2S,4R)-1-((S)-2-(9-(4-(3-Amino-6-(2-hydroxyphenyl)pyridazin-4-yl)piperazin-1-yl)-9-oxononanamido)-3,3-dimethylbutanoyl)-4-hydroxy-N—((S)-1-(4-(4-methylthiazol-5-yl)phenyl)ethyl)pyrrolidine-2-carboxamide The mixture of (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (8 mg, 0.017 mmol), 9-(4-(3-amino-6-(2-hydroxyphenyl)pyridazin-4-yl)piperazin-1-yl)-9-oxononanoic acid (10 mg, 0.017 mmol) in DMF (0.5 mL) was added HATU (10 mg, 0.025 mmol) and DIPEA (0.01 mL, 0.05 mmol). The reaction mixture was stirred at rt overnight. After completion, the mixture was extracted with EA (50 mL×3), the organic phase was washed with brine (20 mL×3), dried with Na$_2$SO$_4$, filtered, concentrated to remove the solvent, the residue was purified by prep-HPLC to obtain the target compound (white solid, 11.6 mg, yield 79%). LCMS (m/z): 868 [M+H]$^+$. $^1$H NMR (500 MHz, DMSO-d$_6$) δ 9.05 (s, 1H), 8.43 (d, J=7.7 Hz, 1H), 7.84 (d, J=9.3 Hz, 1H), 7.67-7.31 (m, 9H), 7.20-6.91 (m, 2H), 5.07-4.85 (m, 2H), 4.57 (d, J=9.3 Hz, 1H), 4.48 (t, J=8.0 Hz, 1H), 4.38-4.30 (m, 1H), 3.44-3.17 (m, 9H), 2.51 (s, 3H), 2.41 (t, J=7.5 Hz, 2H), 2.35-2.26 (m, 1H), 2.22-2.12 (m, 1H), 2.12-2.02 (m, 1H), 1.89-1.80 (m, 1H), 1.62-1.48 (m, 5H), 1.43 (d, J=7.0 Hz, 3H), 1.37-1.25 (m, 7H), 0.99 (s, 9H).

Example 14: N-(6-(4-(3-amino-6-(2-hydroxyphenyl)pyridazin-4-yl)piperazin-1-yl)hexyl)-2-((2-2,6-dioxopiperidin-3-1l)-1,3-dioxoisoindolin-4-yl)oxy)acetamide (13)

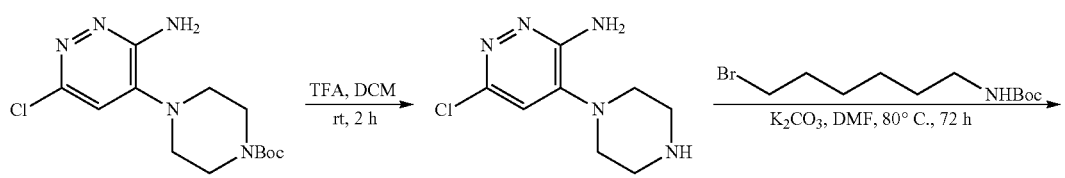

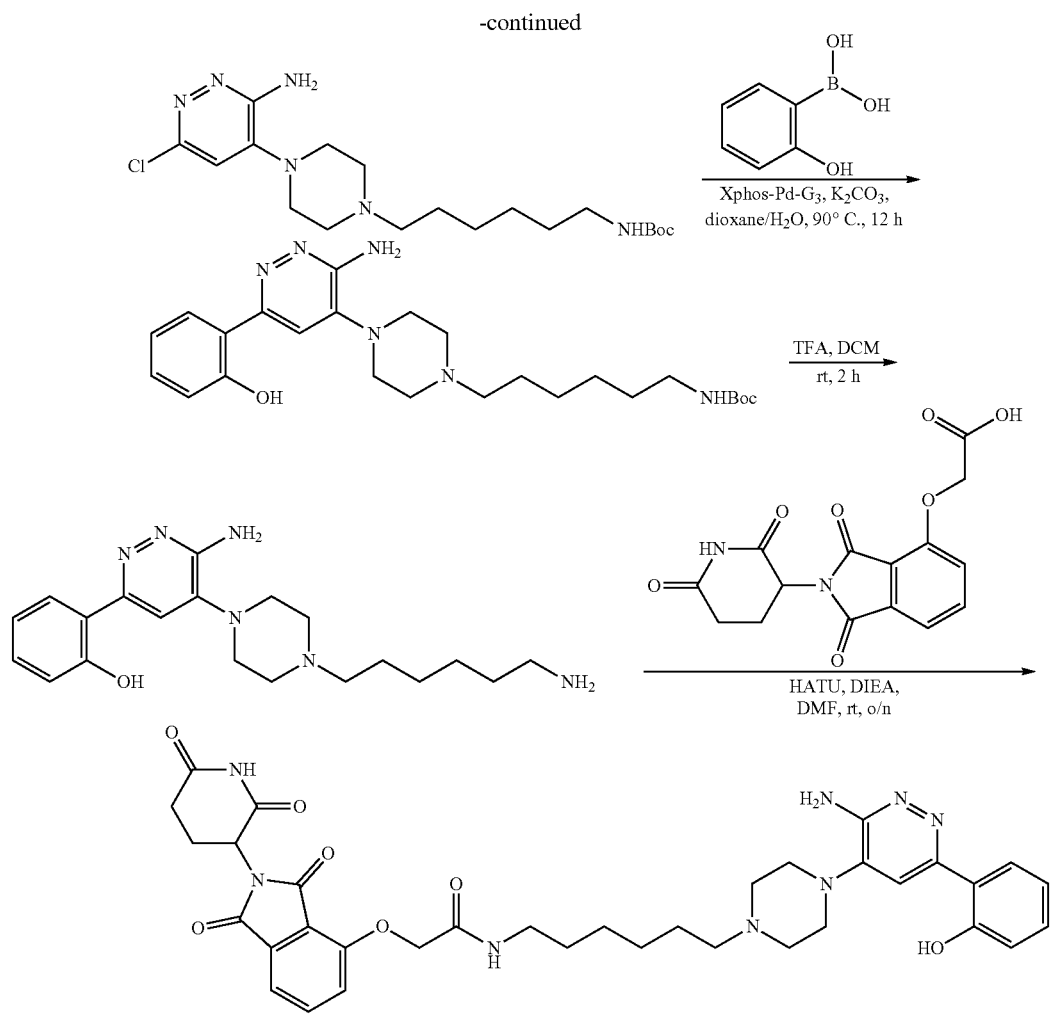

6-Chloro-4-(piperazin-1-yl)pyridazin-3-amine

To a solution of tert-butyl 4-(3-amino-6-chloropyridazin-4-yl)piperazine-1-carboxylate (157 mg, 0.5 mmol) in DCM (5 mL) was added TFA (2 mL). The reaction mixture was stirred at rt for 2 h. The reaction mixture was concentrated to give the desire product (100 mg, 61%) as TFA salt. LCMS (m/z): 214 [M+H]$^+$.

Tert-butyl (6-(4-(3-amino-6-chloropyridazin-4-yl)piperazin-1-yl)hexyl)carbamate To a solution of 6-Chloro-4-(piperazin-1-yl)pyridazin-3-amine (100 mg, TFA salt, 0.3 mmol) in DMF (3 mL) was added tert-butyl (6-bromohexyl)carbamate (110 mg, 0.39 mmol) and K$_2$CO$_3$ (83 mg, 0.6 mmol). The reaction mixture was stirred at 60° C. for 72 h, then cooled and concentrated. The residue was purified with sil gel column to give the desire product (95 mg, yield 77%). LCMS (m/z): 413 [M+H]$^+$.

Tert-butyl (6-(4-(3-amino-6-(2-hydroxyphenyl)pyridazin-4-yl)piperazin-1-yl)hexyl)carbamate To a solution of tert-butyl (6-(4-(3-amino-6-chloropyridazin-4-yl)piperazin-1-yl)hexyl) carbamate (95 mg, 0.23 mmol) in dioxane/H$_2$O (10 mL/1 mL) was added (2-hydroxy phenyl)boronic acid (42 mg, 0.3 mmol), Xphos-Pd-G3 (20 mg, 0.023 mmol) and K$_2$CO$_3$ (64 mg, 0.46 mmol). The reaction mixture was stirred at 90° C. overnight with N2 protected. The reaction mixture was cooled and concentrated. The residue was purified with prep-HPLC to give the desire product (60 mg, yield 55%). LCMS (m/z): 471 [M+H]$^+$.

2-(6-amino-5-(4-(6-aminohexyl)piperazin-1-yl)pyridazin-3-yl)phenol

To a solution of tert-butyl (6-(4-(3-amino-6-(2-hydroxy-phenyl)pyridazin-4-yl)piperazin-1-yl)hexyl)carbamate (60 mg, 0.13 mmol) in DCM (5 mL) was added TFA (2 mL). The reaction mixture was stirred at rt for 2 h. The reaction mixture was concentrated to give the desire product (50 mg, 79%) as TFA salt. LCMS (m/z): 371 [M+H]$^+$.

N-(6-(4-(3-amino-6-(2-hydroxyphenyl)pyridazin-4-yl)piperazin-1-yl)hexyl)-2-((2-(2,6-dioxopiperidin-3-yl)-1,3-dioxoisoindolin-4-yl)oxy)acetamide The mixture of 2-(6-amino-5-(4-(6-aminohexyl)piperazin-1-yl)pyridazin-3-yl)phenol (25 mg, TFA salt, 0.05 mmol), 2-((2-(2,6-dioxopiperidin-3-yl)-1,3-dioxoisoindolin-4-yl)oxy) acetic acid (17 mg, 0.05 mmol) in DMF (0.5 mL) was added HATU (29 mg, 0.075 mmol) and DIPEA (0.05 mL, 0.25 mmol). The reaction mixture was stirred at rt overnight. After completion, the mixture was extracted with EA (50 mL×3), the organic phase was washed with brine (20 mL×3), dried with Na2SO4, filtered, concentrated to remove the solvent, the residue was purified by prep-HPLC to obtain the target compound (white solid, 13.1 mg, yield 38%). LCMS (m/z): 685 [M+H]$^+$. $^1$H NMR (500 MHz, DMSO-d$_6$) δ 11.12 (s, 1H), 9.98 (s, 1H), 7.98 (t, J=5.7 Hz, 1H), 7.86-7.77 (m, 1H), 7.68 (d, J=7.7 Hz, 1H), 7.61 (s, 1H), 7.55-7.33 (m, 5H), 7.07-6.95 (m, 2H), 5.16-5.07 (m, 1H), 4.78 (s, 2H), 3.26-3.07 (m, 8H), 2.99-2.81 (m, 2H), 2.17-1.93 (m, 2H), 1.76-1.57 (m, 2H), 1.55-1.42 (m, 2H), 1.41-1.30 (m, 4H), 1.30-1.16 (m, 4H).

Example 15: Cellular CRBN Binding Assay

BRD4$_{BD2}$ were subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using the Flip-In™ 293 system. Plasmid (0.3 µg) and pOG44 (4.7 µg) DNA were preincubated in 100 µl of Opti-MEM I (Gibco™, Life Technologies) media containing 0.05 mg/ml Lipofectamine® 2000 (Invitrogen) for 20 minutes and added to Flip-In™ 293 cells containing 1.9 ml of DMEM media (Gibco™, Life Technologies) per well in a 6-well plate format (Falcon, 353046). Cells were propagated after 48 hours and transferred into a 10 cm$^2$ plate (Corning, 430165) in DMEM media containing 50 µg/ml of Hygromycin B (REF 10687010, Invitrogen) as a selection marker. Following a 2-3 passage cycle, FACS (FACSAria II, BD) was used to enrich for cells expressing eGFP and mCherry.

Cells stably expressing BRD4$_{BD2}$-GFP with mCherry reporter were seeded at 30-50% confluency in 384 well plates (3764, Corning) with 50 µl FluoroBrite DMEM media (Gibco™, A18967) containing 10% FBS per well a day before compound treatment. Compounds and 100 nM dBET6 were dispensed using D300e Digital Dispenser (HP) normalized to 0.5% DMSO and incubated with cells for 5 hours. The assay plate was imaged immediately using Acumen eX3/HCI (TTPLabtech) High Content Imager with 488 nm and 561 nm lasers in 2 m×1 m grid per well format. The resulting images were analyzed using CellProfiler (Carpenter, et al., Genome Biol. 7:R100 PIMD 17076895 (2006)).

Figure 1B:
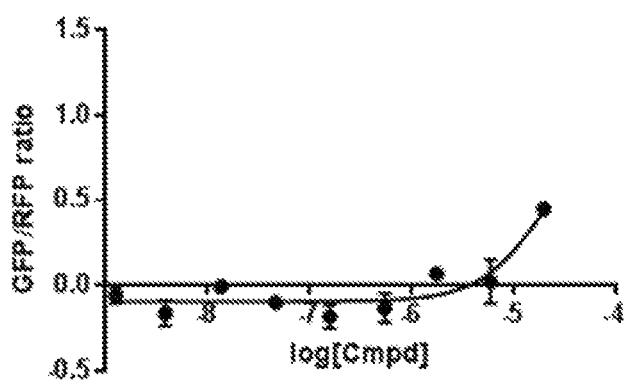
Figure 1C:
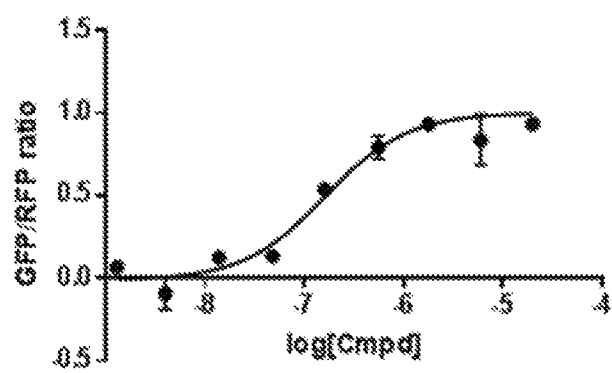

The results are shown in FIG. 1A-FIG. 1C. The IC$_{50}$ for Compound 1 is 0.00003047 (FIG. 1A); the IC$_{50}$ for Compound 2 is 0.00002086 (FIG. 1B); and the IC$_{50}$ for Compound 3 is 0.0000001623 (FIG. 1C). The results indicate that compounds carrying PEG-based linkers (FIG. 1A and FIG. 1B) were less permeable than the carbon-only (alkylene) compound (FIG. 1C).

Example 16: PBRM1 PB5 GFP/RFP Degradation Assay

Cellular Degradation Assay

PBRM1 PB5 was subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using the Flip-In™ 293 system. Plasmid (0.3 g) and pOG44 (4.7 g) DNA were preincubated in 100 µl of Opti-MEM I (Gibco™, Life Technologies) media containing 0.05 mg/ml Lipofectamine 2000 (Invitrogen) for 20 minutes and added to Flip-In™ 293 cells containing 1.9 ml of DMEM media (Gibco™, Life Technologies) per well in a 6-well plate format (Falcon, 353046). Cells were propagated after 48 hours and transferred into a 10 cm$^2$ plate (Corning, 430165) in DMEM media containing 50 µg/ml of Hygromycin B (REF 10687010, Invitrogen) as a selection marker. Following a 2-3 passage cycle, FACS (FACSAria II, BD) was used to enrich for cells expressing eGFP and mCherry.

Cells were seeded at 30-50% confluency in either 24, 48 or 96 well plates (3524, 3548, 3596, respectively, Costar) a day before compound treatment. Titrated compounds were incubated with cells for 5 hours following trypsinization and resuspension in DMEM media, transferred into 96-well plates (353910, Falcon) and analyzed by flow cytometer (guava easyCyte HT, Millipore). Signal from minimal 3000 events per well was acquired and the eGFP and mCherry florescence were monitored. Data was analyzed using FlowJo® (FlowJo, LLC). Forward and side scatter outliers, frequently associated with cell debris, were removed leaving >90% of total cells, followed by removal of eGFP and mCherry signal outliers, leaving 88-90% of total cells creating the set used for quantification. The eGFP protein abundance relative to mCherry was then quantified as a ten-fold amplified ratio for each individual cell using the formula: 10×eGFP/mCherry. The median of the ratio was then calculated per set, normalized to the median of the DMSO ratio.

Figure 2:
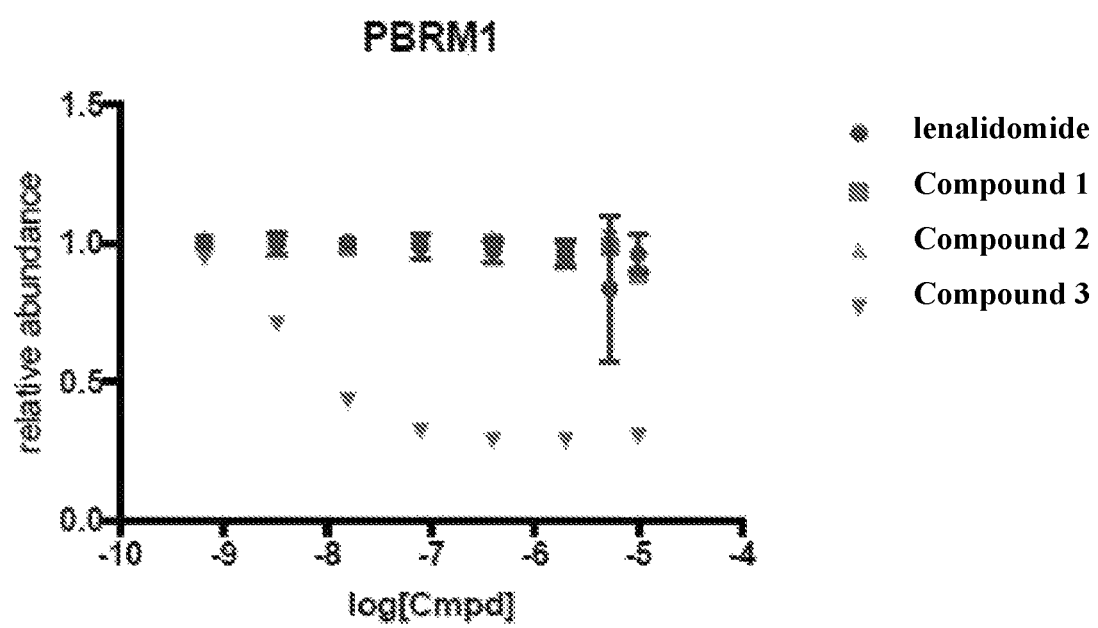
FIG. 2 is a graph that plots relative abundance (A.U.) as a function of the concentration of each of inventive compounds 1-3 as compared to a control (lenalidomide), generated from a PBRM1 bromodomain 5 (PB5) GFP/RFP degradation assay (in triplicate).

The results are shown in FIG. 2. They show that the carbon-only (i.e., alkylene) linker maintained potent degradation of PBRM1-PB5.

Example 17: Imaging Based PBRM1 PB5 GFP/RFP Degradation Assay

Cells stably expressing PBRM1 PB5 in Example 16, were seeded at 30-50% confluency in 384 well plates (3764, Corning) with 50 µL FluoroBrite DMEM media (Gibco, A18967) containing 10% FBS per well a day before compound treatment. Compounds and 100 nM dBET6 were dispensed using D300e Digital Dispenser (HP) normalized to 0.5% DMSO and incubated with cells for 5 h. The assay plate was imaged immediately using Acumen eX3/HCl (TTPLabtech) High Content Imager with 488 nm and 561 nm lasers in 2 m×1 m grid per well format. The resulting images were analyzed using CellProfiler (Carpenter et al., Genome Biol. 7R100 PIMD 17076895 (2006)). A series of image analysis steps ('image analysis pipeline') was constructed.

The CellProfiler pipeline steps were as follows. First, the red and green channels were aligned and cropped to target the middle of each well (to avoid analysis of heavily clumped cells at the edges), and a background illumination function was calculated for both red and green channels of each well individually and subtracted to correct for illumination variations across the 384-well plate from various sources of error. An additional step was then applied to the green channel to suppress the analysis of large auto fluorescent artifacts and enhance the analysis of cell specific fluorescence by way of selecting for objects under a given size, 30 A.U., and with a given shape, speckles. Cells that were mCherry-positive were then identified in the red channel filtering for objects between 8-60 pixels in diameter and using intensity to distinguish between clumped objects. The green channel was then segmented into GFP positive and negative areas and objects were labeled as GFP positive if at least 40% of it overlapped with a GFP positive area. The fraction of GFP-positive cells/mCherry-positive cells (GFP/ mCherry ratio) in each well was then calculated, and the green and red images were rescaled for visualization. The GFP/mCherry ratio was normalized to DMSO visualized in GraphPad Prism 7.

Figure 3A:
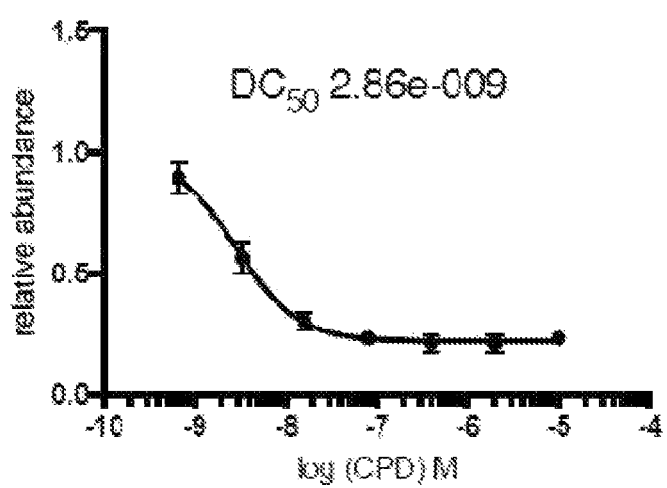
FIG. 3A-FIG. 3J are graphs that plot relative abundance (A.U.) as a function of concentration of each of inventive compounds 3-8 respectively (A-F) and compounds 11-13 respectively (H-J), as compared to a control (i.e., negative compound (G)), wherein concentration is expressed in units of log (inventive compound).
Figure 3B:
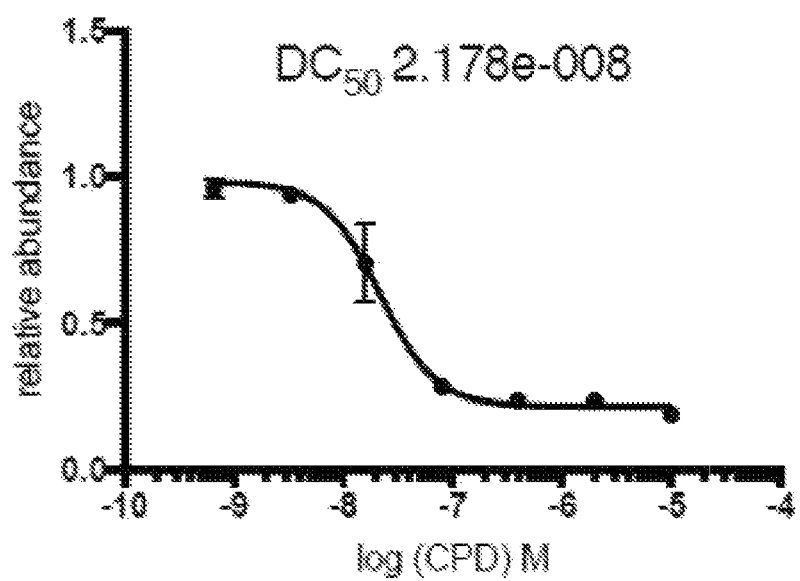
Figure 3C:
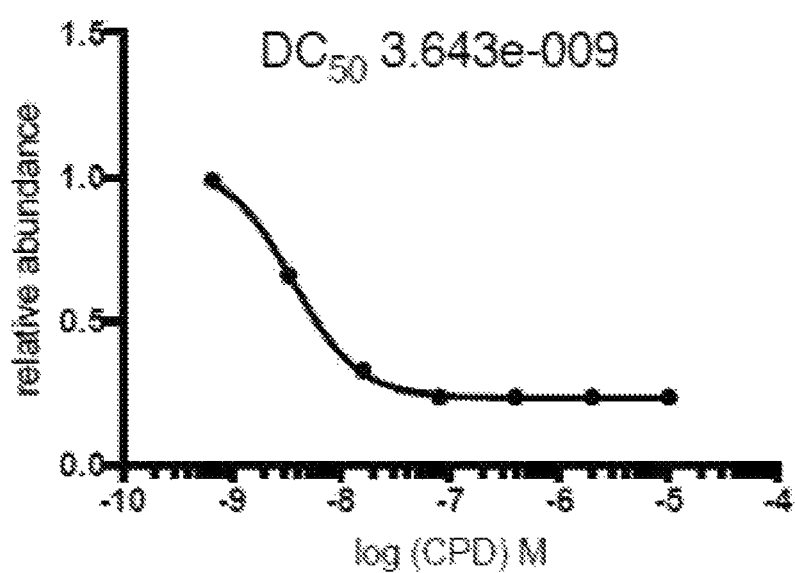
Figure 3D:
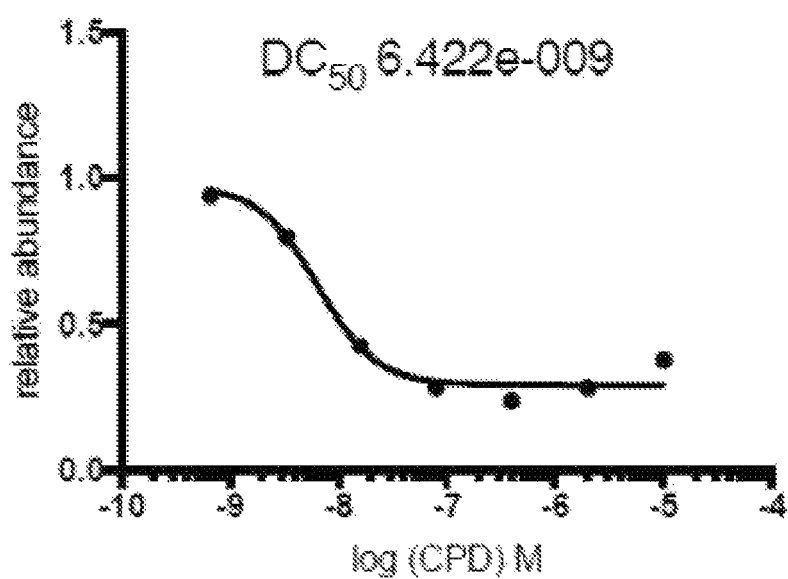
Figure 3E:
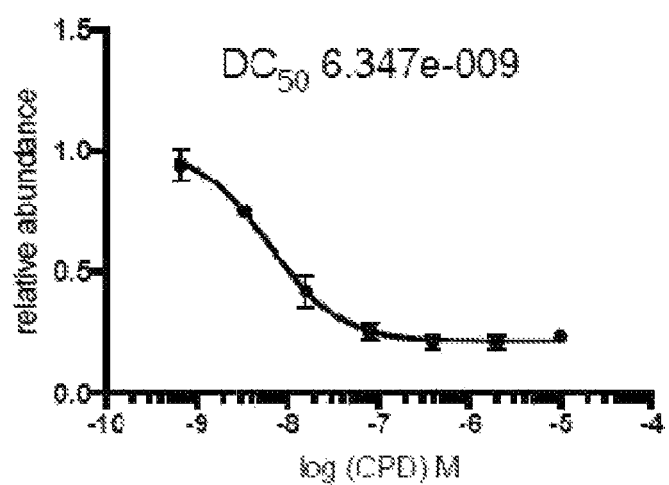
Figure 3F:
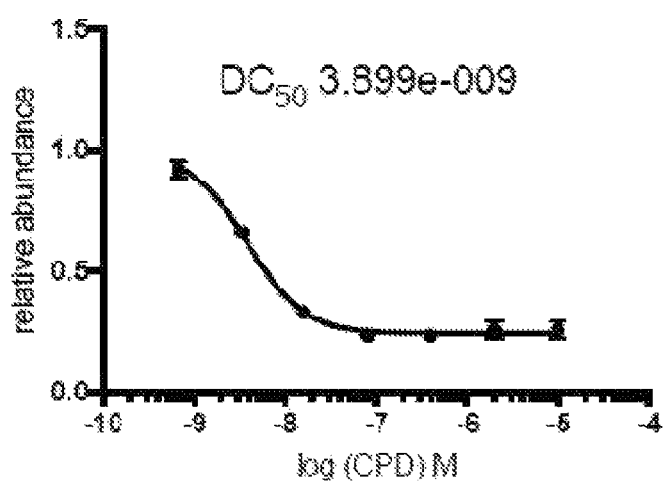
Figure 3G:
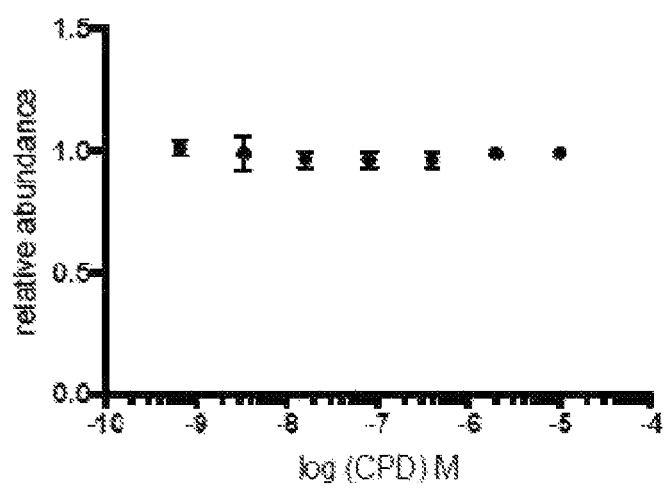
Figure 3H:
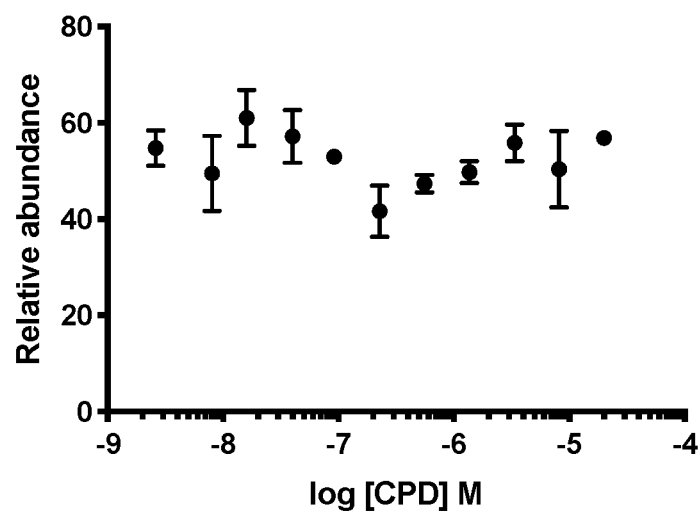
Figure 3I:
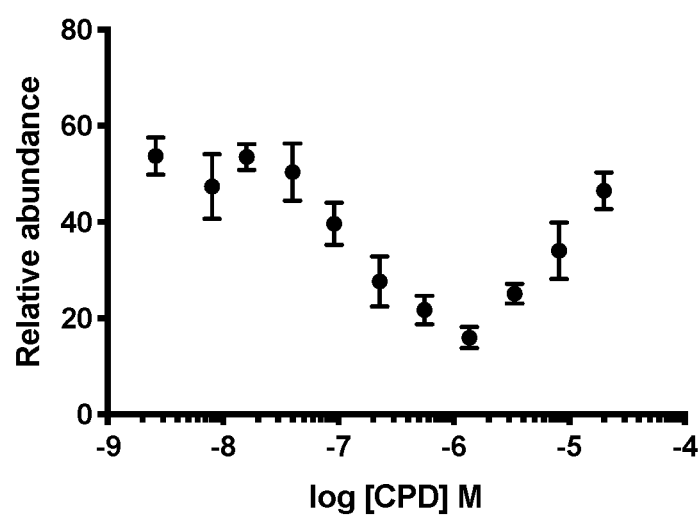
Figure 3J:
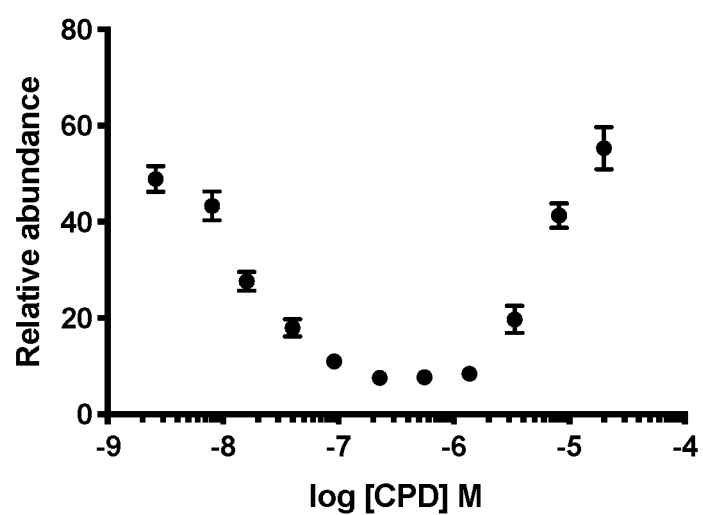

The results are shown in FIG. 3H-FIG. 3J for compounds 11, 12, and 13, respectively after 3 h of incubation. The VHL ligand-based degrader compound 12 was able to induce potent degradation of PBRM1 PB5, but compound 11, which lacks a ketone oxygen in the PBRM1 ligand, was less effective in degrading PBRM1 PB5. These results indicate that binding with the PBRM1 ligand requires a hydrogen bond acceptor at this position. The CRBN-based degrader compound 13, which includes an oxoacetamide and aliphatic linker of the thalidomide scaffold, shows potent degradation of PBRM1 PB5, but also shows a 'hook effect,' a known phenomenon for heterobifunctional degraders, where high compound concentration prevents effective complex formation and reduces protein degradation. In contrast, the hook effect at a concertation of 10 μM was not observed for any other CRBN-based degrader with an aliphatic linker and lacking the oxoacetamide feature (compounds 3-8), indicating that the oxoacetamide feature in this configuration is suboptimal.

Example 18: PBRM1 PB5 Reporter Assay

The assay described in Example 16 was repeated, using compounds 3-8 and the control ("negative compound" (G)).

The results are shown in FIG. 3A-FIG. 3G. FIG. 3A-FIG. 3F show the $DC_{50}$ values for Compounds 3-8, respectively. They are also set forth in the following table.

TABLE 1

| Compound No. | $DC_{50}$ Value |
|---|---|
| 3 | 2.86e−009 |
| 4 | 2.178e−008 |
| 5 | 3.643e−009 |
| 6 | 6.422e−009 |
| 7 | 6.347e−009 |
| 8 | 3.899e−009 |

Compounds in Table 1 show complete degradation of PBRM1 PB5 in a range of 100 nM-10 μM, indicating a large window of degradation activity. These compounds were able to induce potent degradation of PBRM1 PB5 at 10 μM, without any 'hook effect'.

Example 19: Kelly Cell PBRM1 Western—Western Blot for Cellular Degradation of Proteins Kelly cells were treated with compounds as indicated and incubated for 6 or 24 hours. Samples were run on 4-20% or Any kD™ SDS-PAGE Gels (Bio-Rad), and transferred to PVDF membranes using the iBlot 2.0 dry blotting system (Thermo-Fisher Scientific). Membranes were blocked with LI-COR blocking solution (LI-COR), and incubated with primary antibodies overnight, followed by three washes in LI-COR blocking solution and incubation with secondary antibodies for one hour in the dark. After three final washes, the membranes were imaged on a LI-COR fluorescent imaging station (LI-COR). Antibodies used: anti-PBRM1 at 1:500 dilution (Cell Signaling, clone D3F70), anti-GAPDH at 1:10,000 dilution (G8795, Sigma), IRDye 680 Donkey anti-mouse at 1:10,000 dilution (926-68072, LI-COR).

Figure 4:
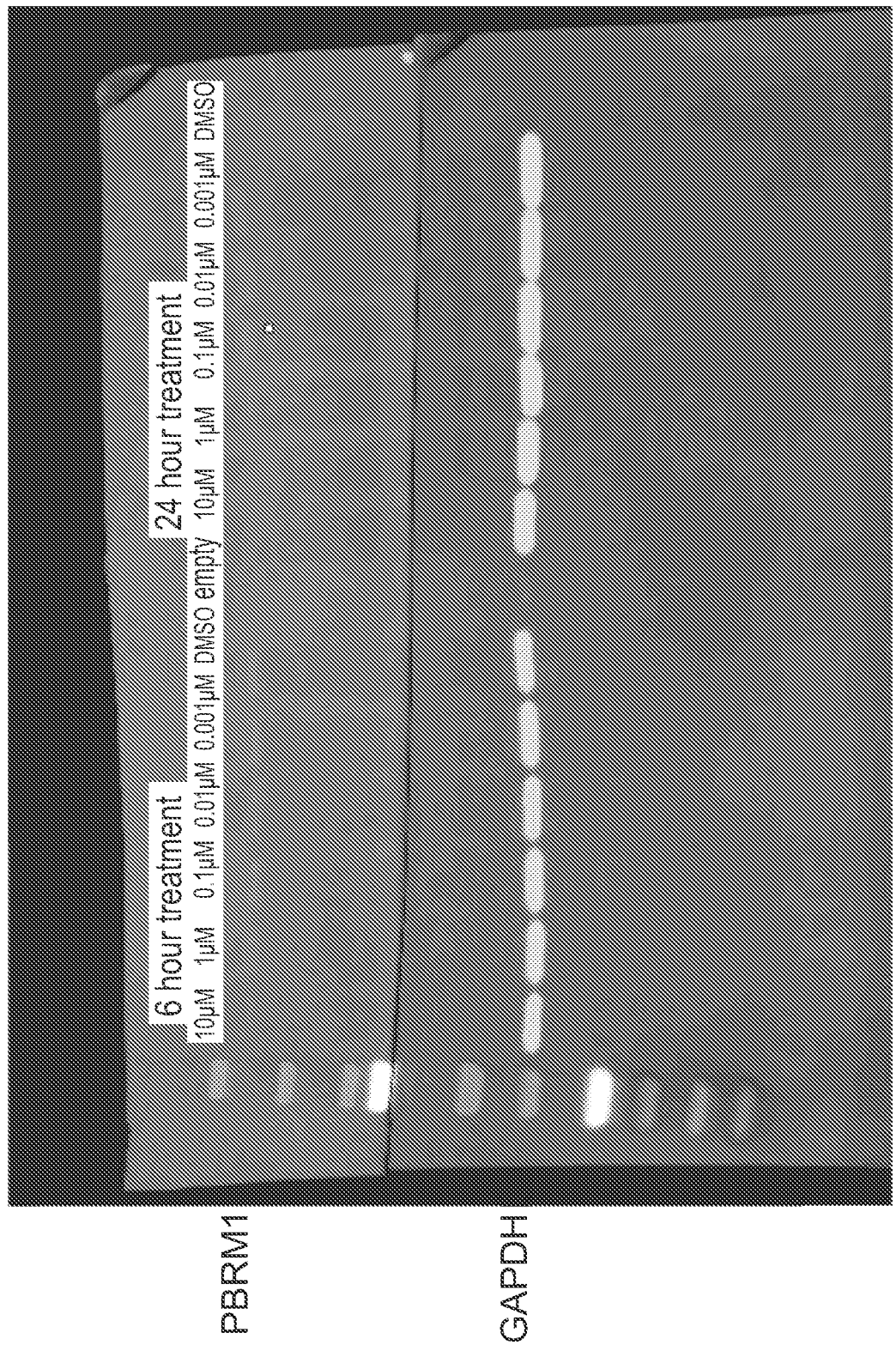
FIG. 4 is a Western blot that shows degradation of PBRM1 at 10 M of compound 1 at 6 hours, and 10 μM, 1 μM and 0.1 M of compound 1 at 24 hours, relative to glyceraldehyde 3-phosphate dehydrogenase (GAPDH), all compared to a control (dimethyl sulfoxide (DMSO)).

The results are shown in FIG. 4. Both 6 and 24 hour treatments showed near complete degradation of endogenous PBRM1 at 10 M concentration, with visible decrease of protein abundance at 1 M after 24 hours, while having no effect at protein levels of the reference protein, GAPDH.

All patent publications and non-patent publications are indicative of the level of skill of those skilled in the art to which this invention pertains. All these publications (including any specific portions thereof that are referenced) are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound represented by formula I:

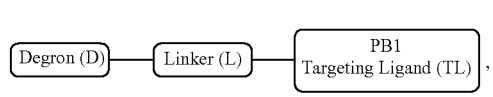

(I)

or a pharmaceutically acceptable salt or stereoisomer thereof, wherein the PB1 targeting ligand is represented by:

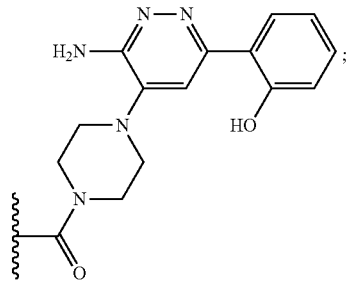 [SMILES: *C(=O)N1CCN(c2cc(-c3ccccc3O)nnc2N)CC1]

wherein the Linker is an alkylene chain that may be interrupted by, and/or terminate (at either or both termini) in at least one of —O—, —C≡C—, —C(O)—, or any combination thereof, wherein the interrupting and the one or both terminating groups may be the same or different;

wherein the Degron is represented by a formula selected from D1c-D1h:

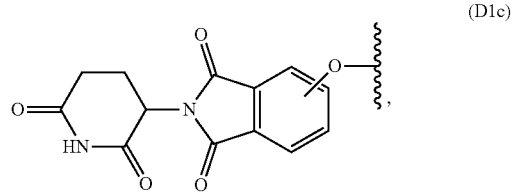

(D1c)

-continued

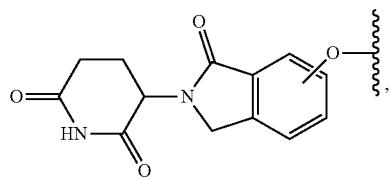 (D1d)

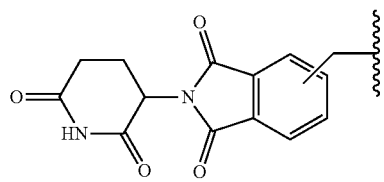 (D1e)

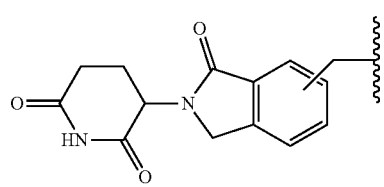 (D1f)

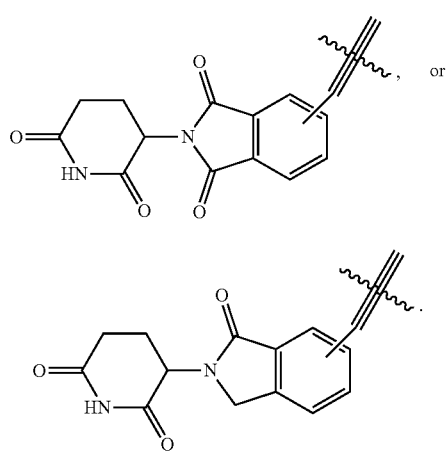
(D1f) or (D1g)

2. The compound of claim 1, wherein the Linker is an alkylene chain having 1-10 alkylene units.

3. The compound of claim 1, which is represented by any one of the following formulas:

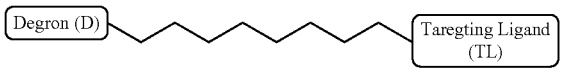

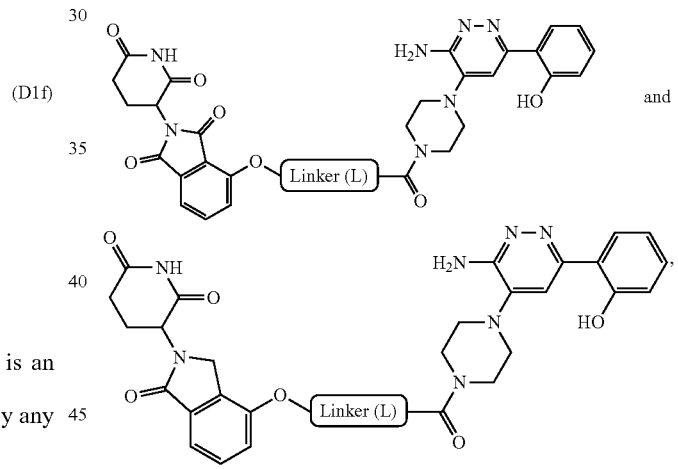

or a pharmaceutically acceptable salt or stereoisomer thereof.

4. The compound of claim 1, which is represented by any one of the following structures:

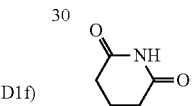
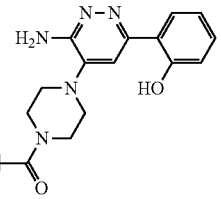 and
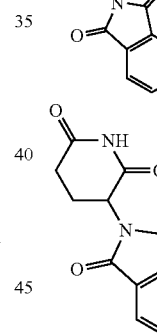
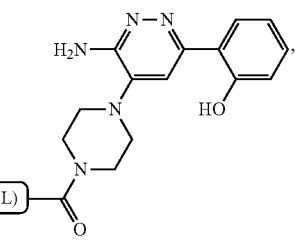

or a pharmaceutically acceptable salt or stereoisomer thereof.

5. A compound which is:

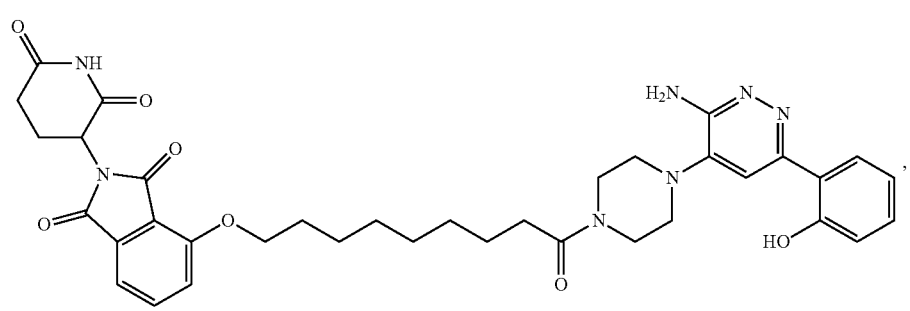

(3)

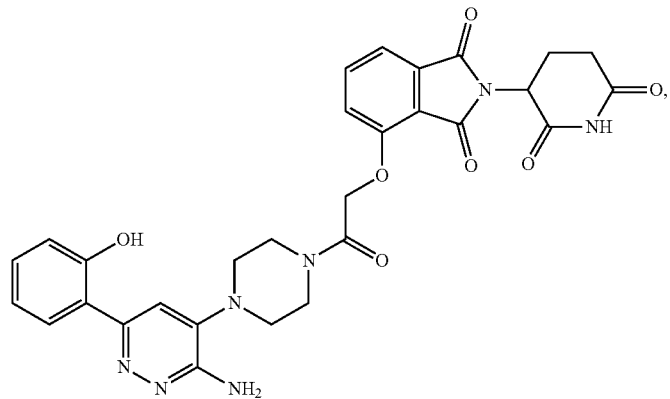
(4)
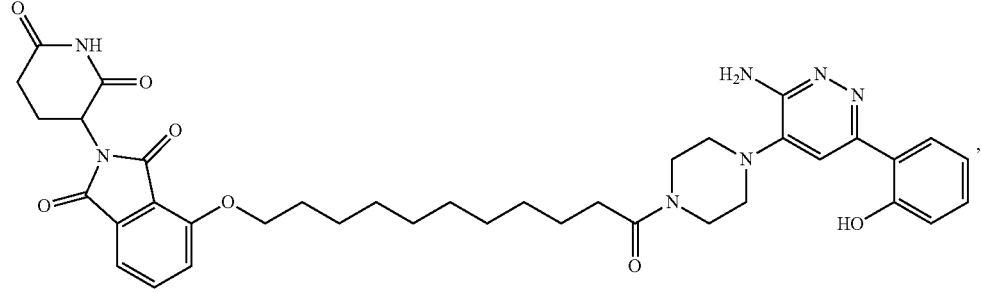
(5)
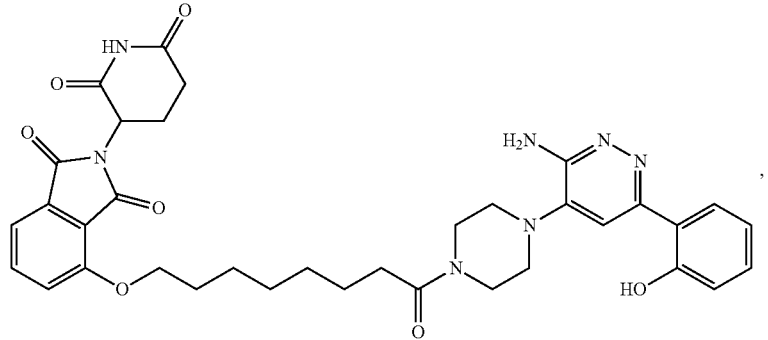
(6)
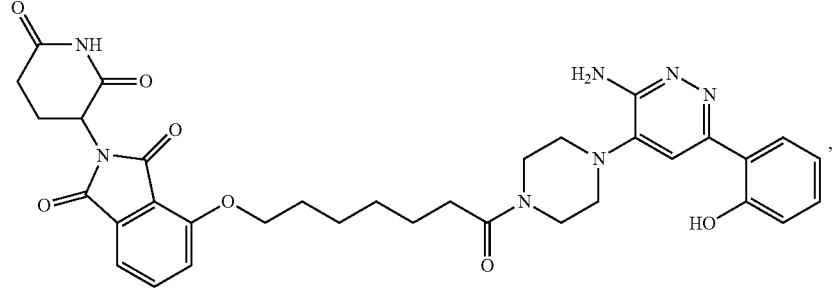
(7)

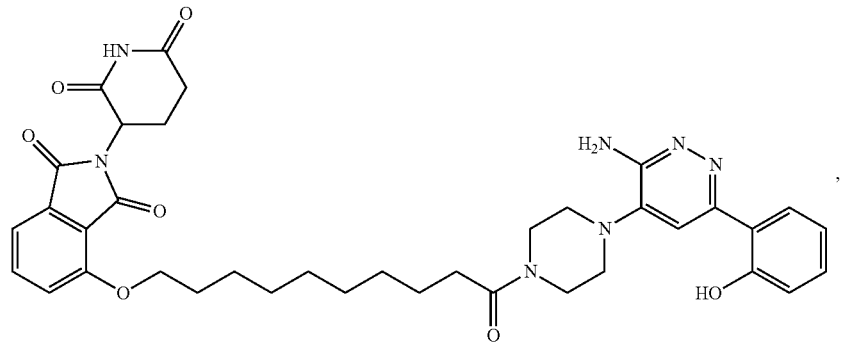
(8)
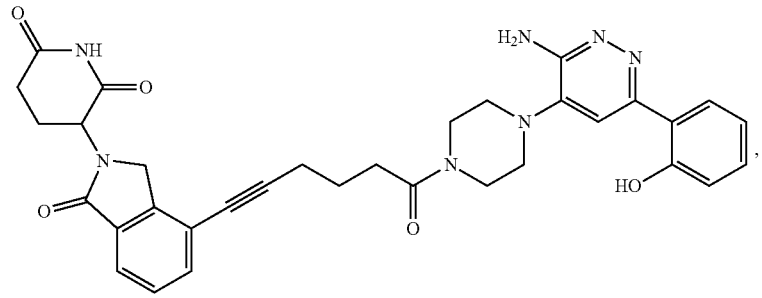
(9)
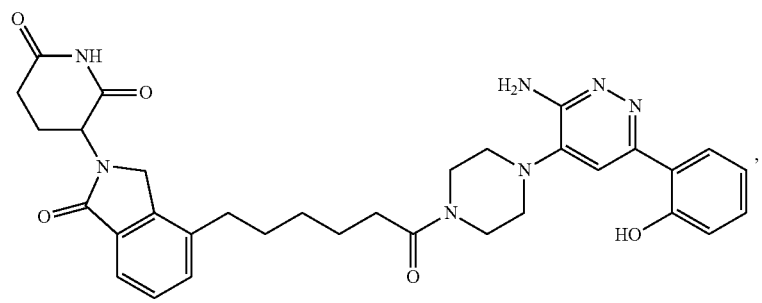
(10)
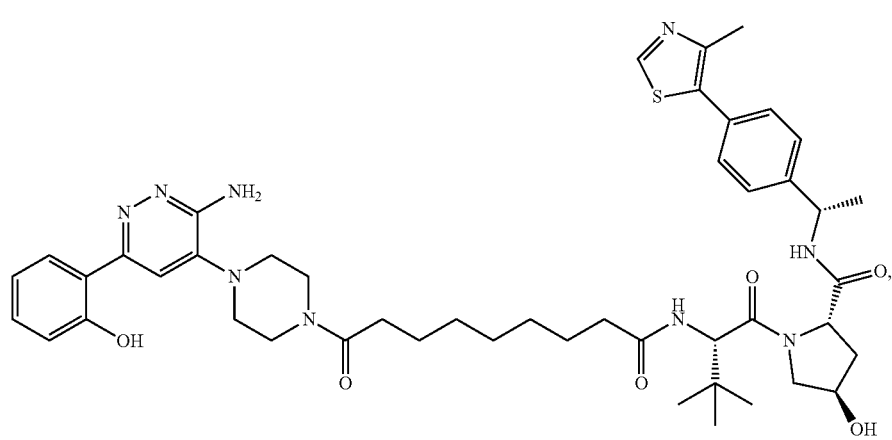
(12)

(13)
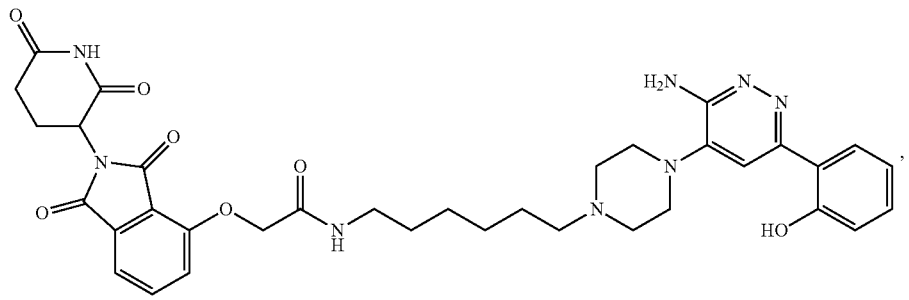
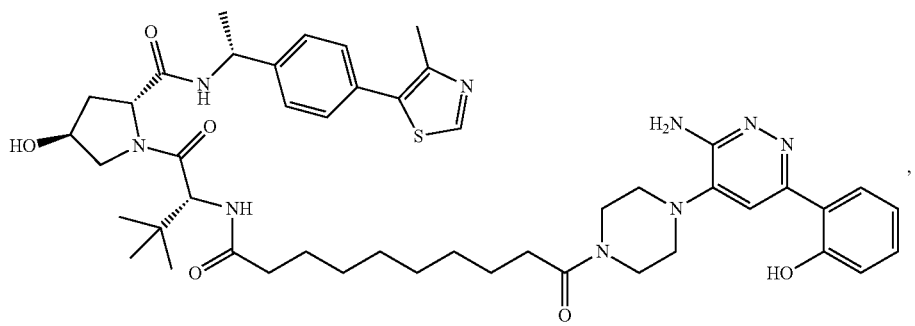
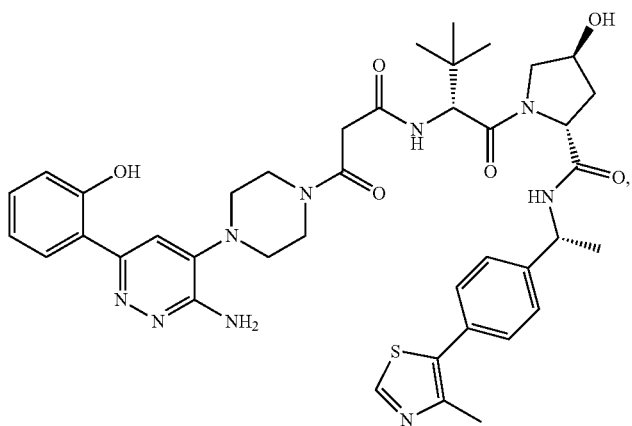
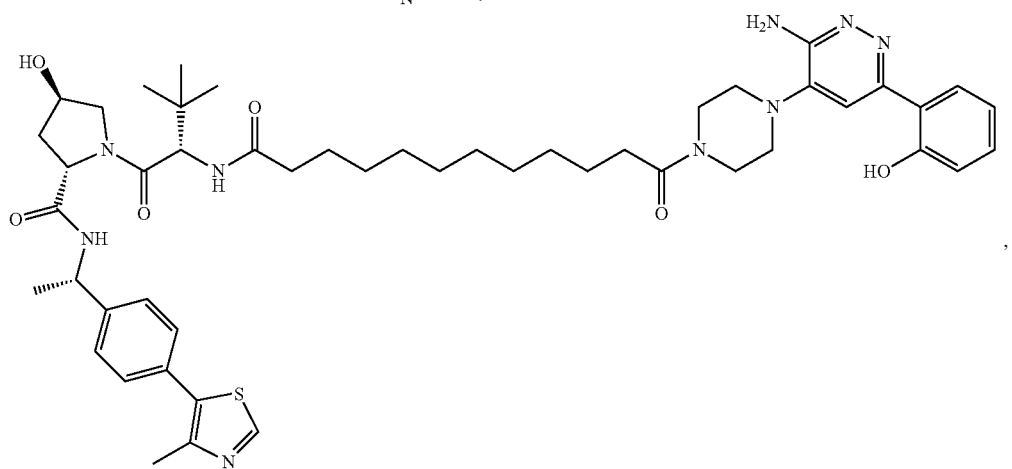

-continued
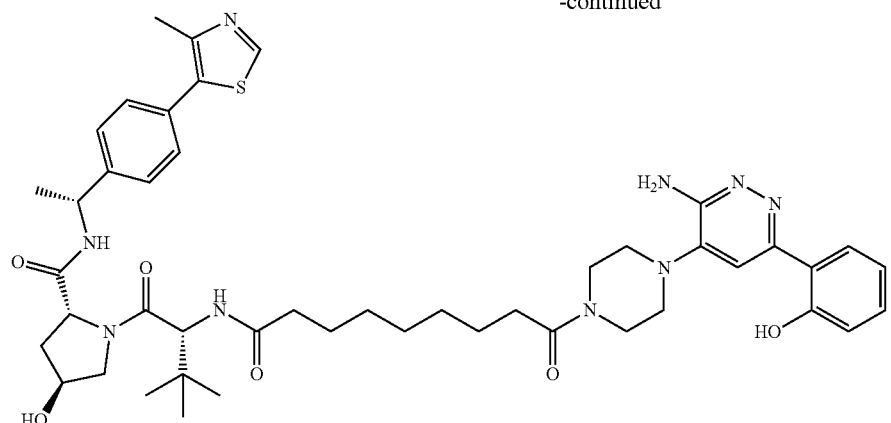
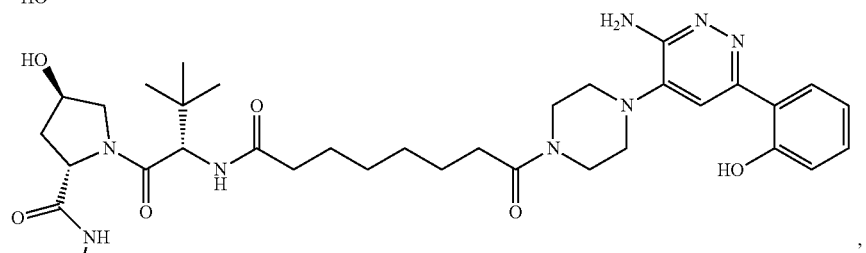
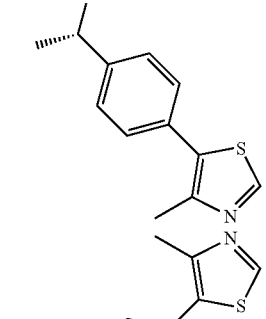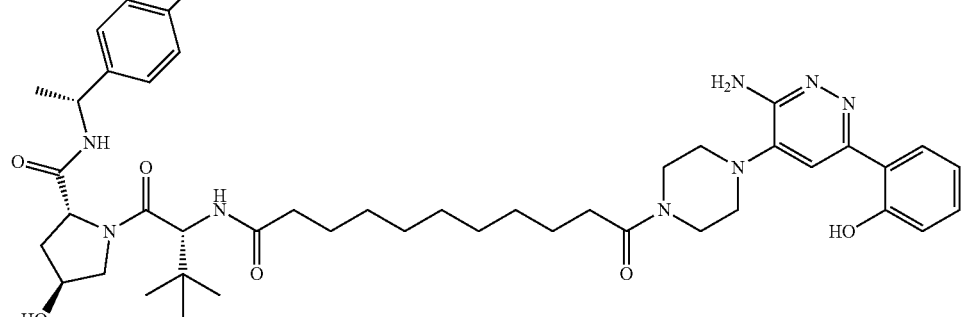
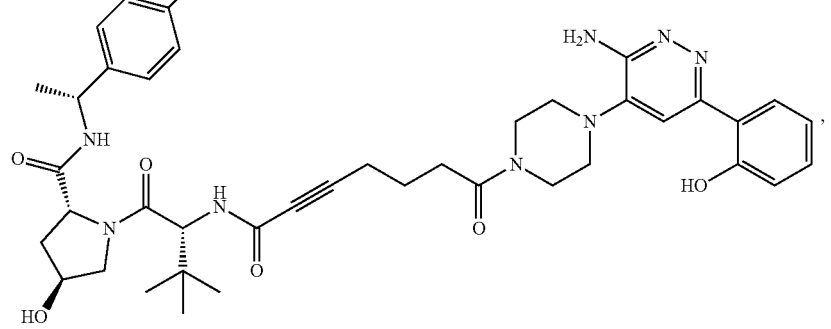

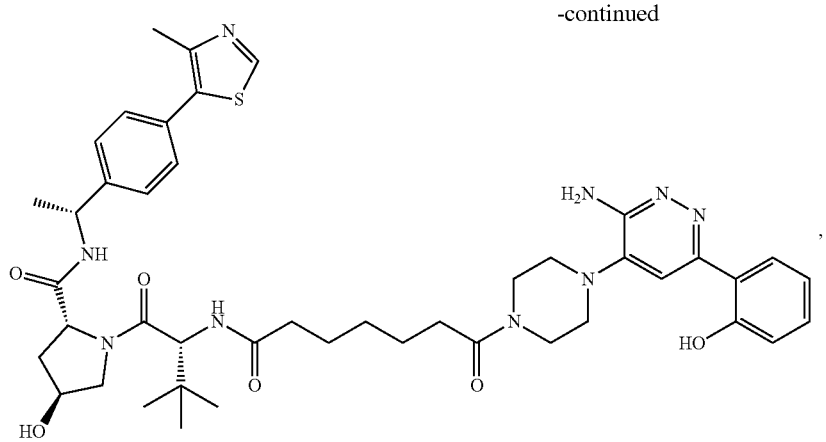

or a pharmaceutically acceptable salt or stereoisomer thereof.

6. A pharmaceutical composition, comprising a therapeutically effective amount of the compound or a pharmaceutically acceptable salt or stereoisomer of claim 1, and a pharmaceutically acceptable carrier.

7. A method of treating cancer mediated by PB1, comprising administering a therapeutically effective amount of the compound or a pharmaceutically acceptable salt or stereoisomer of claim 1 to a subject in need thereof.

8. The method of claim 7, wherein the cancer is melanoma.

* * * * *